US011319545B2

(12) United States Patent
Takagi et al.

(10) Patent No.: US 11,319,545 B2
(45) Date of Patent: May 3, 2022

(54) NUCLEIC ACID MOLECULE AND VECTOR INDUCING ENDOSPERM DEVELOPMENT IN SEED PLANT WITHOUT FERTILIZATION, TRANSGENIC SEED PLANT CAPABLE OF DEVELOPING ENDOSPERM WITHOUT FERTILIZATION AND METHOD FOR CONSTRUCTING SAME

(71) Applicant: NATIONAL INSTITUTE OF ADVANCED INDUSTRIAL SCIENCE AND TECHNOLOGY, Tokyo (JP)

(72) Inventors: Masaru Takagi, Tsukuba (JP); Miho Ikeda, Tsukuba (JP); Nobutaka Mitsuda, Tsukuba (JP); Yoshimi Oshima, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 16/977,878

(22) PCT Filed: Mar. 5, 2019

(86) PCT No.: PCT/JP2019/008706
§ 371 (c)(1),
(2) Date: Sep. 3, 2020

(87) PCT Pub. No.: WO2019/172282
PCT Pub. Date: Sep. 12, 2019

(65) Prior Publication Data
US 2021/0246458 A1  Aug. 12, 2021

(30) Foreign Application Priority Data
Mar. 5, 2018  (JP) .............................. JP2018-039033

(51) Int. Cl.
*C12N 15/82* (2006.01)
*A01H 5/10* (2018.01)

(52) U.S. Cl.
CPC ........... *C12N 15/8201* (2013.01); *A01H 5/10* (2013.01); *C12N 15/8234* (2013.01)

(58) Field of Classification Search
None
See application file for complete search history.

(56) References Cited

U.S. PATENT DOCUMENTS

| 2003/0126647 A1 | 7/2003 | Bilodeau et al. |
| 2010/0154077 A1* | 6/2010 | Emmanuel ........... C07K 14/415 800/281 |
| 2011/0035846 A1 | 2/2011 | Takagi et al. |
| 2011/0099664 A1 | 4/2011 | Takagi et al. |
| 2013/0139280 A1 | 5/2013 | Shin et al. |
| 2017/0029838 A1 | 2/2017 | Hazen et al. |

FOREIGN PATENT DOCUMENTS

| JP | 2005-143338 A | 6/2005 |
| JP | 2010-051293 A | 3/2010 |
| WO | WO 2000/016609 A1 | 3/2000 |
| WO | WO 2005/065446 A1 | 7/2005 |
| WO | WO 2009/113603 A1 | 9/2009 |
| WO | WO 2010/024269 A1 | 3/2010 |
| WO | WO 2011/161620 A1 | 12/2011 |

OTHER PUBLICATIONS

Noji et al. (Genbank database sequence accession No. Q8LPH6.1; published 2009).*
Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Doerks et al., (TIG, 14:248-250, 1998).*
Smith et al. (Nature Biotechnology, 15:1222-1223, 1997).*
Bork et al. (TIG, 12:425-427, 1996).*
McConnell et al. (Nature, 411:709-713, 2001).*
Hanzawa et al. (PNAS, 102:7748-7753, 2005).*
Wishart et al. (JBC, 270:26782-26785, 1995).*
Nishimura et al. (Plant Cell Physiol., 41(5):583-590, 2000).*
Yang et al. (PNAS, 98:11438-11443, 2001; abstract; pp. 11442-11443).*
Database UniProtKB/Swiss-Prot [online]; Accession No. Q84JD1; Jun. 1, 2003; URL:<https://www.ncbi.nlm.nih.gov/protein/Q84JD1>.
Database UniProtKB/Swiss-Prot [online]; Accession No. Q8LPH6, Oct. 1, 2002; URL:<https://www.ncbi.nlm.nih.gov/protein/Q8LPH6>.

(Continued)

*Primary Examiner* — Vinod Kumar
(74) *Attorney, Agent, or Firm* — Kilpatrick Townsend & Stockton LLP

(57) ABSTRACT

As a means for artificially inducing functional endosperm in a seed plant without fertilization, provided is a nucleic acid molecule that contains a base sequence encoding a polypeptide capable of inducing endosperm development, said nucleic acid molecule being to be transferred into the genome of the seed plant and expressed therein so as to induce endosperm development in the seed plant without fertilization.

7 Claims, 17 Drawing Sheets

Specification includes a Sequence Listing.

(56) References Cited

OTHER PUBLICATIONS

Database UniProtKB/Swiss-Prot [online]; Accession No. Q9LFB6; Oct. 1, 2000; URL:<https://www.ncbi.nlm.nih.gov/protein/Q9LFB6>.
Database UniProtKB/Swiss-Prot [online]; Accession No. Q8GXN7; Mar. 1, 2003; URL:<https://www.ncbi.nlm.nih.gov/protein/Q8GXN7>.
Database UniProtKB/Swiss-Prot [online]; Accession No. Q9FIL9; Mar. 1, 2001; URL:<https://www.ncbi.nlm.nih.gov/protein/Q9FIL9>.
Database UniProtKB/Swiss-Prot [online]; Accession No. Q84TG2; Jun. 1, 2003; URL:<https://mvw.ncbi.nlm.nih.gov/protein/Q84TG2>.
Database UniProtKB/Swiss-Prot [online]; Accession No. QOJQS2; Oct. 3, 2006; URL:<https://www.ncbi.nlm.nih.gov/protein/QOJQS2>.
Database UniProtKB/Swiss-Prot [online]; Accession No. Q5N9B7; Feb. 1, 2005; URL:<https://www.ncbi.nlm.nih.gov/protein/Q5N9B7>.
Japan Patent Office; International Search Report; PCT/JP2019/008706; dated May 21, 2019; 3 pgs.

* cited by examiner

```
                                                                                        Motif
At5g26660        MGRHSCC----PKQKLRKGLWSPEEDEKLINYITRHGHGCWSSVPKLAGLQRCGKSCRLRWINYLRPDL
Os05+0543600     MGRLSSCGGVQAKLRKGLWSPEDDKLYNHIIRHGVGCWSSVPKLAGLQRCGKSCRLRWINYLRPDL
                 ****   *  .: **********:***:****:**:*********************************

At5g26660        KRGAFSQDEESLIIELHAALGNRWSQIATRLPGRTDNEIKNFWNSCIKKKLRRKGIDPTTHKPLITN
Os05+0543600     KRGSFSQQEEDLIVALHELIGNRWSQIASHLPGRTDNEIKNFWNSCIKKKLPQRGLDPATHKPIAAA
                 ***:***:**.**::**.*:.******::**************:****** ::*:**:****::

At5g26660        ELQSLNVIDQKLTSSE-VVKSTGSINNLHDQSMVVSSQQGFWWFPANTT-----TTNQNSAFCF
Os05+0543600     AAAA-------TSSESAVTQVDEDHKPHGAAAAAAAADG---LAANAKQSVFDPFPVTDFGAGFDL
                      *   . :***:    . .:.: .: .****. .   . :*.**:       :. . *:*:*

At5g26660        SSSNTTVVSDQIVSLISSMSTSSSP---TPMTSNFSPAPNNWEQLNYCNTVPSQSNSIYSAFFGNQY
Os05+0543600     GAAN----------------MAAALYGSHPDDGAGFVADYSSVLDVSENLGYGESSSNSSN-----W
                 .:::                 :  *     ..* : .*     *::.*:*  *   : : ....:.

At5g26660        T---EASQTMNNNNPLVDQHRHHQDMKSWASEILHYTEHNQSETVIEAEVKPDIANYYWRSASSSSS
Os05+0543600     TCAEVSNVLD-----------------------SEVLNWAA--SAGADAAAKAEPFADMEQQH---SGYGGEY
                 *   .  *::                         *:::  ::     .  :. *: : * :*

At5g26660        PNQEAATLLHDANVEVYGKNLQKLNNMVFDQSL----
Os05+0543600     QVEDDATLEHKFSLPCHRQSLAQ------FDFNLEYF
                 ::  :***  .  :  .:: * *      **::*  *
```

FIG. 1A

```
At2g38090      ---------MNRGIEVMSPAT-YLETSNWLFQENR----------GTKWTAEENKKFENALAFY-DKDTPDRWSRVAAMLPGKTVGDVIKQYRELEEDVSDIEAG
At5g58900      ----------MEVMRPSTSHVSGGNWLMEETKSGVAASGEGATWTAAENKAFENALAVY-DDNTPDRWQKVAAVIPGKTVSDVIRQYNDLEADVSSIEAG
At5g01200      -MSSSTMYRGVNMFSPA-------NTNWIFQEVR--------EATWTAEENKRFEKALAYLDDKDNLESWSKIADLIPGKTVADVIKRYKELEDDVSDIEAG
Os01g0853700   -MMAEAL---REVL-PLPYFPGQPCWYLQERRG--------AEAWSAEENKVFERALAQV-DLDSPNRWEMVAAMLPRKTVIDVMNHYRDLENDVGSIEAG
Os01g0142500   MMMRDVC---MEVLPPMDHYASRGNWFM------------ARKWSPEENKQFERALAGL-DLRCPD-WDRVARAIPGRSALEVMNHFRDLELDVQQIENG
                            :               :               *  : :  **.****  :   *  :.   : **       :: *  ** .** **

At2g38090      LIPIPGYA--------SDSFTLD-WGGYDGASGNN-------GFNMNGY-YFSAAGGKRGSAART---------AEHERKKGVPWTEEEHRCFLMGLKKYSKGDWR
At5g58900      LIPVPGYIT-------SPFFTLD-WAGG---------------GGGCNGFKPGHQVCNKRSQAGRS---------PELERKKGVPWTEEHHRFLMGLKKYGKGDWR
At5g01200      LIPIPGY---------------WAGG---------------GGDASSAANSDYFPGLENSSYGYDYVVGGKRSSPAMTDCFRSPMPEKERKKGVPWTEDRHRPFLMGLKKYGKGDWR
Os01g0853700   LVPFPHYSSSLSPASSGFTLQDWDGSDG----------GFRRGCYL-----KR---GRA--------PDQERKKGVPWTEEHRCFTMGLKKYSPGDWR
Os01g0142500   MVPFFVYGA--AAAGGAFTLQ-WDGAHGV----------GDFRNAYRFGGGGGGKRH-FGRT------PEQERKKGVPWTEEHHKFTLGLKKYGKGDWR
                 :*:.*    .                   *                              *                   :      *  **  **** **.*  *:* ***

═══════════════ Motif ═══════════════

At2g38090      NIARNFYTTRIFPTQVASHAQKYIFIRQVNGGKDKRRSSIHDITTVNI═PDSPDAAAADNATANAPCSPPSVGGNQRE----TSEWEGQTLYDETAAAFYNQNA
At5g58900      NISRNFVITRIFPTQVASHAQKYIRQISGGKDKRRASIHDITVNI═VVGDQRSRLTAFPWN-QTDNNGTQA------DA
At5g01200      NIAKSFVFTRIFPTQVASHAQKYFEROLTDGKDKRRSSIHDITVNI═PDADASATA--TTADVALSP------NS
Os01g0853700   NISRYFVTSRIFPTQVASHAQKYFIRLNSGGKDKRRSSIHDITVNI═PEEDTSNPS------PSPPSV-------LI'TAS-----DQ
Os01g0142500   NISRNFYQTRIFPTQVASHAQKYFIRLNSGGEDKRRSSIHDITVNI═TDDRPPS-------PSQSSLISNQ------SNTSTLTAAV----AP
               *:::::: :*:*********** **::  **:****:****:***  .                                        *   *

At2g38090      FSETLLLG--MSSTPYMAKLQEQSFLNA------SQFESYNA---------------YLQM-------
At5g58900      FNITI-GNAISGVHSYGQVMIGGYNNA------DSCYDAQNT-----------MFQL-------
At5g01200      FDVFL-----QPNPHY------SFASA------SASSYYNA-----------FPQWS-------
Os01g0853700   LGSLVDTRPVPPPSLGAQR--HFMSPLPGALGVSHHPYGNVKLEPNASFLAGGGTGPGLDDAILLQMQCGHL------GLQCGGPLHDQLAASRSILF
Os01g0142500   FSSTADVK------PQNAANA--SFNSP----------------SRTLGMAGYGMGLQDQ----GLQCGGPLHDQLAASRSILF
                :                                   :
```

FIG. 1B

A     ProCaMV 35S-Ω-[At5g07260 SRDX]-ter

B     ProCaMV 35S-Ω-[At5g26660 SRDX]-ter

C     ProCaMV 35S-Ω-[At5g01200 SRDX]-ter

D     ProCaMV 35S-Ω-[At2g38090 SRDX]-ter

E     ProCaMV 35S-Ω-[At5g58900 SRDX]-ter

F     ProCaMV 35S-Ω-[At3g16350 SRDX]-ter

G     ProAt5g01200-Ω-[At5g01200 SRDX]-ter

FIG. 2A

H    ProZmUBQ1—[Os01g0142500 SRDX]-ter

I    ProZmUBQ1—[Os05g0543600 SRDX]-ter

J    ProOsFST—[Os01g0853700 SRDX]-ter

K    ProOsFST—[Os04g0569100 SRDX]-ter

FIG. 2B

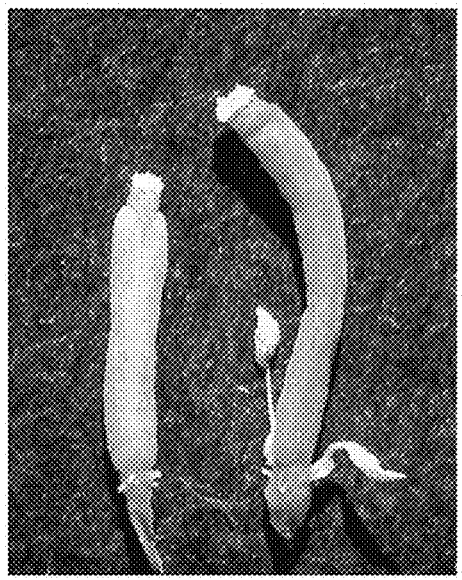
Wild-type plant | Transformed plant G
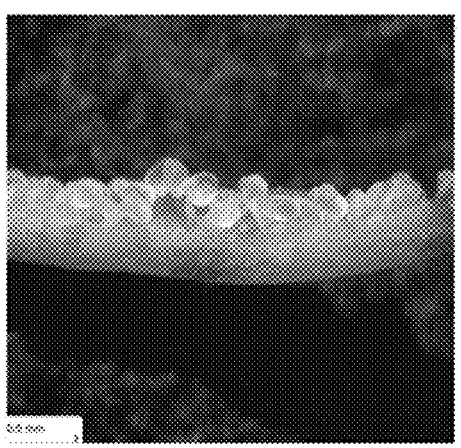
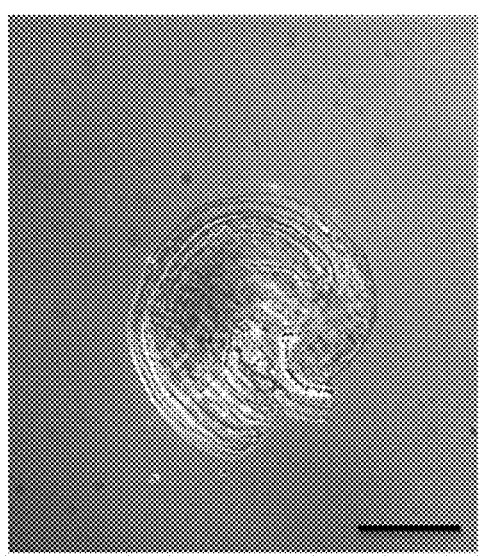
FIG. 4

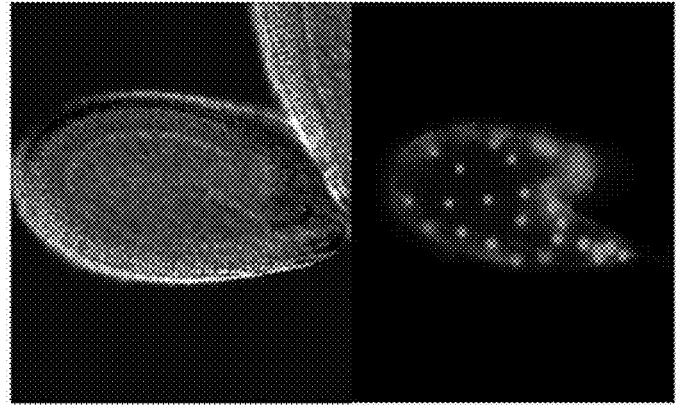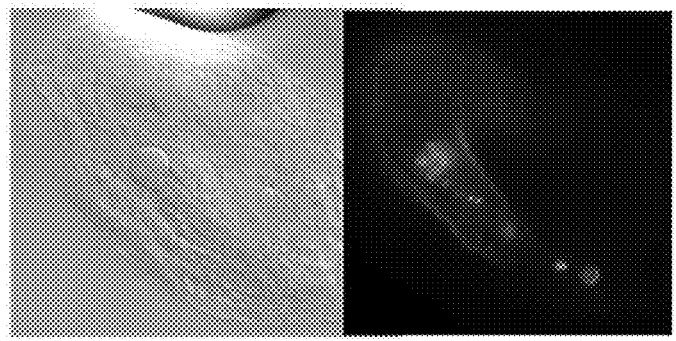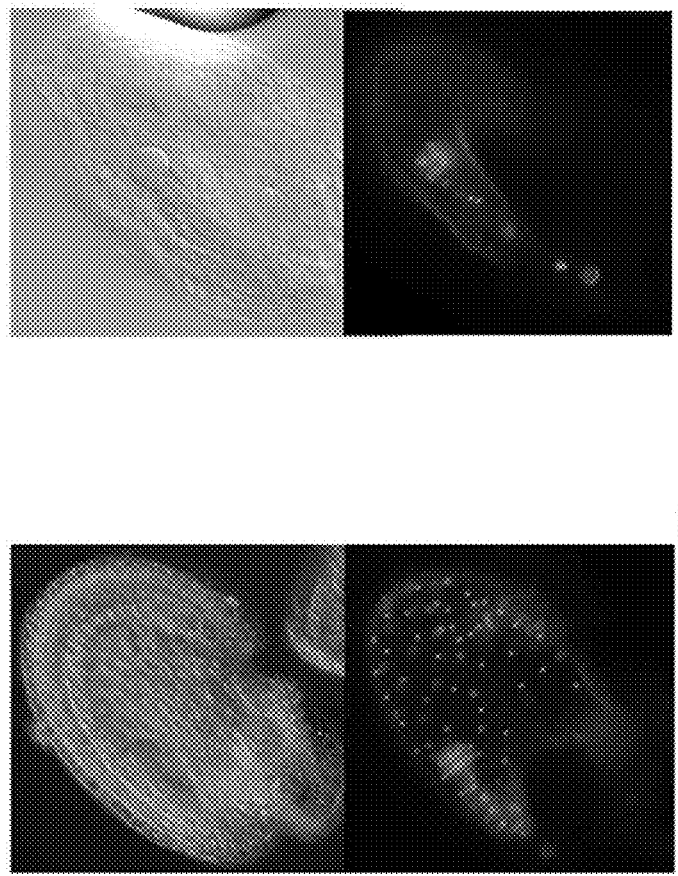
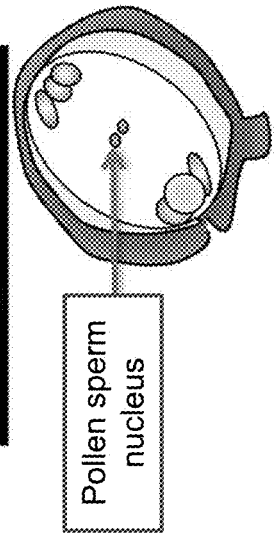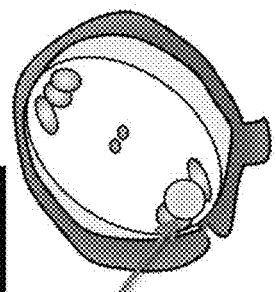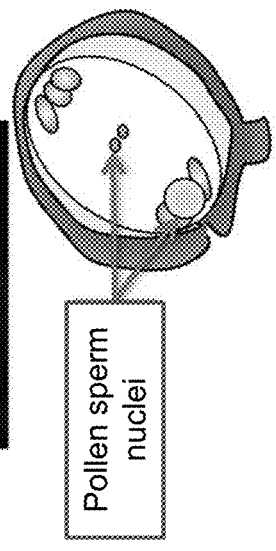
FIG. 8A — Both embryo and endosperm fertilized (with two pollen tubes reaching at ovule) — Pollen sperm nuclei
FIG. 8B — Only embryo fertilized — Pollen sperm nucleus
FIG. 8C — Only endosperm fertilized — Pollen sperm nucleus

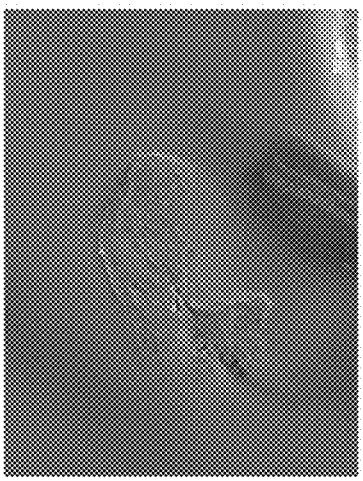 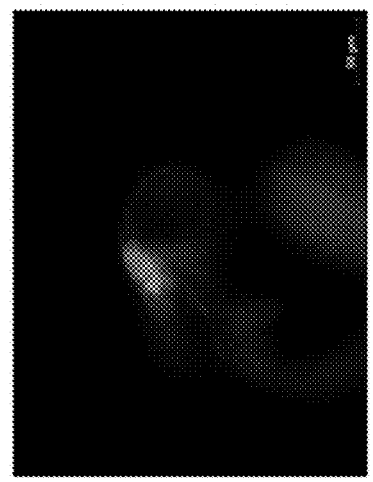
FIG. 9A Wild-type
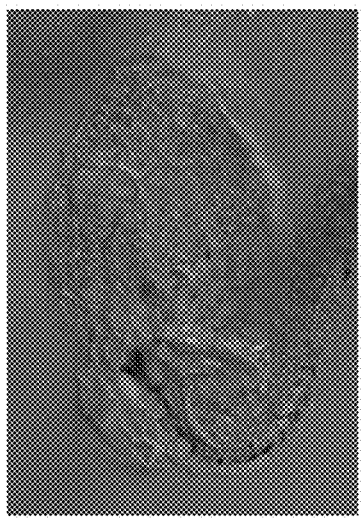 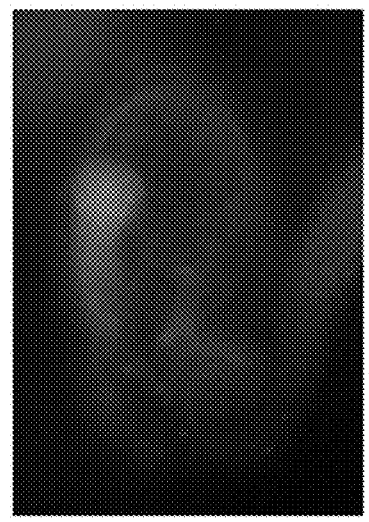
FIG. 9B Transformed plant A
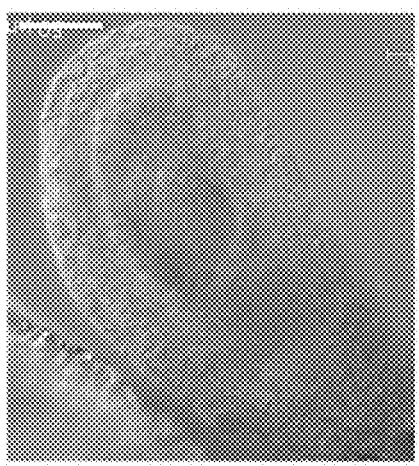 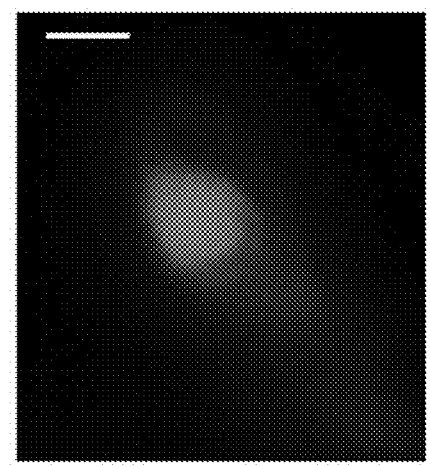
FIG. 9C Transformed plant G

SEQUENCE LISTING

```
<160> NUMBER OF SEQ ID NOS: 72

<210> SEQ ID NO 1
<211> LENGTH: 541
<212> TYPE: PRT
<213> ORGANISM: Arabidopsis thaliana
<220> FEATURE:
<223> OTHER INFORMATION: At5g07260 Polypeptide

<400> SEQUENCE: 1

Met Tyr His His Leu Gln Thr Arg Ile Phe Leu His Gln Gln Asn Asp
1               5                   10                  15

Leu Leu Arg Ala Glu Asn Arg Ala Arg Ile His Ala Met Thr Ser Pro
            20                  25                  30

Ser Ile Cys Arg Ser Cys Glu Glu Pro Ile Ile Ser Thr Glu Glu Arg
        35                  40                  45

Glu Leu Trp Leu Glu Asn Ala Arg Leu Arg Ser Glu Ile Asp Thr Leu
    50                  55                  60

Thr Cys Phe Ile Trp Arg Leu Asn Ser Phe Arg Asn Leu Tyr Pro Ala
65                  70                  75                  80

Phe Ala Thr Ser Leu Thr Glu Val Gly Tyr Gly Val Ala Val Met Thr
                85                  90                  95

Ser Leu Ser Leu Lys Glu Val Val Phe Leu Ala Arg Gln Arg Thr Pro
            100                 105                 110

Met Trp Thr Ser Asn Gly Arg Leu Asn Leu Asp Glu Tyr Tyr Ser Lys
        115                 120                 125

Leu Phe Pro Trp Tyr Ala Arg Asn Ala Pro Gly Phe Val His Glu Val
    130                 135                 140

Ser Arg Ala Ser Ala Phe Val Pro Cys Asp Ala Ser Ser Leu Val Ala
145                 150                 155                 160

Asn Leu Met Asn His Val Ser Trp Gln Lys Ile Phe Pro Ser Ile Ile
                165                 170                 175

Ala Asp Val Ser Val Glu Ser Gln Gln Arg Gly Leu Gln Lys Ile Asn
            180                 185                 190

Val Asn Phe Met Pro Gln Ile Ser Pro Leu Ile Gln Thr Arg Asn Val
        195                 200                 205
```

```
Lys Leu Leu Arg Arg Ser Arg His Ile Glu Asp Asp Thr Trp Ala Ile
    210                 215                 220
Ala Glu Ile Ser Met Tyr Phe Ser Ser Tyr Ala Gln His Leu Arg Pro
225                 230                 235                 240
Glu Tyr Met Arg Phe Pro Ser Gly Tyr Leu Ile Gln His Ile Ala Asn
                245                 250                 255
Gly Ile Ser Lys Val Thr Ile Leu Asp His Trp Val Tyr Lys Glu Glu
                260                 265                 270
Glu Gly Met Asn Thr Phe Asn Ser Asn Ser Glu Phe Gly Ala Gln Arg
            275                 280                 285
Trp Leu Thr Ala Leu Gln Lys His Tyr Tyr Asn Thr Cys Pro Val Ser
    290                 295                 300
Ile Pro Ser Ile Gly His Asn Ile Gln Ile Phe Asp Gln Ile Cys Arg
305                 310                 315                 320
Lys Asn Leu Leu Asn Leu Ser Ser Phe Met Val Asn Val Phe Cys Ser
                325                 330                 335
Gly Val Cys Gly Ile Thr Gly Gln Arg Trp Asn Arg Leu Asn Thr Val
                340                 345                 350
Gly Val Ser Ala Asn Asn Ile Arg Met Phe Thr Gln Glu Ser Arg Gly
            355                 360                 365
Met Ser Gly Ile Pro Cys Val Leu Val Ser Ala Thr Gly Leu Ala Arg
    370                 375                 380
Met His Thr Lys Pro Glu Val Met Phe Gly Leu Ile Asn Gly Ala Glu
385                 390                 395                 400
Lys Gln Glu Ile Trp Ser Tyr Leu Glu Ser Ala Lys Asp Met Lys Glu
                405                 410                 415
Leu Ile Arg Ile Gly Arg His Pro Asn Ser Trp Asn Glu Val Ser Val
                420                 425                 430
Phe Ser Ile Glu Trp Lys Gly Ser Lys Glu Trp Tyr Leu Ile Gln Glu
            435                 440                 445
Thr Tyr Tyr Asp Glu Ser Gly Ala Met Ile Ile His Thr Cys Val Glu
    450                 455                 460
Ala Pro Tyr Phe Ala Ala Ala Ile Asn Gly Gly Asp Leu Ser Gly Val
465                 470                 475                 480
Glu Leu Leu Pro Ser Gly Phe Thr Ile Ile Pro Cys Glu Ser Gln Glu
                485                 490                 495
Cys Phe Val Thr Ala Ser Cys Tyr Val Lys Ala Asp Gln Thr Met Val
                500                 505                 510
Thr Ser Pro Asn Glu Leu Gly Ser Tyr Met Glu Asn Met Val Thr Asn
            515                 520                 525
Ile Leu Gly Asn Val Gln Asn Ala Leu Pro Val His Arg
    530                 535                 540

<210> SEQ ID NO 2
<211> LENGTH: 1626
<212> TYPE: DNA
<213> ORGANISM: Arabidopsis thaliana
<220> FEATURE:
<223> OTHER INFORMATION: At5g07260 DNA

<400> SEQUENCE: 2
atgtatcatc atcttcaaac gaggattttt ctccaccaac aaaatgattt gctgagagca      60 gaaacagag  ctaggattca tgctatgacc tctccatcaa tctgcagatc ttgtgaggag     120
cccatcattt caaccgaaga gagggagcta tggttggaga atgctcgtct tcggtccgag     180
```

```
attgatacat tgacttgttt catatggaga ttaaattcgt tcaggaacct atatcccgca    240
tttgctacgt ctttgactga agtgggttac ggagtggcgg ttatgacgtc actttcgctg    300
aaagaagttg tttttcttgc gaggcaaaga actccgatgt ggacaagtaa cgggagattg    360
aatctcgacg aatactactc taaattattt ccttggtacg caagaaacgc acccgggttt    420
gtacatgagg tatcaagagc ttctgctttt gtcccatgtg atgcttcatc gctcgtggca    480
aatcttatga atcatgtaag ttggcaaaaa atctttccgt caatcatcgc ggatgtgtct    540
gtggaatcac aacaacgggg attgcaaaag attaatgtga attttatgcc acaaatctct    600
cctctcattc aaactcggaa tgtgaaactt cttcgacgct cgaggcatat agaggatgat    660
acatgggcta ttgcagaaat ttctatgtat ttcagctcat atgcgcaaca tttacgtcct    720
gaatatgtga gatttccttc tggatatctt atccaacata tagccaatgg tatctctaag    780
gtaaccattc tcgaccattg ggtttacaag gaagaagaag gcatgaacac tttcaattca    840
aactctgaat tggtgcaca gagatggctc actgctctcc aaaagcatta ctacaacacc    900
tgccccgttt ctattccttc aattggtcac aatattcaaa tattcgacca gatctgtcgc    960
aagaacttgc ttaacctatc ttcatttatg gttaacgtat tttgttcggg agtttgcggg   1020
ataactggac aaaggtggaa tcggttgaat acagttggag tttcggctaa taacattaga   1080
atgttcacgc aagaaagtcg aggcatgagt gggatccctt gcgttttggt tagcgctacc   1140
ggtttagcta gaatgcacac taaaccagaa gtaatgtttg gattaatcaa cggtgcagaa   1200
aaacaagaaa tatggagtta tttagagtct gctaaagata tgaaagaact aattcgtatc   1260
ggaagacatc ctaattcatg gaatgaagtc tctgtttttca gcattgagtg gaagggttcg   1320
aaggagtggt atctgattca agaaacatac tacgatgaat caggagcaat gataatccac   1380
acttgcgtag aagcgccata ttttgcagct gcaataaacg gtggggattt gtctggcgtc   1440
gaactgttac ccagtggatt caccataata ccatgcgaat cacaagaatg tttcgtgaca   1500
gctagttgtt atgttaaggc tgaccaaact atggtcacga gtccaaatga gctggggagt   1560
tatatggaga acatggtcac taacattcta ggaaatgtcc aaaatgctct tccagtccac   1620
cgttga                                                               1626
```

<210> SEQ ID NO 3
<211> LENGTH: 352
<212> TYPE: PRT
<213> ORGANISM: Arabidopsis thaliana
<220> FEATURE:
<223> OTHER INFORMATION: At5g26660 Polypeptide

<400> SEQUENCE: 3

```
Met Gly Arg His Ser Cys Cys Phe Lys Gln Lys Leu Arg Lys Gly Leu
1               5                   10                  15

Trp Ser Pro Glu Glu Asp Glu Lys Leu Leu Asn Tyr Ile Thr Arg His
            20                  25                  30

Gly His Gly Cys Trp Ser Ser Val Pro Lys Leu Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Ala Phe Ser Gln Asp Glu Ser Leu Ile Ile Glu
65                  70                  75                  80

Leu His Ala Ala Leu Gly Asn Arg Trp Ser Gln Ile Ala Thr Arg Leu
                85                  90                  95

Pro Gly Arg Thr Asp Asn Glu Ile Lys Asn Phe Trp Asn Ser Cys Leu
```

```
                100                 105                 110
Lys Lys Lys Leu Arg Arg Lys Gly Ile Asp Pro Thr Thr His Lys Pro
            115                 120                 125

Leu Ile Thr Asn Glu Leu Gln Ser Leu Asn Val Ile Asp Gln Lys Leu
        130                 135                 140

Thr Ser Ser Glu Val Val Lys Ser Thr Gly Ser Ile Asn Asn Leu His
145                 150                 155                 160

Asp Gln Ser Met Val Val Ser Ser Gln Gln Gly Pro Trp Trp Phe Pro
                165                 170                 175

Ala Asn Thr Thr Thr Thr Asn Gln Asn Ser Ala Phe Cys Phe Ser Ser
            180                 185                 190

Ser Asn Thr Thr Thr Val Ser Asp Gln Ile Val Ser Leu Ile Ser Ser
        195                 200                 205

Met Ser Thr Ser Ser Pro Thr Pro Met Thr Ser Asn Phe Ser Pro
    210                 215                 220

Ala Pro Asn Asn Trp Glu Gln Leu Asn Tyr Cys Asn Thr Val Pro Ser
225                 230                 235                 240

Gln Ser Asn Ser Ile Tyr Ser Ala Phe Phe Gly Asn Gln Tyr Thr Glu
                245                 250                 255

Ala Ser Gln Thr Met Asn Asn Asn Pro Leu Val Asp Gln His His
            260                 265                 270

His His Gln Asp Met Lys Ser Trp Ala Ser Glu Ile Leu His Tyr Thr
        275                 280                 285

Glu His Asn Gln Ser Ser Glu Thr Val Ile Glu Ala Glu Val Lys Pro
    290                 295                 300

Asp Ile Ala Asn Tyr Tyr Trp Arg Ser Ala Ser Ser Ser Ser Pro
305                 310                 315                 320

Asn Gln Glu Ala Ala Thr Leu Leu His Asp Ala Asn Val Glu Val Tyr
                325                 330                 335

Gly Lys Asn Leu Gln Lys Leu Asn Asn Met Val Phe Asp Gln Ser Leu
            340                 345                 350

<210> SEQ ID NO 4
<211> LENGTH: 1059
<212> TYPE: DNA
<213> ORGANISM: Arabidopsis thaliana
<220> FEATURE:
<223> OTHER INFORMATION: At5g26660 DNA

<400> SEQUENCE: 4
atgggaagac attcttgttg ttttaagcag aagctaagaa aaggcctttg gtctcctgaa      60
gaagatgaga aacttctcaa ttacatcact agacatggtc atggctgttg gagttctgtc     120
cctaaactcg caggtttgca aagatgtgga aagagttgta gacttaggtg gataaattat     180
ttgagaccag atttaaagag aggagctttc tctcaagacg aagaaagctt gatcattgag     240
ctccatgctg cattaggcaa cagatggtct caaatcgcaa cgcggttacc gggaagaaca     300
gacaacgaga tcaaaaactt tggaactcat gtcttaaga agaagctgag aagaaaggc     360 attgacccaa caacacataa acccttaata acaaacgagc ttcaatctct taacgtcata     420
gatcagaaac tgacgtcatc agaagtagta agtcaacgg ttcgataaa caacctacat     480 gatcagtcaa tggtcgtctc atcgcaacaa ggtccatggt ggttcccggc aatacaact     540 acgactaatc aaaactctgc gttttgcttt agttcaagta atactacaac ggtttcagac     600
cagatcgtat ctttaatctc ttcaatgtct acgtcatcat ctccgacacc aatgacttca     660
```

-continued

```
aacttcagtc ctgctccaaa caactgggaa caactcaact actgcaacac agtaccaagt      720
cagagcaaca gtatctacag tgccttcttt ggtaatcaat acacagaagc tagccaaacc      780
atgaacaata taatccact agtagatcaa catcatcatc atcaagacat gaagtcatgg       840
gcatcagaga ttcttcatta cacagaacac aaccaaagct cagaaactgt tatagaagca     900
gaagtgaagc cagacattgc caactactac tggagatcag catcatcatc gtcgtcacca     960
aaccaagaag ctgcaacatt actacacgat gctaacgtgg aagtgtacgg taaaaatcta    1020
caaaagctta ataacatggt gtttgatcag agcctttag                             1059
```

<210> SEQ ID NO 5
<211> LENGTH: 267
<212> TYPE: PRT
<213> ORGANISM: Arabidopsis thaliana
<220> FEATURE:
<223> OTHER INFORMATION: At5g01200 Polypeptide

<400> SEQUENCE: 5

```
Met Ser Ser Ser Thr Met Tyr Arg Gly Val Asn Met Phe Ser Pro Ala
1               5                   10                  15

Asn Thr Asn Trp Ile Phe Gln Glu Val Arg Glu Ala Thr Trp Thr Ala
            20                  25                  30

Glu Glu Asn Lys Arg Phe Glu Lys Ala Leu Ala Tyr Leu Asp Asp Lys
        35                  40                  45

Asp Asn Leu Glu Ser Trp Ser Lys Ile Ala Asp Leu Ile Pro Gly Lys
    50                  55                  60

Thr Val Ala Asp Val Ile Lys Arg Tyr Lys Glu Leu Glu Asp Asp Val
65                  70                  75                  80

Ser Asp Ile Glu Ala Gly Leu Ile Pro Ile Pro Gly Tyr Gly Gly Asp
                85                  90                  95

Ala Ser Ser Ala Ala Asn Ser Asp Tyr Phe Phe Gly Leu Glu Asn Ser
            100                 105                 110

Ser Tyr Gly Tyr Asp Tyr Val Val Gly Gly Lys Arg Ser Ser Pro Ala
        115                 120                 125

Met Thr Asp Cys Phe Arg Ser Pro Met Pro Glu Lys Glu Arg Lys Lys
    130                 135                 140

Gly Val Pro Trp Thr Glu Asp Glu His Leu Arg Phe Leu Met Gly Leu
145                 150                 155                 160

Lys Lys Tyr Gly Lys Gly Asp Trp Arg Asn Ile Ala Lys Ser Phe Val
                165                 170                 175

Thr Thr Arg Thr Pro Thr Gln Val Ala Ser His Ala Gln Lys Tyr Phe
            180                 185                 190

Leu Arg Gln Leu Thr Asp Gly Lys Asp Lys Arg Ser Ser Ile His
        195                 200                 205

Asp Ile Thr Thr Val Asn Ile Pro Asp Ala Asp Ala Ser Ala Thr Ala
    210                 215                 220

Thr Thr Ala Asp Val Ala Leu Ser Pro Thr Pro Ala Asn Ser Phe Asp
225                 230                 235                 240

Val Phe Leu Gln Pro Asn Pro His Tyr Ser Phe Ala Ser Ala Ser Ala
                245                 250                 255

Ser Ser Tyr Tyr Asn Ala Phe Pro Gln Trp Ser
            260                 265
```

<210> SEQ ID NO 6
<211> LENGTH: 804
<212> TYPE: DNA

<213> ORGANISM: Arabidopsis thaliana
<220> FEATURE:
<223> OTHER INFORMATION: At5g01200 DNA

<400> SEQUENCE: 6

```
atgtcatcgt cgacgatgta cagaggagtt aatatgtttt caccggcaaa cacaaactgg    60
attttcaag aagtcagaga agccacgtgg acggcggagg agaacaaacg gttcgagaaa   120
gctctcgctt atctggacga caaagacaat cttgagagct ggtccaagat cgcagatttg   180
attcccggca aaacagtagc tgacgtcatt aaacgataca aggagctaga ggatgatgtc   240
agcgacatcg aagccggact tatccccatt ccgggatacg cggcgacgc ctcctccgct   300
gcaaacagtg actatttctt tggtctagaa aactccagct acggttatga ttacgtcgtt   360
ggaggaaaga ggagttcgcc ggcgatgact gattgttta ggtctccgat gccggaaaag   420
gagaggaaga aaggagttcc gtggaccgag gacgaacacc tacgatttct gatgggtttg   480
aagaaatatg aaaaggaga ttggagaaac atagcaaaaa gctttgtgac gactcgaacg   540
ccgacgcaag tcgcttcaca cgctcagaaa tatttcttc acaactcac agatggtaaa   600
gacaaaagac gatcaagtat tcacgatatc accactgtta acatccctga cgcagacgca   660
tccgcaaccg ccacgaccgc tgacgtagca ctctctccta ctccagccaa ttcttttgac   720
gttttccttc agccaaatcc tcattacagt ttcgcgtctg cgtctgcgtc tagctattat   780
aatgcgtttc cgcagtggag ttaa                                          804
```

<210> SEQ ID NO 7
<211> LENGTH: 298
<212> TYPE: PRT
<213> ORGANISM: Arabidopsis thaliana
<220> FEATURE:
<223> OTHER INFORMATION: At2g38090 Polypeptide

<400> SEQUENCE: 7

```
Met Asn Arg Gly Ile Glu Val Met Ser Pro Ala Thr Tyr Leu Glu Thr
1               5                   10                  15

Ser Asn Trp Leu Phe Gln Glu Asn Arg Gly Thr Lys Trp Thr Ala Glu
            20                  25                  30

Glu Asn Lys Lys Phe Glu Asn Ala Leu Ala Phe Tyr Asp Lys Asp Thr
        35                  40                  45

Pro Asp Arg Trp Ser Arg Val Ala Ala Met Leu Pro Gly Lys Thr Val
    50                  55                  60

Gly Asp Val Ile Lys Gln Tyr Arg Glu Leu Glu Glu Asp Val Ser Asp
65                  70                  75                  80

Ile Glu Ala Gly Leu Ile Pro Ile Pro Gly Tyr Ala Ser Asp Ser Phe
                85                  90                  95

Thr Leu Asp Trp Gly Gly Tyr Asp Gly Ala Ser Gly Asn Asn Gly Phe
            100                 105                 110

Asn Met Asn Gly Tyr Tyr Phe Ser Ala Ala Gly Gly Lys Arg Gly Ser
        115                 120                 125

Ala Ala Arg Thr Ala Glu His Glu Arg Lys Lys Gly Val Pro Trp Thr
    130                 135                 140

Glu Glu Glu His Arg Gln Phe Leu Met Gly Leu Lys Lys Tyr Gly Lys
145                 150                 155                 160

Gly Asp Trp Arg Asn Ile Ala Arg Asn Phe Val Thr Arg Thr Pro
                165                 170                 175

Thr Gln Val Ala Ser His Ala Gln Lys Tyr Phe Ile Arg Gln Val Asn
            180                 185                 190
```

```
Gly Gly Lys Asp Lys Arg Arg Ser Ser Ile His Asp Ile Thr Thr Val
        195                 200                 205

Asn Ile Pro Asp Ser Pro Asp Ala Ala Ala Ala Asp Asn Ala Thr Ala
    210                 215                 220

Asn Ala Pro Cys Ser Pro Pro Ser Val Gly Gly Asn Gln Arg Glu Thr
225                 230                 235                 240

Ser Glu Trp Glu Gly Gln Thr Leu Tyr Asp Glu Thr Ala Ala Ala Phe
                245                 250                 255

Tyr Asn Gln Asn Ala Phe Ser Glu Thr Leu Leu Gly Met Ser Ser Thr
            260                 265                 270

Pro Tyr Met Ala Lys Leu Gln Glu Gln Ser Phe Leu Asn Ala Ser Gln
        275                 280                 285

Phe Glu Ser Tyr Asn Ala Tyr Leu Gln Met
        290                 295

<210> SEQ ID NO 8
<211> LENGTH: 897
<212> TYPE: DNA
<213> ORGANISM: Arabidopsis thaliana
<220> FEATURE:
<223> OTHER INFORMATION: At2g38090 DNA

<400> SEQUENCE: 8
atgaacagag gaatcgaagt tatgtcacca gcaacatatc tagagacatc aaactggttg       60
tttcaagaaa acagaggaac caaatggaca gctgaagaaa acaagaaatt cgaaaacgct      120
ttagcctttt acgacaaaga tactcccgac agatggtcca gagtcgctgc catgcttccc      180
ggtaaaacag tcggagatgt gatcaaacaa tacagagagc ttgaggaaga cgttagcgac      240
atcgaagctg tcttatacc  aatccctggt tacgcctctg attcattcac acttgattgg      300
ggtggctacg acggagcaag cggtaacaat gggtttaaca tgaacggtta ctactttcc       360 gccgccggag gaaagagagg atccgccgca cgaacggcgg agcatgagag gaagaaaggt      420
gttccatgga cagaagaaga acacagacaa tttctgatgg gtttgaagaa atatggaaaa      480
ggagattgga gaaacatagc tcgtaacttt gtgaccacaa gaacgccaac gcaagtcgca      540
agtcacgctc aaaagtattt catacggcaa gtcaatggtg gcaaagacaa acgccgttca      600
agcatccatg atatcacaac cgtcaacatc cccgactctc ctgacgctgc agccgcggat      660
aacgcaaccg caaacgcacc ttgctcgcca ccttccgtag gaggaaacca gcgggagaca      720
tcggagtggg aaggtcaaac actatacgat gaaacagcag ctgcgtttta taatcaaaac      780
gcgttttcag aaacgctact tggaatgtct tcgacgccct acatggcaaa acttcaggag      840
cagagttttc tgaacgcatc gcaattcgaa tcgtacaatg cgtatctcca aatgtag        897

<210> SEQ ID NO 9
<211> LENGTH: 288
<212> TYPE: PRT
<213> ORGANISM: Arabidopsis thaliana
<220> FEATURE:
<223> OTHER INFORMATION: At5g58900 Polypeptide

<400> SEQUENCE: 9

Met Glu Val Met Arg Pro Ser Thr Ser His Val Ser Gly Gly Asn Trp
1               5                   10                  15

Leu Met Glu Glu Thr Lys Ser Gly Val Ala Ala Ser Gly Glu Gly Ala
            20                  25                  30

Thr Trp Thr Ala Ala Glu Asn Lys Ala Phe Glu Asn Ala Leu Ala Val
```

```
         35                  40                  45
Tyr Asp Asp Asn Thr Pro Asp Arg Trp Gln Lys Val Ala Val Ile
 50                  55                  60

Pro Gly Lys Thr Val Ser Asp Val Ile Arg Gln Tyr Asn Asp Leu Glu
 65                  70                  75                  80

Ala Asp Val Ser Ser Ile Glu Ala Gly Leu Ile Pro Val Pro Gly Tyr
                 85                  90                  95

Ile Thr Ser Pro Pro Phe Thr Leu Asp Trp Ala Gly Gly Gly Gly
                100                 105                 110

Cys Asn Gly Phe Lys Pro Gly His Gln Val Cys Asn Lys Arg Ser Gln
                115                 120                 125

Ala Gly Arg Ser Pro Glu Leu Glu Arg Lys Lys Gly Val Pro Trp Thr
                130                 135                 140

Glu Glu Glu His Lys Leu Phe Leu Met Gly Leu Lys Lys Tyr Gly Lys
145                 150                 155                 160

Gly Asp Trp Arg Asn Ile Ser Arg Asn Phe Val Ile Thr Arg Thr Pro
                165                 170                 175

Thr Gln Val Ala Ser His Ala Gln Lys Tyr Phe Ile Arg Gln Leu Ser
                180                 185                 190

Gly Gly Lys Asp Lys Arg Arg Ala Ser Ile His Asp Ile Thr Thr Val
                195                 200                 205

Asn Leu Glu Glu Glu Ala Ser Leu Glu Thr Asn Lys Ser Ser Ile Val
210                 215                 220

Val Gly Asp Gln Arg Ser Arg Leu Thr Ala Phe Pro Trp Asn Gln Thr
225                 230                 235                 240

Asp Asn Asn Gly Thr Gln Ala Asp Ala Phe Asn Ile Thr Ile Gly Asn
                245                 250                 255

Ala Ile Ser Gly Val His Ser Tyr Gly Gln Val Met Ile Gly Gly Tyr
                260                 265                 270

Asn Asn Ala Asp Ser Cys Tyr Asp Ala Gln Asn Thr Met Phe Gln Leu
                275                 280                 285

<210> SEQ ID NO 10
<211> LENGTH: 867
<212> TYPE: DNA
<213> ORGANISM: Arabidopsis thaliana
<220> FEATURE:
<223> OTHER INFORMATION: At5g58900 DNA

<400> SEQUENCE: 10
atggaggtta tgagaccgtc gacgtcacac gtgtcaggtg ggaactggct catggaggaa      60
actaagagcg gcgtcgcagc ttctggtgaa ggtgccacgt ggacggcggc agagaacaag     120
gcattcgaga atgctttggc ggtttacgac gacaacactc tgatcggtg cagaaggtg      180 gctgcggtga ttccggggaa gacagtgagt gacgtaatta gacagtataa cgatttggaa     240
gctgatgtca gcagcatcga ggccggttta atcccggtcc ccggttacat cacctcgccg     300
cctttcactc tagattgggc cggcggcggt ggcggatgta acgggtttaa accgggtcat     360
caggtttgta taaacggtc gcaggccggt agatcgccgg agctggagcg aagaaaggc      420 gttccttgga cggaggaaga acacaagcta tttctaatgg gtttgaagaa atatgggaaa     480
ggagattgga gaaacatatc tcggaacttt gtgataacgc gaacgccaac acaagtagct     540
agccacgccc aaaagtactt catccggcaa ctttccggcg gcaaggacaa gacgagca      600 agcattcacg acataaccac cgtaaatctc gaagaggagg cttcctttgga gaccaataag     660
```

-continued

```
agctccattg ttgttggaga tcagcgttca aggctaaccg cgtttccttg gaaccaaacg    720
gacaacaatg aaacacaggc agacgctttc aatataacga ttggaaacgc tattagtggc    780
gttcattcat acggccaggt tatgattgga gggtataaca atgcagattc ttgctatgac    840
gcccaaaaca caatgtttca actatag                                        867
```

<210> SEQ ID NO 11
<211> LENGTH: 387
<212> TYPE: PRT
<213> ORGANISM: Arabidopsis thaliana
<220> FEATURE:
<223> OTHER INFORMATION: At3g16350 Polypeptide

<400> SEQUENCE: 11

| | | | | | | | | | | | | | | | |
|---|---|---|---|---|---|---|---|---|---|---|---|---|---|---|---|
| Met | Thr | Arg | Arg | Cys | Ser | His | Cys | Ser | Asn | Asn | Gly | His | Asn | Ser | Arg |
| 1 | | | | 5 | | | | | 10 | | | | | 15 | |
| Thr | Cys | Pro | Thr | Arg | Gly | Gly | Gly | Thr | Cys | Gly | Gly | Ser | Gly | Gly | Gly |
| | | | 20 | | | | | 25 | | | | | 30 | | |
| Gly | Gly | Gly | Gly | Gly | Gly | Gly | Ser | Gly | Ser | Ser | Ser | Ala | Val | Lys | |
| | | 35 | | | | | 40 | | | | | 45 | | | |
| Leu | Phe | Gly | Val | Arg | Leu | Thr | Asp | Gly | Ser | Ile | Ile | Lys | Lys | Ser | Ala |
| | 50 | | | | | 55 | | | | | 60 | | | | |
| Ser | Met | Gly | Asn | Leu | Ser | Ala | Leu | Ala | Val | Ala | Ala | Ala | Ala | Thr | |
| 65 | | | | | 70 | | | | | 75 | | | | | 80 |
| His | His | Arg | Leu | Ser | Pro | Ser | Pro | Leu | Ala | Thr | Ser | Asn | Leu | Asn | |
| | | | | 85 | | | | | 90 | | | | | 95 | |
| Asp | Ser | Pro | Leu | Ser | Asp | His | Ala | Arg | Tyr | Ser | Asn | Leu | His | His | Asn |
| | | | 100 | | | | | 105 | | | | | 110 | | |
| Glu | Gly | Tyr | Leu | Ser | Asp | Asp | Pro | Ala | His | Gly | Ser | Gly | Ser | Ser | His |
| | | 115 | | | | | 120 | | | | | 125 | | | |
| Arg | Arg | Gly | Glu | Arg | Lys | Arg | Gly | Val | Pro | Trp | Thr | Glu | Glu | His | |
| | 130 | | | | | 135 | | | | | 140 | | | | |
| Arg | Leu | Phe | Leu | Val | Gly | Leu | Gln | Lys | Leu | Gly | Lys | Gly | Asp | Trp | Arg |
| 145 | | | | | 150 | | | | | 155 | | | | | 160 |
| Gly | Ile | Ser | Arg | Asn | Tyr | Val | Thr | Ser | Arg | Thr | Pro | Thr | Gln | Val | Ala |
| | | | | 165 | | | | | 170 | | | | | 175 | |
| Ser | His | Ala | Gln | Lys | Tyr | Phe | Ile | Arg | His | Thr | Ser | Ser | Arg | Arg | |
| | | | 180 | | | | | 185 | | | | | 190 | | |
| Lys | Arg | Arg | Ser | Ser | Leu | Phe | Asp | Met | Val | Thr | Asp | Glu | Met | Val | Thr |
| | | 195 | | | | | 200 | | | | | 205 | | | |
| Asp | Ser | Ser | Pro | Thr | Gln | Glu | Glu | Gln | Thr | Leu | Asn | Gly | Ser | Ser | Pro |
| | 210 | | | | | 215 | | | | | 220 | | | | |
| Ser | Lys | Glu | Pro | Glu | Lys | Lys | Ser | Tyr | Leu | Pro | Ser | Leu | Glu | Leu | Ser |
| 225 | | | | | 230 | | | | | 235 | | | | | 240 |
| Leu | Asn | Asn | Thr | Thr | Glu | Ala | Glu | Glu | Val | Val | Ala | Thr | Ala | Pro | Arg |
| | | | | 245 | | | | | 250 | | | | | 255 | |
| Gln | Glu | Lys | Ser | Gln | Glu | Ala | Ile | Glu | Pro | Ser | Asn | Gly | Val | Ser | Pro |
| | | | 260 | | | | | 265 | | | | | 270 | | |
| Met | Leu | Val | Pro | Gly | Gly | Phe | Phe | Pro | Pro | Cys | Phe | Pro | Val | Thr | Tyr |
| | | 275 | | | | | 280 | | | | | 285 | | | |
| Thr | Ile | Trp | Leu | Pro | Ala | Ser | Leu | His | Gly | Thr | Glu | His | Ala | Leu | Asn |
| | 290 | | | | | 295 | | | | | 300 | | | | |
| Ala | Glu | Thr | Ser | Ser | Gln | Gln | His | Gln | Val | Leu | Lys | Pro | Lys | Pro | Gly |
| 305 | | | | | 310 | | | | | 315 | | | | | 320 |
| Phe | Ala | Lys | Glu | Arg | Val | Asn | Met | Asp | Glu | Leu | Val | Gly | Met | Ser | Gln |

```
                325                 330                 335
Leu Ser Ile Gly Met Ala Thr Arg His Glu Thr Glu Thr Ser Pro Ser
            340                 345                 350

Pro Leu Ser Leu Arg Leu Glu Pro Ser Arg Pro Ser Ala Phe His Ser
        355                 360                 365

Asn Gly Ser Val Asn Gly Ala Asp Leu Ser Lys Gly Asn Ser Ala Ile
    370                 375                 380

Gln Ala Ile
385

<210> SEQ ID NO 12
<211> LENGTH: 1164
<212> TYPE: DNA
<213> ORGANISM: Arabidopsis thaliana
<220> FEATURE:
<223> OTHER INFORMATION: At3g16350 DNA

<400> SEQUENCE: 12
atgactcgtc ggtgttcgca ttgtagcaac aatgggcaca attcacgcac gtgtccaacg      60
cgtggtggtg gcacgtgcgg tggaagtggc ggaggaggag gaggtggtgg tggaggaggg     120
tctggttcct cctccgccgt gaagttattt ggtgtgaggt taacggatgg ctcgattatt     180
aaaaagagtg cgagtatggg taatctctcg gcattggctg ttgcggcggc ggcggcaacg     240
caccaccgtt tatctccgtc gtctcctctg gcgacgtcaa atcttaatga ttcgccgtta     300
tcggatcatg cccgatactc taatttgcat cataatgaag gtatttatc tgatgatcct     360 gctcatggtt ctgggtctag tcaccgtcgt ggtgagagga agagaggtgt tccttggact     420
gaagaggaac atagactatt cttagtcggt cttcagaaac tcgggaaagg agattggcgc     480
ggtatttcga gaaactatgt aacgtcaaga actcctacac aagtggctag tcatgctcaa     540
aagtatttta ttcgacatac tagttcaagc cgcaggaaaa gacggtctag cctcttcgac     600
atggttacag atgagatggt aaccgattca tcgccaacac aggaagagca gaccttaaac     660
ggttcctctc caagcaagga acctgaaaag aaaagctacc ttccttcact tgagctctca     720
ctcaataata ccacagaagc tgaagaggtc gtagccacgg cgccacgaca ggaaaaatct     780
caagaagcta tagaaccatc aaatggtgtt tcaccaatgc tagtcccggg tggcttcttt     840
cctccttgtt ttccagtgac ttacacgatt tggctcccctg cgtcacttca cggaacagaa     900
catgccttaa acgctgagac ttcttctcag cagcatcagg tcctaaaacc aaaacctgga     960
tttgctaaag aacgtgtgaa catggacgag ttggtcggta tgtctcagct agcataggaa    1020
atggcgacaa gacacgaaac cgaaacttcc ccttccccgc tatctttgag actagagccc    1080
tcaaggccat cagcgtttca ctcgaatggc tcggttaatg gtgcagattt gagtaaaggc    1140
aacagcgcga ttcaggctat ctaa                                           1164

<210> SEQ ID NO 13
<211> LENGTH: 312
<212> TYPE: PRT
<213> ORGANISM: Oryza sativa
<220> FEATURE:
<223> OTHER INFORMATION: Os05g0543600 Polypeptide

<400> SEQUENCE: 13

Met Gly Arg Leu Ser Ser Cys Gly Gly Val Gln Ala Lys Leu Arg Lys
1               5                   10                  15

Gly Leu Trp Ser Pro Glu Glu Asp Asp Lys Leu Tyr Asn His Ile Ile
            20                  25                  30
```

```
Arg His Gly Val Gly Cys Trp Ser Ser Val Pro Lys Leu Ala Gly Leu
        35                  40                  45

Gln Arg Cys Gly Lys Ser Cys Arg Leu Arg Trp Ile Asn Tyr Leu Arg
    50                  55                  60

Pro Asp Leu Lys Arg Gly Ser Phe Ser Gln Gln Glu Glu Asp Leu Ile
65                  70                  75                  80

Val Ala Leu His Glu Ile Leu Gly Asn Arg Trp Ser Gln Ile Ala Ser
                85                  90                  95

His Leu Pro Gly Arg Thr Asp Asn Glu Ile Lys Asn Phe Trp Asn Ser
            100                 105                 110

Cys Leu Lys Lys Lys Leu Arg Gln Arg Gly Leu Asp Pro Ala Thr His
        115                 120                 125

Lys Pro Ile Ala Ala Ala Ala Ala Ala Thr Ser Ser Glu Ser Ala
    130                 135                 140

Val Thr Gln Val Asp Glu Asp His Lys Pro His Gly Ala Ala Ala Ala
145                 150                 155                 160

Ala Ala Ala Ala Asp Gly Leu Ala Ala Asn Ala Lys Gln Ser Val Phe
                165                 170                 175

Asp Pro Phe Pro Val Thr Asp Phe Gly Ala Gly Phe Asp Leu Gly Ala
            180                 185                 190

Ala Asn Met Ala Ala Ala Leu Tyr Gly Ser His Pro Asp Asp Gly Ala
        195                 200                 205

Gly Phe Val Ala Asp Tyr Ser Ser Val Leu Asp Val Ser Glu Asn Leu
    210                 215                 220

Gly Tyr Gly Glu Ser Ser Asn Ser Ser Asn Trp Thr Cys Ala Glu
225                 230                 235                 240

Val Ser Asn Val Leu Asp Ser Glu Val Leu Asn Trp Ala Ala Ser Ala
                245                 250                 255

Gly Ala Asp Ala Ala Lys Ala Glu Pro Phe Ala Asp Met Glu Gln
            260                 265                 270

Gln His Ser Gly Tyr Gly Gly Glu Tyr Gln Val Glu Asp Asp Ala Thr
        275                 280                 285

Leu Glu His Lys Phe Ser Leu Pro Cys His Gln Ser Leu Ala Gln
    290                 295                 300

Phe Asp Phe Asn Leu Glu Tyr Phe
305                 310

<210> SEQ ID NO 14
<211> LENGTH: 939
<212> TYPE: DNA
<213> ORGANISM: Oryza sativa
<220> FEATURE:
<223> OTHER INFORMATION: Os05g0543600 DNA

<400> SEQUENCE: 14
atgggacggc tgtcgtcgtg cggcggcgtg caggcgaagc tgaggaaggg gctttggtct    60
cccgaggaag acgataagct gtacaatcac atcatccgac atggcgtcgg ctgctggagc   120
tccgtcccca agctcgcagg gttgcagcga tgcggcaaga gctgcaggct gcggtggatc   180
aactacctca ggccagacct gaagcgcggg agcttctcgc agcaggagga ggacctcatc   240
gtcgcgctgc acgagatcct cgggaacagg tggtcgcaga tcgcgtcgca cttgccgggg   300
aggacggaca cgagatcaa gaacttctgg aacagctgcc tcaagaagaa gctccggcaa   360
cgcggcctcg acccggccac gcacaagccc atcgccgccg ccgccgcggc ggcgacgtcc   420
```

```
tcggagtcgg cggtcaccca ggtggatgag gatcacaagc cccacggcgc cgccgccgcc    480
gccgccgccg ccgacggcct cgccgcgaac gccaagcagt cggtgttcga cccgttcccg    540
gtgaccgact tcggcgccgg cttcgacctc ggcgcggcga acatggcggc ggcgctgtac    600
ggctcccacc ccgacgacgg cgccgggttc gtcgccgact acagcagcgt gctcgacgtg    660
tcggagaacc tgggctacgg cgagagctcc agcaacagca gcaactggac ctgcgccgag    720
gtgagcaatg tgctcgacag cgaggtgctc aactgggccg cctcggccgg cgccgacgcc    780
gccgccaagg cagagcccct cgccgacatg gagcagcagc acagtggcta tggcggcgag    840
tatcaggtgg aagacgacgc cacgctggag cacaagttct cgctaccatg ccatgagcag    900
agcttggctc aattcgactt caacttggaa tacttctga                           939
```

<210> SEQ ID NO 15
<211> LENGTH: 294
<212> TYPE: PRT
<213> ORGANISM: Oryza sativa
<220> FEATURE:
<223> OTHER INFORMATION: Os01g0142500 Polypeptide

<400> SEQUENCE: 15

```
Met Met Met Arg Asp Val Cys Met Glu Val Leu Pro Pro Met Asp His
1               5                   10                  15

Tyr Ala Ser Arg Gly Asn Trp Phe Met Ala Arg Lys Trp Ser Pro Glu
            20                  25                  30

Glu Lys Gln Phe Glu Arg Ala Leu Ala Gly Leu Asp Leu Arg Cys
        35                  40                  45

Pro Asp Trp Asp Arg Val Ala Arg Ala Ile Pro Gly Arg Ser Ala Leu
    50                  55                  60

Glu Val Met Asn His Phe Arg Asp Leu Glu Leu Asp Val Gln Gln Ile
65                  70                  75                  80

Glu Asn Gly Met Val Pro Phe Pro Val Tyr Gly Ala Ala Ala Gly
                85                  90                  95

Gly Ala Phe Thr Leu Gln Trp Asp Gly Ala His Gly Val Gly Asp Phe
            100                 105                 110

Arg Asn Ala Tyr Arg Phe Gly Gly Gly Gly Gly Lys Arg His Phe
        115                 120                 125

Gly Arg Thr Pro Glu Gln Glu Arg Lys Lys Gly Val Pro Trp Thr Glu
    130                 135                 140

Glu His Lys Leu Phe Leu Leu Gly Leu Lys Lys Tyr Gly Lys Gly
145                 150                 155                 160

Asp Trp Arg Asn Ile Ser Arg Asn Phe Val Gln Thr Arg Thr Pro Thr
                165                 170                 175

Gln Val Ala Ser His Ala Gln Lys Tyr Phe Ile Arg Leu Asn Ser Gly
            180                 185                 190

Gly Lys Asp Lys Arg Arg Ser Ser Ile His Asp Ile Thr Thr Val Asn
        195                 200                 205

Leu Thr Asp Asp Arg Pro Pro Ser Pro Ser Gln Ser Ser Leu Ile Ser
    210                 215                 220

Asn Gln Ser Asn Thr Ser Thr Leu Thr Ala Ala Val Ala Pro Phe Ser
225                 230                 235                 240

Ser Thr Ala Asp Val Lys Pro Gln Asn Ala Ala Asn Ala Ser Phe Asn
                245                 250                 255

Ser Pro Ser Arg Thr Leu Gly Met Ala Gly Tyr Gly Met Gly Leu Gln
            260                 265                 270
```

Asp Gln Gly Leu Gln Cys Gly Gly Pro Leu His Asp Gln Leu Ala Ala
          275                 280                 285

Ser Arg Ser Ile Leu Phe
    290

<210> SEQ ID NO 16
<211> LENGTH: 885
<212> TYPE: DNA
<213> ORGANISM: Oryza sativa
<220> FEATURE:
<223> OTHER INFORMATION: Os01g0142500 DNA

<400> SEQUENCE: 16

| | | |
|---|---|---|
| atgatgatga gggatgtgtg catggaggtg ctgcctccga tggaccacta cgcgtcgagg | 60 |
| gggaactggt tcatggcgcg caagtggtcg ccggaggaga caagcagtt cgagcgggcg | 120 |
| ctcgccgggc tggacctgcg gtgcccggac tgggaccggg tggcgcgcgc catcccgggc | 180 |
| aggtcggcgc tcgaggtcat gaaccacttc agggacctcg agctcgacgt ccagcagatc | 240 |
| gagaatggca tggtgcccct cccggtctac ggcgccgccg ccgccggcgg cgcgttcaca | 300 |
| ctgcagtggg atggcgccca tggcgtcggg gacttcagga acgcgtaccg gttcggcggc | 360 |
| ggcggcggcg ggaagcggca cttcggccgt acgccgagc aggagaggaa gaaaggcgtg | 420 |
| ccatggacgg aggaggagca caagttgttc ctcttaggac tgaagaaata tgggaaaggg | 480 |
| gattggagga acatatcccg caatttcgtg cagacgagga cgccgacgca ggttgccagc | 540 |
| catgcgcaga gtatttcat caggctcaac tccggtggca aggacaagag gagatccagc | 600 |
| atccatgaca ttaccacggt taacctgacg gatgaccggc tcccctcgcc atcacagtcc | 660 |
| tccttgatca gcaatcagtc caacacatca actctgaccg cagcggttgc ccccttctca | 720 |
| tcgacggccg atgtcaagcc acagaatgcc gcgaatgcgt ccttcaattc gccaagccgg | 780 |
| acacttggga tggcgggtta cgggatggga ttgcaagatc aaggattgca gtgtggtggt | 840 |
| cctctacatg atcagttggc cgcgagccga agcatattgt tttag | 885 |

<210> SEQ ID NO 17
<211> LENGTH: 299
<212> TYPE: PRT
<213> ORGANISM: Oryza sativa
<220> FEATURE:
<223> OTHER INFORMATION: Os01g0853700 Polypeptide

<400> SEQUENCE: 17

Met Met Ala Glu Ala Leu Arg Glu Val Leu Pro Leu Pro Tyr Phe Pro
1               5                   10                  15

Gly Gln Pro Cys Trp Tyr Leu Gln Glu Arg Arg Gly Ala Glu Ala Trp
            20                  25                  30

Ser Ala Glu Glu Asn Lys Val Phe Glu Arg Ala Leu Ala Gln Val Asp
        35                  40                  45

Leu Asp Ser Pro Asn Arg Trp Glu Met Val Ala Met Leu Pro Arg
    50                  55                  60

Lys Thr Val Ile Asp Val Met Asn His Tyr Arg Asp Leu Glu Asn Asp
65                  70                  75                  80

Val Gly Ser Ile Glu Ala Gly Leu Val Pro Phe Pro His Tyr Ser Ser
                85                  90                  95

Ser Leu Ser Pro Ala Ser Ser Gly Phe Thr Leu Gln Asp Trp Asp Gly
            100                 105                 110

Ser Asp Gly Gly Phe Arg Arg Gly Cys Tyr Leu Lys Arg Gly Arg Ala
        115                 120                 125

Pro Asp Gln Glu Arg Lys Lys Gly Val Pro Trp Thr Glu Glu His
    130                 135                 140

Lys Ser Phe Leu Met Gly Leu Lys Lys Tyr Gly Arg Gly Asp Trp Arg
145                 150                 155                 160

Asn Ile Ser Arg Tyr Phe Val Thr Ser Arg Thr Pro Thr Gln Val Ala
                165                 170                 175

Ser His Ala Gln Lys Tyr Phe Ile Arg Leu Asn Ser Gly Gly Lys Asp
            180                 185                 190

Lys Arg Arg Ser Ser Ile His Asp Ile Thr Thr Val Asn Leu Pro Glu
        195                 200                 205

Glu Asp Thr Ser Asn Pro Ser Pro Ser Pro Ser Val Leu Thr Thr
    210                 215                 220

Ala Ser Asp Gln Leu Gly Ser Leu Val Asp Thr Arg Pro Val Pro Pro
225                 230                 235                 240

Pro Pro Ser Leu Gly Ala Gln Arg His Phe Met Ser Pro Leu Pro Gly
                245                 250                 255

Ala Leu Gly Val Ser His His Pro Tyr Gly Asn Val Lys Leu Glu Pro
            260                 265                 270

Asn Ala Ser Phe Leu Ala Gly Gly Thr Gly Pro Gly Leu Asp Asp
        275                 280                 285

Ala Ile Leu Leu Gln Met Gln Cys Gly His Leu
    290                 295

<210> SEQ ID NO 18
<211> LENGTH: 897
<212> TYPE: DNA
<213> ORGANISM: Oryza sativa
<220> FEATURE:
<223> OTHER INFORMATION: Os01g0853700 DNA

<400> SEQUENCE: 18
atgatggcag aggcgcttcg ggaggtgcta ccgctgccct acttcccgg gcagccgtgc    60 tggtacttgc aggagcggcg aggtgcggag gcgtggtcgg cagaggagaa caaggtgttc   120
gagagggccc tcgcacaggt cgacctggac tcgccgaaca ggtgggagat ggtcgccgcg   180
atgctgccca ggaagacggt catagacgtg atgaaccact acagggacct cgagaacgac   240
gtcggctcca tcgaggcagg gctggtgccg ttccctcact acagcagcag cttgtccccg   300
gcgtcctccg ggttcaccct gcaggactgg gacggcagcg acggcgggtt caggcgcggc   360
tgctacctca acgcggccg cgccccggac caggagagga agaaaggcgt cccgtggacg   420
gaggaggagc acaagtcgtt cttgatgggg ctgaagaagt acgggagggg agactggagg   480
aacatctcgc gctacttcgt gacgagccgg acgccgacgc aggtggccag ccacgcgcag   540
aagtacttca tccgcctcaa ctccggcggc aaggacaagc gccggtctag catccacgac   600
atcaccacgg tcaacctgcc agaagaagac accagcaacc cctccccatc gccgccgtcc   660
gtgctcacca ccgcctcaga ccagctcggc tccctcgtgg acacgagacc cgttcccccg   720
ccaccgtcac tcggcgcgca acggcacttc atgtcgccgc tgccgggagc gctcggcgtc   780
agccaccacc cctacggcaa cgtgaagcta gagcccaatg cctcgttctt ggccggcggc   840
ggtacggggc ctggcctcga cgacgccatc ctcctgcaga tgcaatgcgg acacttg     897

<210> SEQ ID NO 19
<211> LENGTH: 806
<212> TYPE: PRT
<213> ORGANISM: Oryza sativa
<220> FEATURE:
<223> OTHER INFORMATION: Os04g0569100 Polypeptide

<400> SEQUENCE: 19

```
Met Gln Phe Pro Phe Ser Gly Ala Gly Pro Gly Val Phe Thr Ser Ser
1               5                   10                  15

Pro Ala Leu Ser Leu Ala Leu Ala Asp Ala Val Ala Gly Arg Asn Ser
            20                  25                  30

Gly Gly Gly Gly Lys Met Val Thr Ala Ala His Gly Val Gly Gly
        35                  40                  45

Gly Gly Gly Gly Arg Ala Lys Ala Arg Asp Ala Leu Glu Val Glu
    50                  55                  60

Asn Glu Met Ser Arg Ser Gly Ser Asp His Leu Asp Val Val Ser Cys
65                  70                  75                  80

Gly Asp Ala Gly Gly Gly Gly Asp Asp Asp Asp Glu Asp Ala
                85                  90                  95

Glu His Gly Asn Pro Pro Lys Arg Lys Lys Arg Tyr His Arg His Thr
            100                 105                 110

Pro Gln Gln Ile Gln Glu Leu Glu Ala Met Phe Lys Glu Cys Pro His
        115                 120                 125

Pro Asp Glu Lys Gln Arg Ala Glu Leu Ser Lys Arg Leu Gly Leu Glu
    130                 135                 140

Pro Arg Gln Val Lys Phe Trp Phe Gln Asn Arg Arg Thr Gln Met Lys
145                 150                 155                 160

Met Gln Leu Glu Arg His Glu Asn Ser Leu Leu Lys Gln Glu Asn Asp
                165                 170                 175

Lys Leu Arg Ser Glu Asn Leu Ser Ile Arg Glu Ala Thr Ser Asn Ala
            180                 185                 190

Val Cys Val Gly Cys Gly Gly Pro Ala Met Leu Gly Val Ser Leu
        195                 200                 205

Glu Glu His His Leu Arg Val Glu Asn Ala Arg Leu Lys Asp Glu Leu
    210                 215                 220

Ser Arg Val Cys Ala Leu Ala Ala Lys Phe Leu Gly Lys Ser Ile Ser
225                 230                 235                 240

Val Met Ala Pro Pro Gln Met His Gln Pro His Pro Val Pro Gly Ser
                245                 250                 255

Ser Leu Glu Leu Ala Val Gly Gly Ile Gly Ser Met Pro Ser Ala Thr
            260                 265                 270

Met Pro Ile Ser Thr Ile Thr Asp Phe Ala Gly Ala Met Ser Ser Ser
        275                 280                 285

Met Gly Thr Val Ile Thr Pro Met Lys Ser Glu Ala Glu Pro Ser Ala
    290                 295                 300

Met Ala Gly Ile Asp Lys Ser Leu Phe Leu Glu Leu Ala Met Ser Ala
305                 310                 315                 320

Met Asp Glu Leu Val Lys Met Ala Gln Met Gly Asp Pro Leu Trp Ile
                325                 330                 335

Pro Gly Ala Ser Val Pro Ser Ser Pro Ala Lys Lys Ser Leu Asn Phe
            340                 345                 350

Glu Glu Tyr Leu Asn Thr Phe Pro Pro Cys Ile Gly Val Lys Pro Glu
        355                 360                 365

Gly Tyr Val Ser Glu Ala Ser Arg Glu Ser Gly Ile Val Ile Ile Asp
    370                 375                 380

Asp Gly Ala Ala Leu Val Glu Thr Leu Met Asp Glu Arg Arg Trp Ser
385                 390                 395                 400
```

```
Asp Met Phe Ser Cys Met Ile Ala Lys Ala Ser Thr Glu Glu Ile
            405                 410                 415

Ser Thr Gly Val Ala Gly Ser Arg Asn Gly Ala Leu Leu Met Gln
            420                 425                 430

Ala Glu Leu Gln Val Leu Ser Pro Leu Val Pro Ile Arg Glu Val Lys
            435                 440                 445

Phe Leu Arg Phe Ser Lys Gln Leu Ala Asp Gly Val Trp Ala Val
            450                 455                 460

Asp Val Ser Ala Asp Glu Leu Met Arg Asp Gln Gly Ile Thr Ser Ala
465                 470                 475                 480

Ser Ser Thr Ala Asn Met Asn Cys Arg Arg Leu Pro Ser Gly Cys Val
            485                 490                 495

Leu Gln Asp Thr Pro Asn Gly Phe Val Lys Val Thr Trp Val Glu His
            500                 505                 510

Thr Glu Tyr Asp Glu Ala Ser Val His Pro Leu Tyr Arg Pro Leu Leu
            515                 520                 525

Arg Ser Gly Leu Ala Leu Gly Ala Gly Arg Trp Ile Ala Thr Leu Gln
            530                 535                 540

Arg Gln Cys Glu Cys Leu Ala Leu Leu Met Ser Ser Ile Ala Leu Pro
545                 550                 555                 560

Glu Asn Asp Ser Ser Ala Ile His Pro Glu Gly Lys Arg Ser Met Leu
            565                 570                 575

Lys Leu Ala Arg Arg Met Thr Asp Asn Phe Cys Ala Gly Val Ser Thr
            580                 585                 590

Ser Ser Thr Arg Glu Trp Ser Lys Leu Val Gly Leu Thr Gly Asn Ile
            595                 600                 605

Gly Glu Asp Val His Val Met Ala Arg Lys Ser Val Asp Glu Pro Gly
            610                 615                 620

Thr Pro Pro Gly Val Val Leu Ser Ala Ala Thr Ser Val Trp Met Pro
625                 630                 635                 640

Val Met Pro Glu Arg Leu Phe Asn Phe Leu His Asn Lys Gly Leu Arg
            645                 650                 655

Ala Glu Trp Asp Ile Leu Ser Asn Gly Gly Pro Met Gln Glu Val Thr
            660                 665                 670

Ser Ile Ala Lys Gly Gln Gln Asn Gly Asn Thr Val Cys Leu Leu Lys
            675                 680                 685

Ala Ser Pro Thr Lys Asp Lys Gln Asn Ser Met Leu Ile Leu Gln Glu
            690                 695                 700

Thr Cys Ala Asp Ala Ser Gly Ser Met Val Val Tyr Ala Pro Val Asp
705                 710                 715                 720

Ile Pro Ala Met His Leu Val Met Ser Gly Gly Asp Ser Ser Cys Val
            725                 730                 735

Ala Leu Leu Pro Ser Gly Phe Ala Ile Leu Pro Ala Gly Pro Ser Ile
            740                 745                 750

Gly Ala Asp His Lys Met Gly Gly Ser Leu Leu Thr Val Ala Phe Gln
            755                 760                 765

Ile Leu Ala Asn Ser Gln Pro Ser Ala Lys Leu Thr Val Glu Ser Val
            770                 775                 780

Glu Thr Val Ser Asn Leu Ile Ser Cys Thr Ile Lys Lys Ile Lys Thr
785                 790                 795                 800

Ala Leu His Cys Asp Val
            805
```

<210> SEQ ID NO 20
<211> LENGTH: 2418
<212> TYPE: DNA
<213> ORGANISM: Oryza sativa
<220> FEATURE:
<223> OTHER INFORMATION: Os04g0569100 DNA

<400> SEQUENCE: 20

| | | | | | |
|---|---|---|---|---|---|
| atgcagttcc | cgttctccgg | cgctggcccg | ggcgtcttca | cgtcatcgcc | ggcgctctcc | 60 |
| ctcgcgctgg | ctgacgcggt | ggcaggccgg | aacagcggcg | gcggtgggaa | gatggttacc | 120 |
| gcggcccatg | gcggcgtcgg | cggaggagga | ggaggaggac | gcgcgaaggc | gagggacgcg | 180 |
| ttggaggtgg | agaacgagat | gagccggtcc | gggagcgacc | acctcgacgt | cgtctcttgc | 240 |
| ggcgacgcgg | gcgcggcgg | cggcgacgac | gacgatgacg | aggacgccga | gcacggcaac | 300 |
| ccgcccaagc | gcaagaagcg | gtaccaccgc | cacacgccgc | agcagatcca | agagctggaa | 360 |
| gcgatgttca | aggaatgccc | ccacccagac | gagaagcagc | gcgccgagct | gagcaagcgg | 420 |
| ctcggcctcg | aaccccggca | ggtcaagttc | tggttccaga | tcggcgaac | gcagatgaag | 480 |
| atgcaactgg | agcgacacga | gaactcgctg | ctgaagcagg | agaacgataa | gctgcggtcc | 540 |
| gagaacctgt | caatccggga | ggccacgagc | aacgcggtgt | gcgttggctg | cggcggcccg | 600 |
| gcgatgctcg | gggaggtgtc | cctggaggag | caccaccttc | gcgtcgagaa | cgcgaggctc | 660 |
| aaggacgagc | tcagccgagt | gtgcgcgctc | gccgccaagt | tccttggcaa | gtccatctct | 720 |
| gtcatggcgc | caccgcagat | gcatcagcct | catcctgtgc | caggctcgtc | gctggagctt | 780 |
| gcggttgggg | gtatcggttc | gatgccatca | gccacgatgc | ccatctcgac | gatcactgat | 840 |
| tttgctggcg | ccatgtccag | ttcaatgggc | acggtgatca | cgcccatgaa | gtctgaggct | 900 |
| gaaccatcgg | caatgctgg | cattgacaag | tccttgttct | ggagctagc | aatgagtgca | 960 |
| atggatgagc | tagtcaagat | ggctcagatg | ggggatccgc | tatggattcc | aggtgcctcc | 1020 |
| gtaccttcct | cgccggcaaa | gaagagtcta | aacttcgagg | agtacctaaa | cacctttcca | 1080 |
| ccttgcatcg | gggtgaagcc | tgaagggtat | gtatcagagg | catctagaga | atctggcatt | 1140 |
| gtcatcattg | acgatggcgc | cgcgcttgtg | gagacccctca | tggatgagcg | acggtggtcc | 1200 |
| gatatgttct | catgcatgat | tgccaaggca | tcaaccactg | aggagatttc | tactggtgtt | 1260 |
| gctgggagta | gaaatggtgc | attgcttctt | atgcaggcag | agctacaggt | gctttctcct | 1320 |
| cttgtgccta | ttagagaggt | gaagtttctc | aggttctcca | aacagctggc | tgatggtgta | 1380 |
| tgggctgtag | tggacgtttc | ggctgatgaa | ttgatgaggg | atcagggcat | tacttctgca | 1440 |
| tcctcgactg | caaacatgaa | ctgccgaagg | ctgccttctg | gttgtgtgct | gcaggacact | 1500 |
| ccaaatgggt | tgttaaggt | cacatggggtt | gaacatacag | aatatgatga | ggcatctgtg | 1560 |
| cacccgctct | accggcctct | tctccggtct | ggtcttgccc | ttggtgcagg | gcgatggatc | 1620 |
| gcgacattac | agcggcagtg | cgaatgcttg | gcccttctca | tgtcttctat | tgcattgcca | 1680 |
| gagaacgact | catcagctat | ccatcctgaa | ggtaaacgga | gcatgttgaa | gttggcaagg | 1740 |
| aggatgacgg | acaacttctg | tgcaggggtg | agcacatcat | ctacccgtga | atggagcaaa | 1800 |
| ctggttggat | tgacaggcaa | cattgggag | atgtgcatg | taatggcgcg | aagagtgtg | 1860 |
| gatgaacctg | gaacgccgcc | aggtgtggtg | cttagtgctg | ctacatctgt | gtggatgcct | 1920 |
| gtgatgcctg | aacggctctt | caacttcttg | cacaacaagg | ggctgcgtgc | tgaatgggat | 1980 |
| atcctcagca | atggtggccc | tatgcaggag | gtgacaagca | ttgccaaggg | gcaacagaat | 2040 |
| ggcaataccg | tatgtctact | gaaggctagt | cccaccaaag | acaagcagaa | cagcatgctg | 2100 |

```
atcctacagg agacgtgtgc agacgcatcc ggttcaatgg ttgtgtatgc tcctgtagac    2160
atcccagcaa tgcaccttgt catgagtggt ggggattcgt catgcgtcgc ccttcttcca    2220
tcaggttttg ccatcctgcc tgctgggcct agcatcggcg cagatcacaa gatgggcggt    2280
tcattgctca ccgttgcatt ccagatactt gccaacagcc agcccagtgc taagctcacg    2340
gtggagtcag tcgagaccgt gagcaacctt atctcctgca ccatcaagaa gatcaagacg    2400
gcgctgcatt gcgacgtg                                                  2418
```

<210> SEQ ID NO 21
<211> LENGTH: 10
<212> TYPE: PRT
<213> ORGANISM: Arabidopsis thaliana
<220> FEATURE:
<223> OTHER INFORMATION: SRDX(SUPERMAN) Polypeptide

<400> SEQUENCE: 21

Leu Asp Leu Glu Leu Arg Leu Gly Phe Ala
1               5                   10

<210> SEQ ID NO 22
<211> LENGTH: 36
<212> TYPE: DNA
<213> ORGANISM: Arabidopsis thaliana
<220> FEATURE:
<223> OTHER INFORMATION: SRDX(SUPERMAN) DNA

<400> SEQUENCE: 22
gatctggatc tagaactccg tttgggtttc gcttaa                               36

<210> SEQ ID NO 23
<211> LENGTH: 8
<212> TYPE: PRT
<213> ORGANISM: Arabidopsis thaliana
<220> FEATURE:
<223> OTHER INFORMATION: BRD(At2g36080) Polypeptide

<400> SEQUENCE: 23

Leu Arg Leu Phe Gly Val Asn Met
1               5

<210> SEQ ID NO 24
<211> LENGTH: 25
<212> TYPE: DNA
<213> ORGANISM: Arabidopsis thaliana
<220> FEATURE:
<223> OTHER INFORMATION: BRD(At2g36080) DNA

<400> SEQUENCE: 24
attaagactg ttcggagtga acatg                                           25

<210> SEQ ID NO 25
<211> LENGTH: 8
<212> TYPE: PRT
<213> ORGANISM: Arabidopsis thaliana
<220> FEATURE:
<223> OTHER INFORMATION: WUS-box(WUSCHEL) Polypeptide

<400> SEQUENCE: 25

Thr Leu Pro Leu Phe Pro Met His
1               5

<210> SEQ ID NO 26
<211> LENGTH: 24

```
<212> TYPE: DNA
<213> ORGANISM: Arabidopsis thaliana
<220> FEATURE:
<223> OTHER INFORMATION: WUS-box(WUSCHEL) DNA

<400> SEQUENCE: 26
acgcttcctc tcttccctat gcac                                              24

<210> SEQ ID NO 27
<211> LENGTH: 6
<212> TYPE: PRT
<213> ORGANISM: Arabidopsis thaliana
<220> FEATURE:
<223> OTHER INFORMATION: L2R(AtMYBL2) Polypeptide

<400> SEQUENCE: 27

Thr Leu Leu Leu Phe Arg
1               5

<210> SEQ ID NO 28
<211> LENGTH: 18
<212> TYPE: DNA
<213> ORGANISM: Arabidopsis thaliana
<220> FEATURE:
<223> OTHER INFORMATION: L2R(AtMYBL2) DNA

<400> SEQUENCE: 28
acgcttcttc tattccga                                                     18

<210> SEQ ID NO 29
<211> LENGTH: 865
<212> TYPE: DNA
<213> ORGANISM: Cauliflower mosaic virus
<220> FEATURE:
<223> OTHER INFORMATION: CaMV35S Promoter DNA

<400> SEQUENCE: 29
gcatgcctgc aggtccccag attagccttt tcaatttcag aaagaatgct aacccacaga       60
tggttagaga ggcttacgca gcaggtctca tcaagacgat ctacccgagc aataatctcc      120
aggaaatcaa ataccttccc aagaaggtta agatgcagt caaagattc aggactaact       180 gcatcaagaa cacagagaaa gatatatttc tcaagatcag aagtactatt ccagtatgga      240
cgattcaagg cttgcttcac aaaccaaggc aagtaataga gattggagtc tctaaaaagg      300
tagttcccac tgaatcaaag gccatggagt caaagattca atagaggac ctaacagaac       360 tcgccgtaaa gactggcgaa cagttcatac agagtctctt acgactcaat gacaagaaga      420
aaatcttcgt caacatggtg gagcacgaca cacttgtcta ctccaaaaat atcaaagata      480
cagtctcaga agaccaaagg gcaattgaga cttttcaaca agggtaata tccggaaacc       540 tcctcggatt ccattgccca gctatctgtc actttattgt gaagatagtg gaaaggaag       600 gtggctccta caaatgccat cattgcgata aaggaaaggc catcgttgaa gatgcctctg      660
ccgacagtgg tcccaaagat ggaccccac ccacgaggag catcgtggaa aaagaagacg       720
ttccaaccac gtcttcaaag caagtggatt gatgtgatat ctccactgac gtaagggatg      780
acgcacaatc ccactatcct tcgcaagacc cttcctctat ataaggaagt tcatttcatt      840
tggagaggac acggggact ctaga                                              865

<210> SEQ ID NO 30
<211> LENGTH: 3144
<212> TYPE: DNA
<213> ORGANISM: Arabidopsis thaliana
```

<220> FEATURE:
<223> OTHER INFORMATION: At5g07260 Promoter DNA

<400> SEQUENCE: 30

```
ccaacatgat ggagtgattt gtatgtttga aatgaaaagc agattggtat taaccttgtt      60
agagtagatt gtccagttgg tgaaaagttc agagagcatt gagccaagga ggccaaaaag     120
agcaccagaa gctccaacag agatactgtt tctgataaac aacgacgaca atacactccc     180
tccaattcct gataataggt atataactcc gattctaact gaaaatttca agaaaccaag     240
attcagattt ctagcaacag aataacacaa ctagaagaat gaagactaaa tccacccaaa     300
ttgcatacca aaaccaaatt gctgctcgag acgaatacca atgaaaacaa ggcttaacat     360
attggctccg agatgaataa cacccgcgtg taaccatata catgtcaaga gacgccaacc     420
ttccttcttc tccacaactt tgctccactc aagtgctcct aacttctcca atcttcaagt     480
atatatcaac caaaacacaa tcatatcaaa atcttgtatc tcaaactctc aatcacataa     540
cttcatcatt tcaacatctc aagatccagt aaatttcgat ttagtaaccg acaaacttga     600
gaaacagaac caaaacgtga ttctctagta tttagaaccc taaatcaaca tcgatacaaa     660
atttagaaaa cgtacgtgtg agaagatgga ccaaagagag gattagttcg gagaggctca     720
aaggagagtc taccgagaaa cttggcgaca cagtgacctc tgagacggtg agactcgaaa     780
tgattcggac agttattaac gaacatcgcc acgacgaaaa ccgcaacgtt agccacaacg     840
aacatcggaa caagccacga cgtccaccgc gacgacaacg cgttatcgcc aaattcagta     900
gacgacgaca aggctaccgg cagaggcggt ggtccgattc gattccgatc accgcctctg     960
cttccgattc ctcgatcttt cgccgacatt ctgttctcca gatcatcatc tccgacagcc    1020
atagtgatct ctctcttctc tgtctgtaat ttgtttattg ttttttttgt tttggttggt    1080
ttttttttt ttttggattg aaggcggtaa gaagagttaa accttgagag tgggtgagaa    1140
agtgggtttc tgttaaccaa ttaaatcttt ccacgtgtaa atgtataata ccggtttttg    1200
tggtacgtgt tacggtgtac cgtggtctat tgcacactgt atcgtaacgg agctaacgtg    1260
cgctggattt ccaaatttgc tttaagagca tctccatcgg caaaagtggt agagagtatc    1320
tcaaaaaata aataattaat attttaatta aattaatata ttttaattag tttaaagtaa    1380
atgaaccatt aattgaatga caattctgaa taaatgctca gaatcttctt tcttgccaga    1440
aacatttctc cacttttctc tcttctttca tattttttct cttttaattt attatttaat    1500
tgatgagtat ctcaatcaga tactccgata gtataaagct gtgatgtatg atactttgct    1560
cttgtttcct ttgtctttgg gggttcttaa gaaagtttcg ttggctcgtg taaatgtcta    1620
aacttctgga cttgataccc tatcaattaa taatatcgga aaaacaacat atatttgtta    1680
tgttgaggac tctctaacgt ttaaattaat atgaacaaca ttattaaatg aataatcggg    1740
ttccgaaaat atagtaatga gtaaagtttt aggtcttagt cgaaaatcgt tgaagaccta    1800
atatgatatt tggtggaatg atatcaaaga gatttttttc cggaagagat gattataatg    1860
ttttattcga atgtgtggac cattaggaat attagtttag agatatagaa tgttatttgt    1920
gggagatggg taaatcccct cttagaaaaa ggatcataat aaccatgccg gtaatatgtg    1980
tcttattgat cgtggaataa atgtatggaa ttgcatggtg gatcaagatg tggtcaccgc    2040
gtaccaagcg catcttgata tttgttttaa aagatttttcg tcgcttcttc ttaaggtata    2100
tattgaacgt taaagttaaa cttaggatgc tagtcgagat gaccataatg aaatctctag    2160
acttatttaa tccagttgaa aactcatcac ataatagttg tcgtatgaca ttttcgaaac    2220
```

| | |
|---|---|
| attgttcctt tgggtttagt gttgatgtag cagctagagg tgtgccatta ctctttgaat | 2280 |
| gcctacggaa cactcatacg atgttatatg gtctgtggtc acacagagta gatggaaact | 2340 |
| atcttatgtg tgatgtgccg tcttaatcta ttaaagggcc tttggtaaaa ccaaaataaa | 2400 |
| ttaaccttt tactaaaaaa ctttttttt ctaaaatttg ggatcatttt ctttactaat | 2460 |
| atttttttag aatgactttg caccctttggc aaatatctat gttgtctaaa ggtagagacg | 2520 |
| gataaatgga cacgaggacc ggaaaagatg gcttaatctt tcggaagttt agagctacat | 2580 |
| ctttaacttt gttttggttt catgtcaacg tatcatacat agataggttg taaaaaagcg | 2640 |
| ttacgagaat aagtattttc tgaataaccg taacgccttt ttatatatct ttaagaataa | 2700 |
| aaaagtcatt aactacaaaa taagaaggaa atttattggc agagaatcca ctttgaatta | 2760 |
| caataaataa tgatgaacat tgtctcatt ttagtcaaaa aaatatgaat ctcgtgagcc | 2820 |
| tttcatttat taacctacac ataatagttt ttcttgttta tatatatata tggttaatgg | 2880 |
| ttttcagaga atgaatactc agtcactcat aactagcaga agtttttct ctacagattc | 2940 |
| atcgtttgag gagttctgtg agtttatcaa ggtaggtatg gttcttaaa tcttcgacta | 3000 |
| aagtttcaat tcttttcaat ttaggttttc tgttaaacaa acgaggtttt attttttaaa | 3060 |
| caacatatca caaattcaca atagttgttt aacttttttg tttttttgttt ttttctatga | 3120 |
| ctataacaca tgaaaaggtc agat | 3144 |

<210> SEQ ID NO 31
<211> LENGTH: 3130
<212> TYPE: DNA
<213> ORGANISM: Arabidopsis thaliana
<220> FEATURE:
<223> OTHER INFORMATION: At5g26660 Promoter DNA

<400> SEQUENCE: 31

| | |
|---|---|
| cactactttc gtatagtatt gcttctctaa gcaagctttt tttgtactta gaacaaggaa | 60 |
| atttataatt tcttgtgacc aaatcatgaa aattctgttt tgtcccact tttgcaatca | 120 |
| tcattctact acaaaatgat gctctcttac tttagtttcg ccctctttta ttcgtcctca | 180 |
| tttttccctt tcattgacgt cgtttgtttg ttttttacta actatttta tgagttttcg | 240 |
| aaaacaagta actaattcat tgacatgcat gttatttttg aatgttatttt actttaatag | 300 |
| tagtacatta ttaacaatta aattaagaaa taaggtacaa gtcaacatgc attgttaagt | 360 |
| aaattatttt ctccctctct cactttaac cttaaaactg caacaatgat ttaaacaaag | 420 |
| aacataaact ttaggacaaa caatcatagg tttaaaatac atgaaatatc attgatcgat | 480 |
| gaactttctt aaaatcttta aggacgctct aaccctcgga agaaaggga gtttaccacc | 540 |
| ctttcccaac ctccacgtcc acttatccaa tctggttgat cagcgtgtat ccaaacatta | 600 |
| gatcatacgg aacaactcaa cactatctag taatatattt tttctaaagt ttatgatcaa | 660 |
| ttataaccca aagagttacg gatacaaatc ctagtatttt gatacattat tgtcaatgat | 720 |
| aatttgcata taaatgcatt gcattgagtc tacaacgtaa ctactttttc ctcctaacaa | 780 |
| aatgcatgat taatttacag ctcatttcta gtaatggcac caatttgaac gatattagcc | 840 |
| aaaccattgg accaaattga tggccaagca tttgatctac ttttgtcttt tcttggtttt | 900 |
| ttatagctat tgatctttca ccacttcgtt catttcgaaa aatagtcctc tcaacaggac | 960 |
| cttggaagag gcaagtccta ctctcatgaa catggcttct cgaagataaa accaaagtca | 1020 |
| atgtcaacct ctctccaact tgaaaatttt aaatgctcaa tcatttgaaa ggcggcgaat | 1080 |
| tcttttgtat ttcccattac aaactataca aaaacatcac cgtgactata aattttcta | 1140 |

```
tgcacataaa aacatttaac ttatgccaat atatactttt tagttttttac aaccaatttt    1200 agtccacttt cgactacgca aagatgattt tataaaactt gaaaatgaca gaattaagag    1260
gttggcatcg gctaattgat tgcatgttat aaaaatataa ctggatgact ttctcattac    1320
agtttttttt atcgacggct aattcgattt tatccactgc atttagtttc ttataagttc    1380
tttactgcat atatatatac gtaatatatg tatattataa ttttttcttc ttcctctact    1440
cgtcctaata attttgatga aatggttttg tatttaaaaa atatactaat tatattttca    1500
ggatacaacg acatttgggt agtgtaaatg caaaatacca aaacaaatat atactatatg    1560
ttatacaaaa attgttttaaa catgtaaaaa atgatatgca taagacaaaa tcccatttta    1620
attgaaaata taatatatca ttcgtgacgc agctgacgct attattaaaa ttgaggtgat    1680
gatctatgag atttttttcct cttacaacaa atatgtcaaa ggagacaagc cagttgtata    1740
tacaagggat tgagtgtttt ttccgttgta atgatattct tcaattatgc tattgtttgt    1800
atgatttctt aagactcgac ttaagctagt agctttatat aaataaaata gctttgttgt    1860
aaactaatca tcatgaaatt tcaaataaca aaaaaaaact aatcatcatg attgtattttt    1920 taaaaaggaa actctctttc ctataatacg ataataatga gaacgcatct cctatcataa    1980
tatacgtttc taaacactta ttgttgttct cgtgtagaag catgctcgaa attaatcaaa    2040
attatctttg ttttttgtttt gtttcacgtt agactagcct catcgatgta agattaatga    2100
aagattaccc gttacaagtc ggtaactagt aacattagtg tgtatataaa taagaatatt    2160
agtggttacg cgaccaaatt attgcatagt ggaaacattt aaggctattt ttccaccatt    2220
actttgcgta cttgaattga agaactcttt acattctcag cacatcaagg tgtctccttt    2280
gagatcaaaa aagtaggaaa aataaaacga aaaagtacta taaatattaa tttcgtttac    2340
gaacaaaaaa gtattaaaat tccgtagaca ttttttggggg gacaataatt ttagactcgt    2400
acaatgcttt catggaaatg agtttgttgt tgaccgatgg cttccctttta ttttttcttttc    2460 cactttttta ttactaatta ggaaactagt aatatttata ctcgatgtat aattcactaa    2520
tcatatactt tccaaaacgt agcaaataat tcgactagaa tatattgtcc gtgaattaag    2580
tttcctcttt tctttttttta tgttaaccat catgtttctg ttatttgttg attttaataa    2640
ccatactatt ttatactttt ttaaaaataa ttgaaaataa attcagatta caagtctacg    2700
ataatgattc ttcttctttt tcattgtaga taaatttctt aaaagttgac tacttttctg    2760
tcagtatatg tcacattttt ctatctatcg ttcgagaaaa aaaaagaaa aaaaaaagtt    2820 tacaagtgtt acctctaaag tcttaaccac catttctttc tatttttgtaa aggaatcaaa    2880 tagttattta ctatgtttga gttcatctct tgagttttct gaataaggtg gtcccataaa    2940
aggtatcaat taattcaccc aacgattata aaacaaagt gtttacacca gaatatcgcc    3000
aatcatagtt tctctcattt tataataatt ttctccatct tcttccttcc tcttcaagct    3060
tatagaacct ccaagaacca taaaactctc tctgcaacaa tctatacttt cttcattact    3120
tttataaaaa                                                          3130
```

<210> SEQ ID NO 32
<211> LENGTH: 2321
<212> TYPE: DNA
<213> ORGANISM: Arabidopsis thaliana
<220> FEATURE:
<223> OTHER INFORMATION: At5g01200 Promoter DNA

<400> SEQUENCE: 32

```
ttcggacttc tgattgatcc atagtttgtc ctaatttgtt tttatcactt gtttaataca        60
tgtggtagat aataaaaaat gttcaaaacg caataccata cttgaaaaaa aaaaatgtta       120
gacctagtta taagacaaga ctgaactaat taagtgatcg gttagttggt aaaacaaaat       180
agtatttcga acttaatttt cacctaaagt ttaaacgtgt ctactaatga ctcgataaac       240
taaaaaaaac agtctttttt ttcttccaaa aagtcgttat caaagcagaa ttcatctgtc       300
gtcgaatttt gaatgagtag gtgcaatgtc acatttccaa tattaaaaga aaacgagaaa       360
gaaaaaaaca aaatactcct cataaaacga tagaaatgaa ataaaacgaa gcaagagtaa       420
taaattcgac agaaaaagga gtaatttact aattatagta agagaatctt gctaaatata       480
gaatccaaga agaagtcact ctctgtggaa cagaaacctt gtgtctgcta caaatcagca       540
gatgacactt acagtttacg tttcatcatg catgtgagcg acactatagg gagaattcgg       600
tattggcttc ctttgttgtc cctaccttat ttaattactc ctgataacta ttttctgtg        660 tatttcatcg tatcgaaata tccaaatttc attcttcatg gctgatttaa ctagtgttta       720
attataatta tactttatac tttttttttgg ttcttaatca cacatgcttt cgggatcttg      780
aatacgaaat tttaaaccgt ctatcatttg tttcctgaac cgggtattgc aaatagttaa       840
atcttagtca actatttttt cgagttttttt ttaaaaatag ttctgaaaga caaaaataca     900
tgagtttgtg aaaatgtttg acagttggct ataataattg gttgcaatgc tttatacttt       960
taccaaattt aaattattca attggctaga agtggagctg tggtaccgtc cacatgaggt      1020
ggtgtcgtgg tgagacatta atatatgaac ttttgttacg atatgaaagc acccgacaca      1080
tacattcttc gtattatctt gccttatatg aataaacata aaataaccaa tactaaatt       1140 gaaactgtga tacactaaag aaaatatctt tggttacatc cagctctggc ttctgttcaa      1200 agttttttctt ttgaatttat ttaaaggtta attaagatca ccacctaacc cacttgtaca    1260
acggttctgc agttttttgcc atcgaatccc attgtttaat tcgcatattt gtatgatctc    1320 tactttttttt ttaaagttaa atagattaat taacaaaatg aagtttattt acaacaaaat   1380
aaatgaaaag tacaaatacg ttaaaaaaca aattgtttgc cagccaaaaa ttaattaaat       1440
acgtaatttt cgaaggtgta atattccaac ttgttttttgt atatttgttt agcttatgga    1500
gttatggttg tgttattata tattgaatgg gctatttcgt gttgacaaat aagctcttta      1560
gttaaatatt attatgttct tgattaaaca acaaattaag aaccggccaa accattgaac      1620
agtcgttttc tggtcttttt catttttattg gttacacctt ctttgtcata aaatagaaat    1680
tatgttatac tttctttcat gtatcgacac gtgcatttgg ttagtcttaa tcccatttca     1740 atttatatg atttatcata ttagcagaaa acaaatatgc taattatcac atagataagc       1800
catactaaaa gtatttatct gaccttaggt taaaaaaaat attaaaatat agcttataag      1860
aaacattcac tactgagttg tcatatttct actggccgac ttagattgca acaactaaaa     1920 tatattttttt ataaatcatt tgacataggc aaaacaaaaa caaatatctc tgtaactttt    1980
tcctcaattt tttcttttaa aaaaacactt ttttatacac cttttcctgt tgaatgtatt    2040
attattccta ttgatcatca cgtgaaatat agaaaaataa aataaaaaag caaaatccac      2100
ttttgtgttt tccttttcgt ttacgaccaa agagatccac tttatgctct cttcattttc     2160
tccatgtaat aatttttctc gagagatttc tgaaataaa gtcgtttctt tttttttttg    2220
ccttggtcac tcaagactct cttcttcact ctctgttttt tgtcctcttc taaaatttag    2280
agaaaaaaac gaaagttttc accaaaaaca gaggaggagc t                         2321
```

<210> SEQ ID NO 33
<211> LENGTH: 3266
<212> TYPE: DNA
<213> ORGANISM: Arabidopsis thaliana
<220> FEATURE:
<223> OTHER INFORMATION: At2g38090 Promoter DNA

<400> SEQUENCE: 33

| | | | | | |
|---|---|---|---|---|---|
| aaatttatg | cataaaatat | tttgagacga | aatatttcta | taattagaaa | agtctaaaat | 60 |
| ttctaatggt | tttactatag | aaaatattcc | aaaaatttat | atatacaatc | taaatttaaa | 120 |
| tttgttcatc | cattgtgaac | ttttgataaa | ttttactaaa | attttagcat | tggtaacata | 180 |
| ctttattgaa | gtttttattt | tgcatctgat | aatcttcgaa | atacataaaa | acaatgtctt | 240 |
| ataattattc | aactattttc | tgccacccat | tttgttgagg | gcactgtgta | aaccacattt | 300 |
| attttgaatt | tgacattcgt | ttttattata | tttcttagtt | ttgtaaccaa | aatatatatt | 360 |
| ttattataaa | agggtaaatc | ttgaactgat | ccaaatcaga | ctaatatttc | agtctgtagt | 420 |
| ataccatgtt | tctagctaca | caatatatat | atacagctac | aaacatggaa | acagaggaaa | 480 |
| aaactcatct | cgtctcatat | tagatcaaca | tggtgaattc | tcaactgcga | tatattaata | 540 |
| acaataaaaa | ttcttaacac | tttcaagaat | tattgtgtct | gttatggcgt | gatcacttaa | 600 |
| gctacctaac | ccatttataa | ataaatcatg | acagtttatt | tgttttaaga | aatccattag | 660 |
| tgtaatttac | aaagaaaagt | aagcgtggtc | ccaagatacg | agtctatgag | gaacatctga | 720 |
| aggattaatt | agcatttcag | tatgtattta | atttacgttt | tgtgtgattg | ccgttcataa | 780 |
| tgtgtttcga | atatacatta | atcttatagt | agtaaactat | acataaatta | aattagtcga | 840 |
| gttacaaaaa | gaaacaaaa | aactgattta | actctaaaga | tttcctataa | agaaattatt | 900 |
| cttgaaattt | cggaaaatca | tcttatatat | atgctacgta | aattcttatg | gtcataactc | 960 |
| ataataaacc | ttagtaccag | tttttggaat | ttagatattg | ttagaatgtg | cagacacaac | 1020 |
| aaaaaaaaaa | tgttgttaga | atatcatcat | gattatattt | catacgttaa | ttaataatta | 1080 |
| aggttcgacc | tctctctcgc | taaactccat | tattacgacc | ttgttatctt | agacacacaa | 1140 |
| ttatgatcac | taaacattta | ctatactatt | taattacttc | cttgatgttg | aattttttgc | 1200 |
| tgtggccgtt | gaaccaagaa | gctaagcaag | gaatcatcat | tgcatattaa | aattatattt | 1260 |
| gtttgacagt | tctttaatgt | cggtttagca | aatagtacgc | ctaaaaatat | ttattgccat | 1320 |
| ttcttgtgca | atttattctg | tcacatgtca | atgcaaaaaa | ttaacgcctt | ttagatcaat | 1380 |
| attgatttag | atgagtacaa | ctattttgt | aaaattttgt | tagggtttgt | agtttatacg | 1440 |
| tattttggca | ttgtactaaa | ttttgtagtt | cattttattt | atttattttg | taattcatat | 1500 |
| tttcgtagat | aagtatagtt | tgtgatagga | tatgcccctt | tatgtttcct | agcatgctag | 1560 |
| tttaaccaca | ttctccaatg | cttttttgtta | tcgagattat | gatccaaatt | tatatagtat | 1620 |
| taaacgtttc | attgtcacaa | aatcatttcc | ccttaggaaa | aaagagaaa | gtatctcgat | 1680 |
| atacaaacaa | acaactcatg | tgcccaaaag | gttaaatgtc | aacaccaata | gcaaattacc | 1740 |
| gaagtaccct | tataaccgcc | ttaaatcttg | ttagccaatg | ggagatgctc | ctcgattgtg | 1800 |
| tgtcttgtct | gagtctgcga | ttggttaatc | tctaaacgtc | tttggcctat | cattaggcaa | 1860 |
| cgtttagccg | caaaccccct | ctcctattag | ttgagtcata | ttattaattt | catcgataaa | 1920 |
| acaaaaataa | atactaatag | aaaaaaaatc | aatcaacggt | cctcgaaagc | ataaaaatgt | 1980 |
| attaaaaaaa | aacaaagttc | cttgagaaca | aatgagatct | gaacatgtgt | gacttgccta | 2040 |
| ttcaaagacg | acacttgtct | tttcctgaat | tatgtgatgg | tctatcatag | actatacaag | 2100 |

```
gacgagtgtt tattggttga ttgaattaaa aaggtacaac gaaaagaaaa agaaatacat    2160
aaaaaagaat gttttttgata tttaactaat ctcactttga aatgaaacct ttttaattag   2220
aattgaatta tactaatagt acttgtacta tgttgatgtg aatacttac ctaagaaaat    2280 tagatcagaa aattgtataa tttatacatc aacaccaaca ttgttttcta tagcatcgta   2340
ttttatttgt gtcgttattc acaaacgttt tgtaacataa tttaacacca tagattttgt   2400
taattaagca ctgttgccat tctcatttat acacatttt accgtttgat ttatccttag   2460
tcataaaatt gttacattat ctgatttctt tatatatata ttttaatttc aataacgttt   2520
agtatatttt gaagggaagc ccaattggta gatttaagtg atcaagaaat taaaaaaact   2580
cgtagatctt aatatgaata ataaaataat gaaaagccca gaatttttg tctgggaaat    2640 actgaaagac aatcacagct caacagcttt ttaactcacc tctcactctc agatcattcc   2700
tgtttcatat tcatctctct cccctctctc cctctatatc tctctctccc ttttcgactt   2760
gagagtttgg gtcctttggg agaaagaaga agaagaagaa aaagattgga ttttgttcac   2820
tttaacatct tcaatctcta aacccacctg agttttctcc atttctctgt ttggtttctt   2880
gtcagttttc aagaaagcgt ccaaatccta gatcctctgt tttctcttct ctgtttgctt   2940
tcattttctc tggattcgga tctgaccact aaagagaggt ttatcgtttc agacaacaaa   3000
actcaaagat cgaatctatc ttttgtcctt agagtctgga aaagcagct ctcttttgat    3060 ctcctcttta gattcttcaa agctttagat gcttatctct ctttctctct cagattccat   3120
ttgaataaat gccattttga cagatcaaat atctcccact tttctctctc tctctctctc   3180
tctctctctc tctgtttgag ctccaccatt atcgaaaact ctgttttttt ctttcttct    3240 tgattcgatc aacaatcgtt gaaaac                                        3266
```

<210> SEQ ID NO 34
<211> LENGTH: 3167
<212> TYPE: DNA
<213> ORGANISM: Arabidopsis thaliana
<220> FEATURE:
<223> OTHER INFORMATION: At5g58900 Promoter DNA

<400> SEQUENCE: 34

```
atgattccaa agtgtttggt caatcctttt ttggcaattg actaatccca aagcatgtat    60
tttcttaatt atatttaaag taatatgtca tatttagttt aaaaagtttt ttgataggat   120
aacgtattga agaaacatcg aattagatac aaaaaataat cgtaactgag aaatgtagat   180
atgacatatt actctatata tatattagcc gtaactatca ctggagatgt acactgtaac   240
atataaatga ttgggggaca aaggtttttc tctaatagta tatgatcaag gttaattaaa   300
cattctgaac tggattaagg tgatataata tactactctc taagtacggt atggtaccat   360
taccggccat gtaacacaag cttaccggtt taaaagacat aatctatttg actaaaatgt   420
aattaattaa ttagggctcc ctaaacactg ttattaggaa atgcgatccg tgaaatgggg   480
aatgttatgt tgtacgaaac tcggtaatgg atttctttga catgttccaa gattcttcat   540
aaaataaaat aaaatcatta tggtgttttg aataaaagac aactcatgcg atggtcaact   600
actgtgatag aaactcacca ataaaatcaa tttgacattc tttttgaatg aaattttgtt   660
gctaagggaa taaattaaga gatgcatggt atattttagt gatgtaccat ttaaccatct   720 tgtaaaaatat actcatttct tttctcattt attataaagt ttatataatg cattatttga   780
tactaattat gtatacttat tattttttt tattttttt aatgtatact tatttcttat    840
gtttaaatgt ttatttcctt aaatttaatc aaaaaaatat gtttcaaaca tcgatctgat   900
```

```
taattacaaa taaccrccat agaatctgtg ctttaaaaag acaagcaact atgatgatca      960
ttaaccaaac cgaaccaaat tgggagcaat cggagatctc acgtgtccac ttttcattaa     1020
atcataatga atagatctaa cgtacagtat taagccacgt taacaaatca taatggagaa     1080
gacagattcc tcgagatctt aaaaaaaaca gaaaaggaaa ataaaagaaa acagtaaaga     1140
gagagagaga gagaaagaac cgaccaatga taatgcaaaa cgcggatctc acgtggaccc     1200
ctttgtacaa cttggccatg aaagttaccg ctgatctcga ccgttcattt ggcggctcct     1260
tttccctcat ctgacacata aaatcccaat tgccaatat tatacaaaat gtacgtaatc      1320
agtgaaaata aagattataa aagtatacag aagcacgtat atgtttgttg tatattagtt     1380
taatatgaat gttgaaaact tggtattgtt ttttcagagg catcgtacac tcccacaaaa     1440
tgtcaacttc gcgtatttaa attaattaaa taattatcat acattgtttt tgagtttttt     1500
ttctcccttt tttgtgcctc aatgtcaatt attttgtatt tcacaattta tcagagtgtt     1560
caccagcatt attattttgt aattatatcg ttcacggaat ttttcttcga ttcattttat     1620
tttctttctc aaagttccaa aattatattt ttcatgtctt tccgtgtgac caaatcaaac     1680
acaagaattt acgatttcat cattaatcga tttacattta gttcgaactc taacatattt     1740
gttacgccat ttatactagt gaatatgtaa gacagttata actgtaaagt tctaactata     1800
ctaattactt ttccattgaa aaagcttaaa agtttttagg gtccaattaa gtagctaaag     1860
tttaatcaaa atgatttcaa aagtagtaga aaaatatgca gttttgttta accggtggtg     1920
aaatgatgat tatgaaatta agaaaaaaaa atgtttatga ttaagaaaga gtttgtaact     1980
atgtataagg agtaaaagta atcttgatta ggaaaataat tttaaaatta cagcaaacaa     2040
tttagttttc attttcaata atagtgaata taattaaaca atttataaaa taaaataaaa     2100
ataggagaaa ttgaaaaatg gaccacattt ggtgtataga tagacacgga cggtagtgag     2160 caattttta agcggttcat aaccacttta ttttaaattt taatacatgt tttaatcatc      2220
ttttctcatt tcaaatatct atttgaagcg tccgtttaaa actttcaacc attttaccca     2280
aaactgttaa gtcatgagta ttttttaacta ttaagcagga atattactat gcaaggtgac    2340
aaaaaaatag aaagaagtaa aaaagagaat caaatcttaa attttaagaa gaaagaaaa     2400 aacagcatca accaaaaata ataattttatc aaggacagaa ctataagagc ccaaatcatc    2460
acctcctttc tctgcctact tctctctttt tttttaact cgagaagttt ataatctggt      2520
ttctgatttt agttttcttt ccatttatgg gttcatttgc ttcttcttgc acgttatagt     2580
tttcctaatt gggtaagctc caaggtagct tcttcaatat taatttcatt ttttcatttt    2640
tctgtagcca tatgtttatt ttcccgagaa atattatcca cacccagatc tttaaatctc     2700
ttttaactct gagtctctga tacttaaata ccactcatgc tgcttattag ctccaccaaa     2760
tctggaaaac caatagattc ttttttattc tctgcaaaa atctcagagc taccctaaaa      2820
attctctctt tttgactcac ttaccagatc tccactagat tttactcaat tcttttcaa      2880 aaggtttaaa cttttataga ttccttgaag tgggtctaag caatgcttca gagaaattcc     2940
gatgatttct tctctaacca aaataaaaat gaagtatcat ttgatagtga ttttgtgtt     3000 cttcttttga ttctcttatc tcttccttcc catcaataaa cccaaaaaaa ttaatatcat     3060
ttttgggatc ttattgatcc caaaattcgt aaatccgttg acctttgtcg gcatgatttg     3120
ttcttactta ccgtaaaaaa aacagagcta ggttttagtt ttcggac                   3167
```

<210> SEQ ID NO 35

```
<211> LENGTH: 4109
<212> TYPE: DNA
<213> ORGANISM: Arabidopsis thaliana
<220> FEATURE:
<223> OTHER INFORMATION: At3g16350 Promoter DNA

<400> SEQUENCE: 35
aaacaatatc actttttgtt gatatgccag cacttgagaa acagcaagcc gttgtttcaa      60
aagaaaatac agaggaaaac agagcagaga acggctcaaa gagtaagagc attgacgtga     120
aaagaggaat ggttctacct tttactcctc tcacaatgtc cttcgacaac gtaaactact     180
acgtcgacat gcctaaggta acaccaaatc ccaaatcctt gttgacatta aaaccataaa     240
gatgttaacc aaaaaagaaa acaggaaatg aaggaacaag gagtttccaa ggataagctt     300
cagctactaa aggaagtgac aggggtcttt aggccagggg tattaacagc tttgatggga     360
gttagtggag ctggtaagac cactttaatg gatgttttag ctggtagaaa aaccggtggt     420
tacatcgaag gagacatcag aatctctggt ttccctaaaa gacaagaaac ctttgcaaga     480
atctctggtt attgtgaaca gaacgatatc cactcaccgc aagttactgt caagagtct      540 ctcatctact ctgctttcct tcgtctccca aaagaagtca ctaaatatga gaaaatggta     600
acacttcttc ttgtaactta acaccattta taataggatc tcaatccata caccaacttt     660
tgcagagatt tgtggatgaa gtgatggagc tagtagagct agagagtcta aaagacgcgg     720
tggtggggct tccaggtatc acagggttat caacagagca gaggaagaga cttacaattg     780
cagtggaatt agtggcgaat ccatctataa tcttcatgga tgagccaacc tctggtcttg     840
acgctagggc tgcagcgatt gtgatgagga cagtgaggaa tacagttgac acaggaagaa     900
ctgtggtctg cacaatccac caacctagca ttgatatctt tgaagctttt gatgaacttc     960
ttcttttgaa gagaggagga caagtgattt atgctggtcc tttaggtcaa aactctcaca    1020
agattatcga atatttccag gtcagattct acatttaatt tgtcaaggtc tctatattaa    1080
aatgtaagaa ctttcatgat cagtcctctt ttgagaaact gcaggcgatt catggagttc    1140
cgaagattaa agagaagtat aatccggcga catggatgct agaagtgagc tcaatggctg    1200
cagaagctaa gcttgagata gattttgctg agcattataa aacatcatcc ttatatcagt    1260
aagttcaacc taatattcaa agctaagatc attccagata ttttaactca attagaattg    1320
ttcgtggtgt agacaaaaca agaatcttgt aaaggaacta agcacaccac cacaaggagc    1380
aagcgatctc tacttctcaa cgcggttctc acaatcattg ttaggacaat tcaaatcttg    1440
tttgtggaag cagtggataa cttactggag aactcctgac tacaatctag caagattttt    1500
ctttacattg gctgcagctg tcatgctcgg atcaattttc tggaaagttg gcacaaaaag    1560
gtttgtttaa ttacttgaat cgaatacaga ggcctcaaat ctagtatcag agtccttact    1620
tatatctaaa ctctatacaa ctgttttcaa aaacagggaa aacgctaatg atcttacaaa    1680
ggttattgga gcaatgtatg ctgctgtttt attcgtgggc gtaaacaact cttcatctgt    1740
ccaaccgcta atagccgtgg aaagatctgt attctataga gaaagagctg ctgaaatgta    1800
ctctgcttta ccttatgccc tagcacaggt gagattaaac tagaaacgtt ttagttactt    1860
gacaaacaag aaaccttaat gggtcgtaaa gcagtcttta actaaaactt tcccatggtt    1920
tcaggtggta tgcgaaatac cgtatgtgct gatccaaact acatattata cactaattat    1980
atacgccatg atgtgtttcg aatggacatt ggccaaattc ttttggtttt acttcgtatc    2040
atttatgtcc ttcctctact tcacatacta tgggatgatg acagttgccc tcaccccaaa    2100
tcagcaagtt gcagctgttt tgccggagc tttctacgga cttttcaacc tcttttctgg    2160
```

```
ttttgtcatt cctagaccgg ttagtgttgg ttacttttct ggcaagaaag ctgaaaccct    2220
aaatgattct ctattgattc tatcataagc tggttttact ttcctcttgc agagaattcc    2280
gaaatggtgg atatggtatt actggatctg tccagtggct tggactgtgt atggattgat    2340
tgtttcgcag tacggtgacg tggaggatac gattaaagtt ccgggtatgg caatgatcc     2400 gacgataaag tggtacattg aaaaccacta tggatacgac gcagatttta tgataccgat    2460
tgctactgtg ttagtgggct ttactctctt ttttgcgttt atgtttgctt ttggcataag    2520
aacgctcaac ttccaacaac gatagggtgt agttgcctgc cggatatgtt tggcgtgaag    2580
tagaaaaaaa tgaaaaatga gggtttatgc catatagttt gtgattgatg ctttattgat    2640
tgtaagtaaa gtgtacaata tatacaacac aatagattgt ggggagaatt tacaaggaca    2700
aatctaatta taattaactt aagatctaaa tttatgtata tcctaacagt tatatccgtt    2760
ttgtacacta ttttaaaact ttttacagat ctaagataaa catagattta ttttaagaat    2820
caaattgtga aaactctgcg tggaaaaaat taatcatgag tcatgacaat gatgagctag    2880
ttaaggttcc aagtgattgc aatcacattt tgtgagcact aaagaacaca tacacacact    2940
atatatatat tcttgatcac ctaacgagtg aatcaaaaga gatgagtagt ttattgtatt    3000
ttgggacaaa cttcgattaa ataatattta cactatttca tgaaaacatt tgatcactca    3060
tcaaatacat cttatgaagg cgcatatata tctactgttt atgaaatcta atctacttta    3120
ctatatgaaa aaaacataca aatttgccgg agctttctaa agacttctca gcttcttctc    3180
cggtattatc atccctagac cggtcaattt tggttactta agttgcaaga aatctccgtg    3240
taacccaaat ttcataaatg cgtagtggga tttactcttc ttcttttttg gtttcatatt    3300
tggtgtttgc ctttcgcgta aaataccaac atatagcaaa gagcgtttag acgtcaaatg    3360
tgtttgtttt atttgtgtag agtatacata ctttttttaag aaaagaaaaa agaagttatg    3420
aaagcttgtt ctttttttgtt aaagattatg aaagcttgtt taaatcctaa tcacatctcg    3480
tactaaataa agaactatat gtgtgtgggt aatattatcc aatctcttta aatttaaacc    3540
acttgtctca tctcatatgc aaaacgtgta tcttgtaaga acacacgctc ttctaatata    3600
gaaatagatc gcgtaacaag tggacttgga aaagctatag tttatggcgt tttcggacag    3660
atttacactt aaataatatt atcctcacat cttttaaatt caattatttc attatcttgg    3720
ttatcagaac tgagttttgt cggtaacatt gtatctttaa aaaaaattat cctaaacaaa    3780
gaacgaaacg atacaatagt ataaatttgt tcttgtcata aacgataatt tccaggtaag    3840
attaaggata aaacaaaaaa gcttataata gcaatttaaa acacgaattc aacgtacgat    3900
ccaccacaat cctcgtcgtc tttcaaactt aaaataccga aactaccctt accttcttct    3960
ttccataaga aatcaaaacc aagtcctatg gtcgcaattg tatctctatc taaaaatctt    4020
ctttgaattt gtgtatacac aaatcttatt caacgaatca tttatcacca aaaggttctc    4080
tcttttttgt ttgtttctgt cttgtgtga                                     4109
```

<210> SEQ ID NO 36
<211> LENGTH: 1233
<212> TYPE: DNA
<213> ORGANISM: Oryza sativa
<220> FEATURE:
<223> OTHER INFORMATION: Os Actin Promoter DNA

<400> SEQUENCE: 36

```
ctcgaggtca ttcatatgct tgagaagaga gtcgggatag tccaaaataa aacaaaggta     60
```

```
agattacctg gtcaaaagtg aaaacatcag ttaaaggtg gtataagtaa aatatcggta    120
ataaaaggtg gcccaaagtg aaatttactc ttttctacta ttataaaaat tgaggatgtt   180
ttgtcggtac tttgatacgt catttttgta tgaattggtt tttaagttta ttcgcgattt   240
ggaaatgcat atctgtattt gagtcggttt taagttcgt tgcttttgta aatacagagg    300
gatttgtata agaaatatct ttaaaaaacc catatgctaa tttgacataa tttttgagaa   360
aaatatatat tcaggcgaat tccacaatga acaataataa gattaaaata gcttgccccc   420
gttgcagcga tgggtatttt ttctagtaaa ataaagata aacttagact caaaacattt    480
acaaaaacaa cccctaaagt cctaaagccc aaagtgctat gcacgatcca tagcaagccc   540
agcccaaccc aacccaaccc aacccacccc agtgcagcca actggcaaat agtctccacc   600
cccggcacta tcaccgtgag ttgtccgcac caccgcacgt ctcgcagcca aaaaaaaaaa   660
aagaaagaaa aaaagaaaa agaaaaacag caggtgggtc cgggtcgtgg gggccggaaa    720
agcgaggagg atcgcgagca gcgacgaggc ccggccctcc ctccgcttcc aaagaaacgc   780
cccccatcgc cactatatac ataccccccc ctctcctccc atcccccaa ccctaccacc    840
accaccacca ccacctcctc cccctcgct gccggacgac gagctcctcc cccctccccc    900
tccgccgccg ccggtaacca ccccgcccct ctcctctttc tttctccgtt ttttttttcg   960
tctcggtctc gatctttggc cttggtagtt tgggtgggcg agagcggctt cgtcgcccag  1020
atcggtgcgc gggaggggcg ggatctcgcg gctggcgtct ccgggcgtga gtcggcccgg  1080
atcctcgcgg ggaatggggc tctcggatgt agatcttctt tctttcttct ttttgtggta  1140
gaatttgaat ccctcagcat tgttcatcgg tagttttct tttcatgatt tgtgacaaat   1200
gcagcctcgt gcggagcttt tttgtaggta gaa                              1233
```

<210> SEQ ID NO 37  
<211> LENGTH: 1997  
<212> TYPE: DNA  
<213> ORGANISM: Zea mays  
<220> FEATURE:  
<223> OTHER INFORMATION: ZmUBQ1 Ptromoter DNA

<400> SEQUENCE: 37

```
ctgcagtgca gcgtgacccg gtcgtgcccc tctcttgaga taaggtgagc attgcatgtc    60
taagttataa aaaattacca catattttt ttgtcacact tgtttgaagt gcagtttatc    120
tatctttata catatattta aactttactc tacgaataat ataatctata gtactacaat   180
aatatcagtg tttagagaa tcatataaat gaacagttag acatggtcta aaggacaatt    240
gagtattttg acaacaggac tctacagttt tatcttttta gtgtgcatgt gttctccttt   300
tttttgcaa atagcttcac ctatataata cttcatccat tttattagta catccattta    360
gggtttaggg ttaatggttt ttatagacta atttttttag tacatctatt ttattctatt   420
ttagcctcta aattaagaaa actaaaactc tattttagtt tttttattta ataatttaga   480
tataaaatag aataaaataa agtgactaaa aattaaacaa atacccttta agaaattaaa   540
aaaactaagg aaacatttt cttgtttcga gtagataatg ccagcctgtt aaacgccgtc    600
gacgagtcta acgacacca accagcgaac cagcagcgtc gcgtcgggcc aagcgaagca   660
gacggcacgg catctctgtc gctgcctctg gaccccctctc gagagttccg ctccaccgtt  720
ggacttgctc cgctgtcggc atccagaaat tgcgtggcgg agcggcagac gtgagccggc   780
acggcaggcg gcctcctcct cctctcacgg caccggcagc tacgggggat ccttttccca  840
ccgctccttc gctttccctt cctcgcccgc cgtaataaat agacaccccc tccacaccct   900
```

```
ctttccccaa cctcgtgttg ttcggagcgc acacacacac aaccagaact cccccaaatc      960
cacccgtcgg cacctccgct tcaaggtacg ccgctcgtcc tccccccccc ccctctctac     1020
cttctcaaga tcggcgttcc ggtccatggt tagggcccgg tagttctact tctgttcatg     1080
tttgtgttag atccgtgttt gtgttagatc cgtgctacta gcgttcgtac acggatgcga     1140
cctgtacgtc agacacgttc tgattgctaa cttgccagtg tttctctttg gggaatcctg     1200
ggatggctct agccgttccg cagacgggat cgatttcatg attttttttg tttcgttgca     1260
tagggtttgg tttgcccttt tcctttattt caatatatgc cgtgcacttg tttgtcgggt     1320
catcttttca tgcttttttt tgtcttggtt gtgatgatgt ggtctggttg ggcggtcgtt     1380
caagatcgga gtagaattaa ttctgtttca aactacctgg tggatttatt aattttggat     1440
ctgtatgtgt gtgccataca tattcatagt tacgaattga agatgatgga tggaaatatc     1500
gatctaggat aggtatacat gttgatgcgg gttttactga tgcatataca gagatgcttt     1560
ttgttcgctt ggttgtgatg atgtggtgtg gttgggcggt cgttcattcg ttcaagatcg     1620
gagtagaata ctgtttcaaa ctacctggtg tatttattaa ttttggaact gtatgtgtgt     1680
gtcatacatc ttcatagtta cgagtttaag atggatggaa atatcgatct aggataggta     1740
tacatgttga tgtgggtttt actgatgcat atacatgatg gcatatgcag catctattca     1800
tatgctctaa ccttgagtac ctatctatta aataaacaa gtatgtttta taattatttt     1860
gatcttgata tacttggatg atggcatatg cagcagctat atgtggattt ttttagccct     1920
gccttcatac gctatttatt tgcttggtac tgtttctttt gtcgatgctc accctgttgt     1980
ttggtgttac ttctgca                                                    1997

<210> SEQ ID NO 38
<211> LENGTH: 3001
<212> TYPE: DNA
<213> ORGANISM: Oryza sativa
<220> FEATURE:
<223> OTHER INFORMATION: Os05t0543600 Promoter DNA

<400> SEQUENCE: 38
tacttcaatc tacctaagat taaaagtaat atattttgga acatactcct ggacaatcgc       60
gaggacgtgc gccaaagcct gaatttacat acaattccat cgacatgtgt ttgaattaat      120
tccttctctg aacacggcaa taagccaggg atattttttc tctgtcggta cgacagatta      180
taaaagacag caagggtaat gctcagagaa tgaacagctg atcagaattc agacacagct      240
cgatcgccca ttggtttctg gtcgatctcc caaatcgcgc gtcatatcga tcatttccac      300
tgctgattac tactggagat ttgatcagct gtggtgtgag caggcaagac gttaaatccg      360
tcgccgtcgt cgccgcgtgc ctccacgacg caaacagaaa acgatcgcct acgcagcctg      420
gagcagtgtc caggcgcgcg acgtactatc taatctaagc gcgcgtgcgc gcacacgagc      480
aagtgagcgc tcgtccttct cgaaagttgt tataaaaccg acggtaacta aacacgaaag      540
aacaccataa gagacacgtt ataggttagg caggtttagc cgagatctac atcctgagat      600
accgattacg aaaagcttac ttttgattta gcgtaattat agtgcgtctg tgtatttacg      660
atactcgatc agctggctgg attaaggatc gtaaatacca gacacactat atctattatc      720
atctttaagt tttaatttat aatacatttt acacatattt aacgcaaacg ttataaaata      780
tggcttggca tggcagggtg gctccacctg tcggcgggaa aggaggggg gtgacgcggc      840 gagacagcga tcagcgggggt taattgctac ttgaccgcgt ccgaggatgg aaaaatgtgg      900
```

```
cgtatttgta ttgacgcgcg gacgagacag cccgatgggc acaccaaggt cggcagggca    960
aggcacggcc acggaaatca acggtactaa attttatgtt aaaagaaaat ttcaacaggg   1020
atgtgtaaac ttatgttgct tgaggtgatc ggtgatacac tacataggtc gggctacttt   1080
tgtggttgta ccatatttga tatttctgtt ttaagtagag atggggagag tgttttcacg   1140
tgttaagagg atattttcct cgttttctta aaccatatgt ataagagaaa ttttacggtc   1200
atagatttga tatctcgggt atcaagttta acattagaga atacgattac tcccgatatg   1260
ttttttaagta aataagatat aaaaaagttt accctatgta aaagtcacaa aaaaaaaggt   1320
ttttgccctc ctttaaaaaa taaaatagta tgaaaagcga tgatgccagt atcatatact   1380
ccctccgttt cacaatgtaa gtcattatag catttttccac attcatattg atgctaatga   1440
atctagacat atatatttat ctagatccat tagcatcaat atgaatgtgg gaaatgttag   1500
aatgacttac attgtgaaac ggaggaagta tatgttctat ctactaagat tcaaggctta   1560
aatttcctaa aaaaattctg aagtttaaat taagcctaca cattcagata aaaaaaatct   1620
acagattgtt acatgaacta tttactacgg tatttgcctt ctctgcctct tactttgtag   1680
atagagttta gatttatttt tatcagatgc cagtatactc cgtatttata tatttttaa    1740
aatatataac tattttgttt ctaaaaaaaa ctatttgtgg caagctggag atataaaggt   1800
acgtatatat aagagggcat ccgccttgat tacttaagac cgtaccaaaa agatgaacat   1860
gatcacaaag cttgttatag agttgtcatg ctcacgtaac ccaacgccta aatcaaaggg   1920
atcatgctag gaaaaaaaac ataattagaa cactgattta acaaaaaaat gaaatgctag   1980
agaaacataa aaagcaaaat cgtctaaaat tccaattttc cctccatttt tcattcttcg   2040
ccactgtaat ccgatcgtta ccgtgtgtcc gcttttcttc catcaactaa tacagcacct   2100
gcgctccgcc acatccatca aacgatcagt gagattagtg actttaattt gattaatcaa   2160
ttaattaaat taattatctc tctcaagatc agcgagtggc cgtgagctga ttactgtcat   2220
cagtagtagt aaacacagtg attcccagtc agttcgatca tgtcacgacg ggcgttttca   2280
gggggtgatc aagttggaca agtaaaacgc gatgatctga cgcgattttt ctccgtacca   2340
catcgcgatt ctctgcacag gtccccgatc gagctcattg atggcttaca gttacacttg   2400
ccattaacca gtgtttagtc tctctcttaa ctgtactagc tggattagta tattatattg   2460
ctgtccaaag cagaaatcaa tcttaggcaa aaaaaaaaag aaaagaaaa tggaaactaa   2520
atctctctgt ctctctctct gatctctaac taacactgta attagagaga gaaattaagt   2580
gaggctcttt ggcgcgaact agcagtattt ttatccagcg agatggaggt atcttgagct   2640
ctaatccagc gagctcgaga ggggagtggc agcttgctta gaaaccactt gatcgctgcc   2700
tcacctcacc acaccacaca aacacctatt ctctctctct agctcgctgt ctctgtgtct   2760
ctctctaact gaagttgcag gagttcttgg caagcttccc catatatacc cgaccaccac   2820
cgggcaacgg ttgatcgata tagccagtga ggagaagggt tatagaggct gatcgaccat   2880
cgatcgacgt cgtggcgagc ggctagtgtt cgttgtcgtc gtcggcggcg gcgaggtggt   2940
ggtggtggta gctacgtagg ttgtggacat cgatctagag gtagaggcag ggaggggag   3000
g                                                                  3001
```

<210> SEQ ID NO 39
<211> LENGTH: 3001
<212> TYPE: DNA
<213> ORGANISM: Oryza sativa
<220> FEATURE:
<223> OTHER INFORMATION: Os01g0142500 Promoter DNA

<400> SEQUENCE: 39

```
ctccaatctc cttctcctcc tcctcctcct cctcctcctt gccgcagctc agctcactgg    60
aaagtagaag taaataagaa ggtgagattt tcttttttt tccttttttt tttgtttggg    120
tatcagaaca agatcggatt ctaaataaca ttgcgaattt gcaaaagctt gcaaaagcca    180
cgggaattta tcaacaggaa cttgcgttga tgcaaaatca gacgagatac acatggaatt    240
ggaggagaga tttaggggg gagaaaaggt tggaatcttt actacgagca aatcaactga    300
aactctgaga taattgtaac acctacccctt atgattagat gagatgagag taccaacaaa    360
ctgaataaga ggcaccttac cgaacagatt agattgattg caagaacaga ttggattaat    420
taataaaaaa acccaaaatt cacaaatctc ttagcaaatt gaccaaacct catccaagac    480
aaacacggca acgtttggaa ccacactaaa ttgcattacc aagaaccaaa tcaactccaa    540
aaagaatcaa aatttaacca acaccaaaa atcactcac cttcaggtcg atctctgcct    600
cggaacgagg acaagaggcg atcgatctcc ctcggttctt gctcgaattc tgcgaggatt    660
tcttctctcc cctcacctct ctctctctta gcctctctct ggcttattta gctactgcta    720 tagcttttctt tccctgagca ctaataagaa gcaaaaggga tagcgatcca aagtcaggtt    780
cttgagagtg gcagctggtg attgggcctt gcatctcagc ttgtggccga cttttacact    840
atatatatat tattcaccct aatacccgta tgatgcctgg tagctagcta ggccgcatat    900
atgtgcgtgc gtgcgcatac acgcatgcac acttgggctt gctcttcttc tcttctcttc    960 ctcccccccct tgctttgctt ttacctccac tacatgctac ttggccaata ccttttcctg   1020
aatttggagt ttttgacatc cttaattgca aaggtttata ttcttttct actgatagaa   1080 aaccaaaaaa gaatttgcaa ttggtaatag tggttttctg tcggcagcaa agcagtcaaa   1140
ttaggcctat atagctctag gctctaacca aaccgagttg tagctacatg tcagtgaatg   1200
gtttgttcta atgcaacttg tgcaggggg gactgtagct gtgtgcccag ctaattaatc   1260
aacagccatt aattaatcag tatgtgtata aaataacagt tgttgtgtgt tgctttaggt   1320
ggctggggag cttggaagga gtggtggtgg agttgtggtg tgagatgttt aattttgtgt   1380
gtgtgcaggt gatgaacatg attagtcgcc gttgacaagt agagatcaag agggtttcat   1440
cgacttgttg ctgtcatccg tttggtgaga gggcatatga tttgctggcc aagcattggg   1500
cggtcattgt tttatcgcag acaaaaaaaa ataattgatt ggctttctct tgcagtaagt   1560
aagtgttgct cgtccgtgtt gttggcggct tgcgtgagcc tgaacctcaa cttcttggtt   1620
tatatggatt tgtcagaccc aaaccttgta aaagatgatt ggtgcttcac actactaatc   1680
tcgtcatttc acaggaaatg attcagctcc atcacgaata attttattgt ttgggatgac   1740
ctcggctctt tagcttatca gttgcagata aaatttaaat tctaaatcca gagcttattt   1800
tgatattttt ccagttgttt attttctagt attaataacc tttaagacac taaaaataca   1860
tatataaaat gttacacgt aaattacttt ttagtcagta atgcgctatg tcttaattat   1920
aatcagttgt aagcgaccca aaaataaatg ttgggatccg actctgataa ggtagagtct   1980
tttactcttg aatccaattt agacttacgg cttctttaga acacataatt tttatagtaa   2040
ttagctcatt ttttctaaa aaaagattc ctccattcca aaagaggcct tggttcttgt   2100
atattccctc tgtcaaaaaa aaaaataaat ctatgattat tctagtacaa cgaattatct   2160
ggacagattt atgtccagat tcatagtact aggatatatc acatctagaa ttaggttggt   2220 ttttttaga atggagggag tataagttta ctaaaactac atctattgtg atcatatgtg   2280
```

```
gagatgtgta ctttacacaa tttagagcga tgtggtactc ccatgctaac caggggcagc    2340
caactagatc ttaaatgtgc ttaagtattt atgttcccta cttttagtga ataattgcgt    2400
tccatacttt gttgagagca ttaagccagt ttagctgatt gcgttgtgta actatatata    2460
actcttttct tataatatat tgacgtgcaa tcttttttgcg cattaaaaaa agcatcttct    2520
tcaactaaaa caggttattc actacactag caaattttgg atttaatgca tgctgaacac    2580
atgaataatg ttcagagctc tgttcagata tgccttcttt agagtgcaca tctgaaactc    2640
atttatttca atttgggaga atatttccac tctgctgatc ctcccaacac ttgtgttgga    2700
aattaggtgt ttcaagaatg tgcattgctg aaggccgagt ttagtttcaa acttttttctt    2760 caaacttcca acttttttcat cacatcaaaa ttttcttaca cacacaaact tccaacttttt   2820 ccgtcacatc gtttcaattt caaacaaact tccaatttta ccacacaccc caaatttgtt    2880
agggattgta gtacgttctc ctgtgtgctg tcgcaaagta ctatgcaaag gacaaattct    2940
gaaaattaca gcacattcaa tgcttgctgt agtcacaatt ctcagaatct atactggtga    3000
c                                                                    3001

<210> SEQ ID NO 40
<211> LENGTH: 2601
<212> TYPE: DNA
<213> ORGANISM: Oryza sativa
<220> FEATURE:
<223> OTHER INFORMATION: OsFST Promoter DNA

<400> SEQUENCE: 40
cttatatatg gtcattatat atttgctaca tgtcctcacc aaaaaaaagg gctgctatat      60
gcatatatat gtatatatgc tccgaatata tgccaccagc tctccattaa catttcaaca    120
tgatcatgaa tgcgttgtta ctttagcatt actgattcgt caaattcaga tcgaggtagc    180
tagctagact gaatattcct caggatatat aataagttac tgaatgatct tctttattga    240
tttttgcccc tatcgtatgg acttctatac taaattgtcc acccaaaaat tatgtattga    300
tttggacaaa cagaaggtca accaacaatt aacagccaat gaccctctga ctgactgaaa    360
gcaaataaaa tgcataataa cttagatatc attagttctt aagaatactt aataaaatta    420
aaattatttt tttcctggtt acacgataga cgcacatgca ccatgacgct cacacacacc    480
agcgaatgtg cctcctaata cacgttcaaa gagatgaaaa ccaataacat atccccgatc    540
tcactgaatt catattaaaa aacccacttg catgtgcgta ataaaactag ggactaacta    600
gaaaactgtt gcaagttttt taaggaaaaa actttcaaat ctaactatag tataattgta    660
atataatttt actataacta taatgtaact cgtatataag tattaaaata atatatgtaa    720
ctttatatct aaattatata gagatgataa cgtagttaca atgcaattac acaatgcagt    780
tatagtaggg tgcaactgga gtataactaa catgtaactc aattaatttt ttaaaaacat    840
gcaacagatc taagtggcta gcacgcacgg cttgtgggat ggatatccta ggttcaagcc    900
cttgcaagga cacaccttaa ttctcgcgca gatttttttt tccaaatctc gcacgaatca    960
tggcgtggat cgcacggcca gaaaatcaaa agttttcagc ctccaaaact gtcgacggct   1020
agctagcaaa accgtaaaac taaacttact gtaaaggaga aacacggaat ctcgcggaac   1080
ttgatcacat agggaaccct agctctctac tatataatta gccaagccat catggagaga   1140
gatcaaaatc tctgccaaat ttatttcttc cttcccaaat gagggggtgca gtccaccccc   1200 cctccacccc atgtggtaca atgtgcagtg gcagtccccc atcaaggcaa gcaagcaacc   1260
atagtgatca atatgctagc tgcacatata cctctctctc tctctctctc tctctctctc   1320
```

```
tctcttagct agctagcaac aaacaaggga gctagggttt tcttggctct gttgccataa     1380
gcagcaagtg taccctgtcc ctggagagct cctcatggcc atggccaacc taacaaacct     1440
agctgccaag atcggcaagg aggaggaaac cgggtgggcc cacactgtca gagggtggtt     1500
acaagtccac acacatgttg ctttccatgg tgccttgtga ggggcatgca gagagttgct     1560
atagctacat acaccttcct cgcaattgca tgtagtgttc atgatttat accatgccca      1620 tgtatatata gctgcactgt gctctgatga gtaatactgt tgcattatat tgcatgagct     1680
acatacactg atatctctga acttttgtgt gcgtgatata tgcactgttg cagtgtgtgt     1740
tttgtgtcac aagctaggct cgtgtatttg tgcagagatc gaccagagag tatatgctag     1800
tgcatcatca ttgcatgctg caagtacaca catggatatg cacactgatc tgatcatcat     1860
catcatgaag tcatgcttat gtctgcatcc gtttcttgct ttgactcact atctgatcct     1920
aattacacac tgatgcaggg gtaaatgtaa aactagacta gctagcatat tagttacagt     1980
taaaaatgta gtttgttgct ttctggatat ttactactcc ctccatctac ttttgatttg     2040
atttggagta gtacactgat ttgatttgca ggagtagtag tgtgagagtg tgtgacagag     2100
agaaagcatt gtgtgttgca cattactaca agctctctct cctatatatg tctctccttc     2160
tgcacctcct gccttagcct ttgaagcaag cttagcactt cacaaggtat gtacatagca     2220
cattactact cctgccctat ctatctaccc tgttcatgag taattcaaga aaaaaaaag      2280 gacaccttt ctagctagtt cttcatcctt tcgcagcaaa gagttttac atctctagct       2340 actagttgtt ctcttctcta catgaaattt tttctacttc tgattgcacc ctttacatag     2400 ctgtggggg aaatccaatt tgagcaccca tgccttatgt tgatttaac aaaattcgtc       2460 catgtatcga tatgttcata acttggccat ttctgttctt cttcttcttc ttcttcttct     2520
tcagtttcct cttgtgcaga agaaggagaa acaaagaac acagaaatta aattaaactc      2580
gatcaggaag gtatagcagg c                                               2601
```

<210> SEQ ID NO 41
<211> LENGTH: 3000
<212> TYPE: DNA
<213> ORGANISM: Oryza sativa
<220> FEATURE:
<223> OTHER INFORMATION: Os01g0853700 Promoter DNA

<400> SEQUENCE: 41

```
taaaaagttg aagaaaccat ttctcatgaa aaaattata tctacacgag aataggtgga       60 taaagaaga aagaagagag gtgattggat gtgaatttaa tttaaaaaaa ccattcatta      120
gatatatagt ttctatacat agtgtatata tatatgat aagtatgaaa attattctat       180 agttttagg tttgggatgg cctaagaaac cttccactag tgtgatactt aatctgctca      240
gagttccatg gagcagttgc actgaaaaac acccgaccgt tgtataactg catcgcctaa     300
tacccaaaac agcaagagca attagcaaag agtacaccca aaacaagctt tgacaaaaag     360
ggatcgagga actctagaac cgtgattaaa taaatcaaaa gcaggcgtga gagaaaggca     420
gcaggcaaag gacaataaac aaatgcaaca ccacctacaa ttgcacaatg agaaagctgc     480
tctcttctct actgctacca ctgtttctct ccagacctga caagcgcaca aggcacacag     540
atagaaataa ctgtcgtcac ggaaagagag acacagatgt caaacaagga agcaaattac     600
gcggagcagc taaggaaggc cctgttaagt tttcactcaa aaaatttttt accctgtcac     660
atcaaatatt tagacacata cagagagaat taagggccta tttggcacag ctccagctcc     720
```

| | |
|---|---|
| accccctcctg gagctgaagc tcagccaaac agtttcagct ccaccaaaac tgggagtgga | 780 |
| gctgggtgga gctctctcac aaaacgaact atagttgtgg agctgggttt aggcagctcc | 840 |
| acaactccac tccagaccca actcctggag ctaaatttaa gagttggagc tataccaaac | 900 |
| agaccctaaa tatagacaaa aaaaactaat tacacagatt gcgtgtaaaa tatgagacga | 960 |
| aacttttaag cctaattgcg ctatgatttg acaatgtagt gctacattaa acatttgcta | 1020 |
| atgatggatt aattaggctt aataaatttg tctcgcagtt tacatgcgga atctgtaatt | 1080 |
| tattttggta ttagtctatg tttaatactt caaatgtgtg tctgtatatc cgatgtgaca | 1140 |
| cggcaaaact ttttacccct ggatctaatc acaaccgtag gtggtgtttg gatcccgtca | 1200 |
| catcagatgt ttggacatta atttggagta ttaaacatga actactttca aaactaatta | 1260 |
| tataaatgag agctaatttg tctgacaaat ttttttaagc ctaattaatc tataattagc | 1320 |
| acatgtttac tgtagcatca cataggctaa tcatgtatta attaggctca atagattcgt | 1380 |
| ctcgtgaatt agtccagggt tatgacatgt gttttgtcaa tagtctatgt ttaataccctc | 1440 |
| taattagtat acaaacatct gatgtgacag ggactaaaaa ttttttagtcc catccaaaca | 1500 |
| gccccttaga tcccatccta aaactttaca ccatgtcaca tcgaacgttt gaacacatac | 1560 |
| ataaatatt aaatataggc taaaaaataa ctaattgcac atattcgac taatttgcga | 1620 |
| gacgaatctt ttaagcctaa ttgctataag atttgacaat ttggtgctac aataaacatt | 1680 |
| tgctaataac agattaatta ggcttaataa atccgtctca cggtttactg atgggttctg | 1740 |
| tatttagttt tttataagtg cccgaacaac ccatgcgaca ccttatataa taaccgatgt | 1800 |
| aacgcgccaa aactttacac ccctagaaac accctcgaaa tcactatgta aacaccaaaa | 1860 |
| agtcacttag tcagtgcgtc taagttcatg ctgaatttgg aggtttttca cctatcctat | 1920 |
| cggaaatatt acatatcttg ctacttaggg aaaaatcaaa cgcggatata ttttacctat | 1980 |
| agctagtaca cccatcctac atgcccgtat gaaaggaaac tgttttaatc actcgggtgg | 2040 |
| atgtccaccc gtttattaca tgtcatctaa atagttatat tttttttgac aagatagatc | 2100 |
| aatatgtaat atatcactcc acaaacatac aagttaaaat tcaactttca taaattgtaa | 2160 |
| caaaaataac aaacaaaact caaattacta tacatatatt tgcagataaa tttgttattt | 2220 |
| ttgttacaac ttatagaagt tgaatataaa cttgcatgta ttgtggagtg atatattaca | 2280 |
| tattgattta tcttgtcttt ttttttaaaa aaattgttca taaccattta gttgacatac | 2340 |
| aataaatgag tgggcatcaa cccgagtgat tagaatccat cttcacttca tttacaagat | 2400 |
| cataaactta cacctagagc ctatcccatc caaaaaaaaa acgtggatcc ttgtttgttg | 2460 |
| agacatgctt ataactacga gaattcaggg ttcatggttt tcgtctaaaa tcgagagctc | 2520 |
| tcccaaatcg ctcagttgtc tttaacttcg aagaagattc atgaaagaga aaattccaca | 2580 |
| tctcactatg tttgcatttt gaccccatga cggaactgtg aaccctacct tgtcccttta | 2640 |
| ggttgacatc agaaagtaga tggcgcgtag catttgcgat cacgagtttt gaatctcctg | 2700 |
| cgtaactgaa cttgctagct gtcgattgac aagtcctcta cgaagccacc gactagggta | 2760 |
| gcatggtgaa tgccctaatc cgtttgctta ctcaaagttt aagagagcta actatttttt | 2820 |
| cctcctgggt tggagatgcc acaatctcca ccaaggccca atcacaaaca tccacttcct | 2880 |
| tgagtaccctt ttctttaagg cctctaacgg tggaggcgga ataaactccg gccacttcgg | 2940 |
| ctaccgcccg aatttcactc cttccctata tacgcaagct tccttccacc tcgccctttt | 3000 |

<210> SEQ ID NO 42
<211> LENGTH: 3000

<212> TYPE: DNA
<213> ORGANISM: Oryza sativa
<220> FEATURE:
<223> OTHER INFORMATION: Os04g0569100 Promoter DNA

<400> SEQUENCE: 42

| | | | | | |
|---|---|---|---|---|---|
| ttaaggcctt | atttagttgg | ggaaaatttt | tagatttggt | tgtcacatcg | gatatacgga | 60 |
| cacacatttt | aagtattaga | catagtctaa | taacaaaaca | aattacagat | tacaccagaa | 120 |
| aattgcaaga | tgaatttatt | aagcctaatt | aataaattaa | ttaggcttaa | taaatattgt | 180 |
| ttttattagg | aatcactctc | cgacaacata | caatctatgt | aattagtttt | tattgtctat | 240 |
| atttaatact | ccatgcatgt | atccaaatat | tcgatgtgac | tgggtaaaaa | atttttgcgt | 300 |
| gagaactaaa | cagggattta | tttgaacttc | tgcttcctcg | aatcatattt | agggcatgtt | 360 |
| tagttcaaaa | aaaattttac | aatatcacat | cgaatgtttg | gacacatgca | tggagtatta | 420 |
| aatatagaaa | aaacaaatta | cacagttcgc | tagtaaattg | cgagataaat | cttttaagcc | 480 |
| taattactcc | atgatttgac | aatgtgatgc | tacagtaaac | ttttgctaat | gacggattaa | 540 |
| ttaggcttaa | taaattcgtc | tcatggttta | ctgacggatt | ctgtaattag | gttttttttat | 600 |
| tgtgccaaat | atcttatgtg | actcctgtat | aacacgtcca | acctttaccc | ctgaatttaa | 660 |
| atacccctaa | atatttttat | ggagggtgta | aggttgagcc | ggttttacgc | ctcctacttc | 720 |
| tcaccagtca | ggtcaccgcc | tcaccggcac | agagaagccc | ggatacacgg | ggtggtcaca | 780 |
| ctcacggggc | acctacccga | gccaaccccc | gcacacacgc | catctccagt | tctccacagt | 840 |
| gtgggactag | cagcagcacg | gcgccttttt | gcgatttgac | tccgccgcgc | cgtgtcccct | 900 |
| ccgagaggaa | aaatacaagg | ggtccgagcg | gaacaacggc | gaaaagcgac | gacgggactg | 960 |
| gacgagacga | ggcgaagcgg | ggcggctacg | aaaacaatcc | agacaagcgg | ccaagcccga | 1020 |
| cgcacgaagc | cgcgcagggt | tcgcgatgga | ttggactgac | ggacgggacg | tgatcccctc | 1080 |
| gccgcttgcg | cgtgccctcc | ccccgtagcg | ctagcgtcgt | gtccgtgtcg | tgtgtgcgac | 1140 |
| cgactggtgg | atggaaggga | gtggagcggt | gggtgtggtc | gtgccgtgcc | aaaacgccat | 1200 |
| gcgagaaaaa | cccccacgca | accgaacaaa | acatacaccc | ccgccccatt | gaccggccca | 1260 |
| cccgcccgtg | tgtccacacc | gatccatcca | caattccaca | ttcttctcct | gcgctgctgc | 1320 |
| tgctgctttg | actctccctt | cttcccggct | actccataca | cttggcaaaa | cacctgaacc | 1380 |
| aatccaaccc | gcccgttttt | cttctttct | tttcttgtt | tttttttaaa | aatacaggaa | 1440 |
| tacaggaaga | ggagcggagt | ggccgagtgg | gtagatggtg | caagggcggt | tctactagta | 1500 |
| ttctcctacc | tcagtggtgt | ttggatcacg | gactaaagtt | ttgatcagga | cggttctact | 1560 |
| agagtctgat | tcctgtaaca | tcggatgttt | agacgctaat | ttgaagtatt | aaatataaac | 1620 |
| taattacata | aatgagagat | aattcgtgag | ataaattttt | taaacctaat | taatccataa | 1680 |
| ttagcatatg | tttactgtag | caacacataa | gttaatcatg | gattaattag | acttaataga | 1740 |
| ttcatctcgc | gaattagtcc | agagttatgt | aatgggtttt | gttattagtc | tacgtttaat | 1800 |
| acttctagtt | agtgtccaaa | catccgatgt | gacaggacta | gtccctccaa | ccaaacggcc | 1860 |
| cttcagtcta | gcaagttttt | ttaggccatg | tttaaatccc | accataaaat | tttgtaccct | 1920 |
| gtcacatcga | atatttgaat | acctgcatga | agtattaaat | ataggctaaa | aaataactaa | 1980 |
| tttcacatat | tgcgactaat | ttgcgagacg | aatcttttaa | gcctaattgc | tctatgattt | 2040 |
| gataatgttg | tgctacagta | aacaatgtta | atgacagata | aattaggctt | aataaatttg | 2100 |
| tcttgtgatt | tactgacgga | ttctataatt | agttttttta | ttagtatcca | gacaccccat | 2160 |

```
aagacactttt atataatact ctctccattt acttttgata accatatttt attttgacac   2220
acagattaag gataaacaat tttacttatc attcatttaa aaagtgatcc attaatattt   2280
acatttctct atgcccatgt aaccaatctt gtgtggaaga ataaagagtc acacatcatt   2340
aagatgttgg attgaaatat gcctatcaaa aataaaattt ccagatttgg aaatatgact   2400
atcaaaagta gatggagggg taactgatat gacacgccaa aactttacca ccctatccaa   2460
aacacctctt tggcctggtt tagttttcaa cttttttcttc aaacttctaa ccttttcatc   2520
acatcaaaac ttttctatat acataaactt tcaatttttt ccttcaaact tacaattttta   2580 atgtggaact aaacacacct tttttttttt tgttgggctt gtgacttgtg gggtgtgcag   2640
aaagaaggct aggcagatcc aggcagagta gctcttttg ttttgttgg gacctaatag    2700 tactggcagt acagtagtaa aaaaatacaa accctggttt ccgtgtccaa tgtttgacca   2760
tccgtcttat ttaaaaaaat tatgaaaaaa attaaaaga taagtcatgc ataaaatatt     2820
aatcatgttt tatcatctaa caacaatgaa aatacgaatt ataaaataat tttatataag   2880
acagacaatt aaagttggac acggaaaccc aggtttgctt ttttttttt ggacggctcg    2940 cgaaggaagg aaggaaggtg gagccaggct agttaatagc gcgacatacc cgagacgcac   3000
```

```
<210> SEQ ID NO 43
<211> LENGTH: 265
<212> TYPE: DNA
<213> ORGANISM: Agrobacterium tumefaciens
<220> FEATURE:
<223> OTHER INFORMATION: At Nopaline Synthetase Terminator DNA

<400> SEQUENCE: 43
gaatttcccc gatcgttcaa acatttggca ataaagtttc ttaagattga atcctgttgc     60
cggtcttgcg atgattatca tataatttct gttgaattac gttaagcatg taataattaa   120
catgtaatgc atgacgttat ttatgagatg gttttttatg attagagtcc cgcaattata   180
catttaatac gcgatagaaa acaaaatata gcgcgcaaac taggataaat tatcgcgcgc   240
ggtgtcatct atgttactag atcgg                                          265
```

```
<210> SEQ ID NO 44
<211> LENGTH: 250
<212> TYPE: DNA
<213> ORGANISM: Arabidopsis thaliana
<220> FEATURE:
<223> OTHER INFORMATION: At Heat Shock Protein Terminator DNA

<400> SEQUENCE: 44
atatgaagat gaagatgaaa tatttggtgt gtcaaataaa aagcttgtgt gcttaagttt     60
gtgttttttt cttggcttgt tgtgttatga atttgtggct ttttctaata ttaaatgaat   120
gtaagatctc attataatga ataaacaaat gtttctataa tccattgtga atgttttgtt   180
ggatctcttc tgcagcatat aactactgta tgtgctatgg tatggactat ggaatatgat   240
taaagataag                                                           250
```

```
<210> SEQ ID NO 45
<211> LENGTH: 75
<212> TYPE: DNA
<213> ORGANISM: Artificial Sequence
<220> FEATURE:
<223> OTHER INFORMATION: Modified TMV omega 5' DNA

<400> SEQUENCE: 45
gatccacaat taccaacaac aacaaacaac aaacaacatt acaattacag atcccggggg     60
```

-continued

```
taccgtcgac gagct                                                    75

<210> SEQ ID NO 46
<211> LENGTH: 67
<212> TYPE: DNA
<213> ORGANISM: Artificial Sequence
<220> FEATURE:
<223> OTHER INFORMATION: Modified TMV omega 3' DNA

<400> SEQUENCE: 46
cgtcgacggt accccgggga tctgtaattg taatgttgtt tgttgtttgt tgttgttggt    60
aattgtg                                                             67

<210> SEQ ID NO 47
<211> LENGTH: 43
<212> TYPE: DNA
<213> ORGANISM: Artificial Sequence
<220> FEATURE:
<223> OTHER INFORMATION: Modified SRDX 5' DNA

<400> SEQUENCE: 47
gggctcgatc tggatctaga actccgtttg gtttcgctt aag                      43

<210> SEQ ID NO 48
<211> LENGTH: 43
<212> TYPE: DNA
<213> ORGANISM: Artificial Sequence
<220> FEATURE:
<223> OTHER INFORMATION: Modified SRDX 3' DNA

<400> SEQUENCE: 48
cttaagcgaa acccaaacgg agttctagat ccagatcgag ccc                     43

<210> SEQ ID NO 49
<211> LENGTH: 30
<212> TYPE: DNA
<213> ORGANISM: Artificial Sequence
<220> FEATURE:
<223> OTHER INFORMATION: At5g07260 5' Primer

<400> SEQUENCE: 49
gatgtatcat catcttcaaa cgaggatttt                                    30

<210> SEQ ID NO 50
<211> LENGTH: 30
<212> TYPE: DNA
<213> ORGANISM: Artificial Sequence
<220> FEATURE:
<223> OTHER INFORMATION: At5g07260 3' Primer

<400> SEQUENCE: 50
acggtggact ggaagagcat tttggacatt                                    30

<210> SEQ ID NO 51
<211> LENGTH: 30
<212> TYPE: DNA
<213> ORGANISM: Artificial Sequence
<220> FEATURE:
<223> OTHER INFORMATION: At5g26660 5' Primer

<400> SEQUENCE: 51
gatgggaaga cattcttgtt gttttaagca                                    30

<210> SEQ ID NO 52
```

```
<211> LENGTH: 30
<212> TYPE: DNA
<213> ORGANISM: Artificial Sequence
<220> FEATURE:
<223> OTHER INFORMATION: At5g26660 3' Primer

<400> SEQUENCE: 52
aaggctctga tcaaacacca tgttattaag                              30

<210> SEQ ID NO 53
<211> LENGTH: 30
<212> TYPE: DNA
<213> ORGANISM: Artificial Sequence
<220> FEATURE:
<223> OTHER INFORMATION: At5g01200 5' Primer

<400> SEQUENCE: 53
gatgtcatcg tcgacgatgt acagaggagt                              30

<210> SEQ ID NO 54
<211> LENGTH: 30
<212> TYPE: DNA
<213> ORGANISM: Artificial Sequence
<220> FEATURE:
<223> OTHER INFORMATION: At5g01200 3' Primer

<400> SEQUENCE: 54
actccactgc ggaaacgcat tataatagct                              30

<210> SEQ ID NO 55
<211> LENGTH: 30
<212> TYPE: DNA
<213> ORGANISM: Artificial Sequence
<220> FEATURE:
<223> OTHER INFORMATION: At2g38090 5' Primer

<400> SEQUENCE: 55
gatgaacaga ggaatcgaag ttatgtcacc                              30

<210> SEQ ID NO 56
<211> LENGTH: 30
<212> TYPE: DNA
<213> ORGANISM: Artificial Sequence
<220> FEATURE:
<223> OTHER INFORMATION: At2g38090 3' Primer

<400> SEQUENCE: 56
catttggaga tacgcattgt acgattcgaa                              30

<210> SEQ ID NO 57
<211> LENGTH: 30
<212> TYPE: DNA
<213> ORGANISM: Artificial Sequence
<220> FEATURE:
<223> OTHER INFORMATION: At5g58900 5' Primer

<400> SEQUENCE: 57
gatggaggtt atgagaccgt cgacgtcaca                              30

<210> SEQ ID NO 58
<211> LENGTH: 30
<212> TYPE: DNA
<213> ORGANISM: Artificial Sequence
<220> FEATURE:
<223> OTHER INFORMATION: At5g58900 3' Primer

<400> SEQUENCE: 58
```
tagttgaaac attgtgtttt gggcgtcata					30

<210> SEQ ID NO 59
<211> LENGTH: 30
<212> TYPE: DNA
<213> ORGANISM: Artificial Sequence
<220> FEATURE:
<223> OTHER INFORMATION: At3g16350 5' Primer

<400> SEQUENCE: 59
gatgactcgt cggtgttcgc attgtagcaa					30

<210> SEQ ID NO 60
<211> LENGTH: 30
<212> TYPE: DNA
<213> ORGANISM: Artificial Sequence
<220> FEATURE:
<223> OTHER INFORMATION: At3g16350 3' Primer

<400> SEQUENCE: 60
gatagcctga atcgcgctgt tgcctttact					30

<210> SEQ ID NO 61
<211> LENGTH: 38
<212> TYPE: DNA
<213> ORGANISM: Artificial Sequence
<220> FEATURE:
<223> OTHER INFORMATION: At5g01200 Promotor 5' Primer

<400> SEQUENCE: 61
gggaagcttc ggacttctga ttgatccata gtttgtcc					38

<210> SEQ ID NO 62
<211> LENGTH: 40
<212> TYPE: DNA
<213> ORGANISM: Artificial Sequence
<220> FEATURE:
<223> OTHER INFORMATION: At5g01200 Promotor 3' Primer

<400> SEQUENCE: 62
gggggatcca gctcctcctc tgtttttggt gaaaactttc					40

<210> SEQ ID NO 63
<211> LENGTH: 21
<212> TYPE: DNA
<213> ORGANISM: Artificial Sequence
<220> FEATURE:
<223> OTHER INFORMATION: Os05t0543600 5' Primer

<400> SEQUENCE: 63
gatgggacgg ctgtcgtcgt g					21

<210> SEQ ID NO 64
<211> LENGTH: 30
<212> TYPE: DNA
<213> ORGANISM: Artificial Sequence
<220> FEATURE:
<223> OTHER INFORMATION: Os05t0543600 3' Primer

<400> SEQUENCE: 64
gaagtattcc aagttgaagt cgaattgagc					30

<210> SEQ ID NO 65
<211> LENGTH: 30
<212> TYPE: DNA

```
<213> ORGANISM: Artificial Sequence
<220> FEATURE:
<223> OTHER INFORMATION: Os01g0142500 5' Primer

<400> SEQUENCE: 65
gatgatgatg agggatgtgt gcatggaggt                              30

<210> SEQ ID NO 66
<211> LENGTH: 30
<212> TYPE: DNA
<213> ORGANISM: Artificial Sequence
<220> FEATURE:
<223> OTHER INFORMATION: Os01g0142500 3' Primer

<400> SEQUENCE: 66
aaacaatatg cttcggctcg cggccaactg                              30

<210> SEQ ID NO 67
<211> LENGTH: 39
<212> TYPE: DNA
<213> ORGANISM: Artificial Sequence
<220> FEATURE:
<223> OTHER INFORMATION: OsFST promoter 5' Primer

<400> SEQUENCE: 67
ggccggcgcg ccttatatat ggtcattata tatttgcta                    39

<210> SEQ ID NO 68
<211> LENGTH: 39
<212> TYPE: DNA
<213> ORGANISM: Artificial Sequence
<220> FEATURE:
<223> OTHER INFORMATION: OsFST promoter 3' Primer

<400> SEQUENCE: 68
aaatttggat ccgcctgcta taccttcctg atcgagttt                    39

<210> SEQ ID NO 69
<211> LENGTH: 30
<212> TYPE: DNA
<213> ORGANISM: Artificial Sequence
<220> FEATURE:
<223> OTHER INFORMATION: Os01g0853700 5' Primer

<400> SEQUENCE: 69
gatgatggca gagcgcttc gggaggtgct                               30

<210> SEQ ID NO 70
<211> LENGTH: 27
<212> TYPE: DNA
<213> ORGANISM: Artificial Sequence
<220> FEATURE:
<223> OTHER INFORMATION: Os01g0853700 3' Primer

<400> SEQUENCE: 70
caagtgtccg cattgcatct gcaggag                                 27

<210> SEQ ID NO 71
<211> LENGTH: 30
<212> TYPE: DNA
<213> ORGANISM: Artificial Sequence
<220> FEATURE:
<223> OTHER INFORMATION: Os04g0569100 5' Primer

<400> SEQUENCE: 71
gatgcagttc ccgttctccg gcgctggccc                              30
```

```
<210> SEQ ID NO 72
<211> LENGTH: 30
<212> TYPE: DNA
<213> ORGANISM: Artificial Sequence
<220> FEATURE:
<223> OTHER INFORMATION: Os04g0569100 3' Primer

<400> SEQUENCE: 72
cacgtcgcaa tgcagcgccg tcttgatctt                                           30
```

NUCLEIC ACID MOLECULE AND VECTOR INDUCING ENDOSPERM DEVELOPMENT IN SEED PLANT WITHOUT FERTILIZATION, TRANSGENIC SEED PLANT CAPABLE OF DEVELOPING ENDOSPERM WITHOUT FERTILIZATION AND METHOD FOR CONSTRUCTING SAME

CROSS-REFERENCE TO RELATED APPLICATIONS

This application is a National Phase entry of International Application No. PCT/JP2019/008706, filed Mar. 5, 2019, which claims priority to Japanese Patent Application No. 2018-039033, filed Mar. 5, 2018, the disclosures of which are hereby incorporated by reference in their entireties for all purposes.

SEQUENCE LISTING

The instant application contains a Sequence Listing which has been submitted electronically in ASCII format and is hereby incorporated by reference in its entirety. Said ASCII copy, created on Sep. 16, 2020, is name 093803-1209645-006300US_SL.txt and is 107,432 bytes in size.

TECHNICAL FIELD

The present invention relates to a nucleic acid molecule and a vector that induce endosperm development in a seed plant without fertilization, a transgenic seed plant that can develop endosperm without fertilization using the nucleic acid and vector, and a method of producing the transgenic seed plant.

BACKGROUND ART

Seeds of seed plants are mainly composed of embryos and endosperms. The embryos are infant plant individuals formed by development of fertilized eggs. The embryos germinate and then grow to be next-generation plants. The endosperms, which are tissues adjacent to the embryos, supply nutrients necessary for the growth of embryos for germination. The structure of each endosperm is divided into an inner endosperm derived from the embryo sac, which is a female gametophyte, and a perisperm derived from a sporophyte tissue. The embryos and endosperms are encapsulated in integuments to form ovules, which mature into seeds. The ovules are exposed in gymnosperms, whereas the ovules are covered with ovaries and the ovaries mature to form fruits in angiosperms.

In the angiosperm, the embryo sac contained in a pistil has an egg apparatus consisting of three cells including three antipodal cells at one end and a single egg cell at the other end. The embryo sac also has two polar nuclei at the center. When the pistil is pollinated, two sperm cells are carried into the embryo sac through a pollen tube extending from pollen, and the two sperm cells are fertilized with the egg cell and two polar nuclei in the embryo sac, respectively (this is called double fertilization). Fertilization of the egg cell (this is called reproductive fertilization) by one of the sperm cells produces a fertilized egg with a nuclear phase of 2n, which divides to form an embryo. Fertilization of two polar nuclei (this is called nutrient fertilization) by the other sperm cell produces an endosperm nucleus with a nuclear phase of 3n, which divides and proliferates to form an endosperm including an inner endosperm in the embryo sac.

In the angiosperm, the endosperm does not develop in many cases unless fertilization (or nutrient fertilization) occurs between sperm cells and two polar nuclei. In some cases, the endosperm may develop even if nutrient fertilization does not occur depending on plant species, plant individuals, and various conditions, although the endosperm developed in such a manner usually has no ability to nurture the embryo generated through fertilization (or reproductive fertilization) between sperm cells and egg cells.

From the viewpoint of improvements in crop productivity, it is desirable that functional endosperms can be artificially induced in seed plants without fertilization. For genes that promote the development of endosperms without fertilization, FIS genes (disclosed in PTL 1: WO2000/016609A), for example, have been developed. Unfortunately, all mutant plants introducing such FIS genes have recessive mutants and only plants having the mutants on the maternal side exhibit the advantages, resulting in poor practical uses.

CITATION LIST

Patent Literatures

PTL 1: WO2000/016609A

SUMMARY OF INVENTION

Problems to be Solved

An object of the present invention is to provide a method of artificially inducing a functional endosperm in a seed plant without fertilization.

Means for Solving Problems

The present inventors have found that endosperm development in seed plants can be induced without fertilization by introducing to express specific genes that play as endosperm development-inducing factors into the genomes of seed plants, and have completed the present invention.

The present invention relates to the following Items:

[1] A nucleic acid molecule for inducing endosperm development in a seed plant without fertilization by being introduced into and expressed in a genome of the seed plant, comprising a base sequence encoding a polypeptide having an endosperm development-inducing function.

[2] The nucleic acid molecule of Item [1], wherein the polypeptide having an endosperm development-inducing function comprises a motif having an amino acid sequence represented by Formula (Ia) or (Ib):

(Ia)
[F/V][K/Q][A/Q]KLRKGLWSPEED[E/D]KL[L/Y]N[H/Y]

I[I/T]RHG[H/V]GCWSSVPKLAGLQRCGKSCRLRWINYLRPDL

KRG[A/S]FSQ[D/Q]EE[D/S]LI[I/V][A/E]LH[A/E]

[A/I]LGNRWSQIA[S/T][H/R]LPGRTDNEIKNFWNSCLKKKL

R[Q/R][K/R]G[I/L]DP[A/T]THKP[I/L]

(Ib)
ERKKGVPWTE[E/D]EH[R/K/L][Q/L/R/S]FL[M/L]GLKK

YG[K/R]GDWRNI[A/S][R/K][N/S/Y]FV[T/I/Q][T/S]

-continued

RTPTQVASHAQKYF[I/L]R[Q/L][V/L/N][N/S/T][G/D]

GKDKRR[S/A]SIHDITTVN[I/L]

[3] The nucleic acid molecule of Item [1] or Item [2], wherein the polypeptide having an endosperm development-inducing function has a sequence homology of 80% or more with an amino acid sequence selected from the group consisting of SEQ ID NOs: 1, 3, 5, 7, 9, 11, 13, 15, 17 and 19.

[4] The nucleic acid molecule of Items [1] to [3], wherein the base sequence encoding the polypeptide having an endosperm development-inducing function has a sequence identity of 80% or more with a base sequence selected from SEQ ID NOs:2, 4, 6, 8, 10, 12, 14, 16, 18 and 20.

[5] The nucleic acid molecule of Items [1] to [4], wherein the nucleic acid molecule further comprises a base sequence encoding a polypeptide having a transcriptional regulatory function, and the base sequence encoding the polypeptide having an endosperm development-inducing function and the base sequence encoding the polypeptide having a transcriptional regulatory function are linked in-frame.

[6] The nucleic acid molecule of Item [5], wherein the polypeptide having a transcriptional regulatory function comprises a motif having an amino acid sequence represented by Formula (IIa), (IIb), (IIc), or (IId):

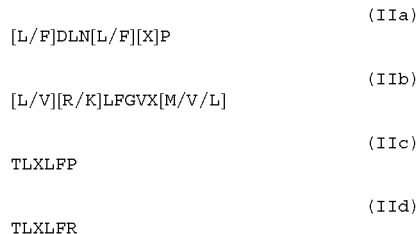

(where X represents any amino acid residue in Formulae (IIa) to (IId)).

[7] The nucleic acid molecule of Item [5] or [6], wherein the polypeptide having a transcriptional regulatory function has a sequence homology of 80% or more with an amino acid sequence selected from the group consisting of SEQ ID NOs: 21, 23, 25 and 27.

[8] The nucleic acid molecule of Items [5] to [7], wherein the base sequence encoding the polypeptide having a transcriptional regulatory function has a sequence identity of 80% or more with a base sequence selected from the group consisting of SEQ ID NOs:22, 24, 26 and 28.

[9] The nucleic acid molecule of Items [1] to [8], wherein the nucleic acid molecule further comprises a base sequence of a promoter region, and the base sequence encoding the polypeptide having an endosperm development-inducing function is functionally linked to the base sequence of the promoter region.

[10] The nucleic acid molecule of Items [1] to [9], wherein the nucleic acid molecule further comprises a base sequence of a terminator region, and the base sequence encoding the polypeptide having an endosperm development-inducing function is functionally linked to the base sequence of the terminator region.

[11] A vector carrying the nucleic acid molecule of Items [1] to [10].

[12] The vector of Item [11], being a plant virus vector or an *Agrobacterium* vector.

[13] A method of producing a transgenic seed plant capable of developing an endosperm without fertilization, comprising introducing to express the nucleic acid molecule of Items [1] to [10] or the vector of Item [11] or [12] into a seed plant cell.

[14] A transgenic seed plant incorporating the nucleic acid molecule of Items [1] to [10] or the vector of Item [11] or [12] into cells.

[15] A transgenic seed plant produced by the method of Item [13].

Advantage of Invention

The present invention facilitates artificial induction of a functional endosperm in a seed plant without fertilization.

BRIEF DESCRIPTION OF DRAWINGS

FIG. 1A is a diagram illustrating amino acid sequence alignments of the polypeptide At5g26660 in *Arabidopsis thaliana* and the polypeptide Os05g0543600 in *Oryza sativa* (SEQ ID NOs: 3 and 13, respectively);

FIG. 1B is a diagram illustrating amino acid sequence alignments of the polypeptides At5g01200, At2g38090 and At5g58900 in *Arabidopsis thaliana* (SEQ ID NOs: 5, 7 and 9, respectively), and the polypeptides Os01g0142500 and Os01g0853700 in *Oryza sativa* (SEQ ID NOs: 15 and 17, respectively);

FIG. 2A is a diagram schematically illustrating the structures of Chimeric genes A to G prepared in Examples 1 to 7;

FIG. 2B is a diagram schematically illustrating the structures of Chimeric genes H to K prepared in Examples 8 to 11;

FIG. 4 shows optical micrographs of pods and ovules in Transformed plant G, the optical micrographs illustrating (a) appearances of pods (shown in comparison to a wild-type plant), (b) the interiors of a pod, and (c1) and (c2) ovules;

FIGS. 8A to 8C show diagrams for explaining the principle of experiments using kokopelli mutants;

FIGS. 9A-9C show optical micrographs (top) and red fluorescent photographs (bottom) of ovules in the plants prepared by crossing pistils of the wild-type plant and Transformed plants A and G yielded through the experiments using the kokopelli mutants with kokopelli pollens;

DESCRIPTION OF EMBODIMENTS

Figure 3:
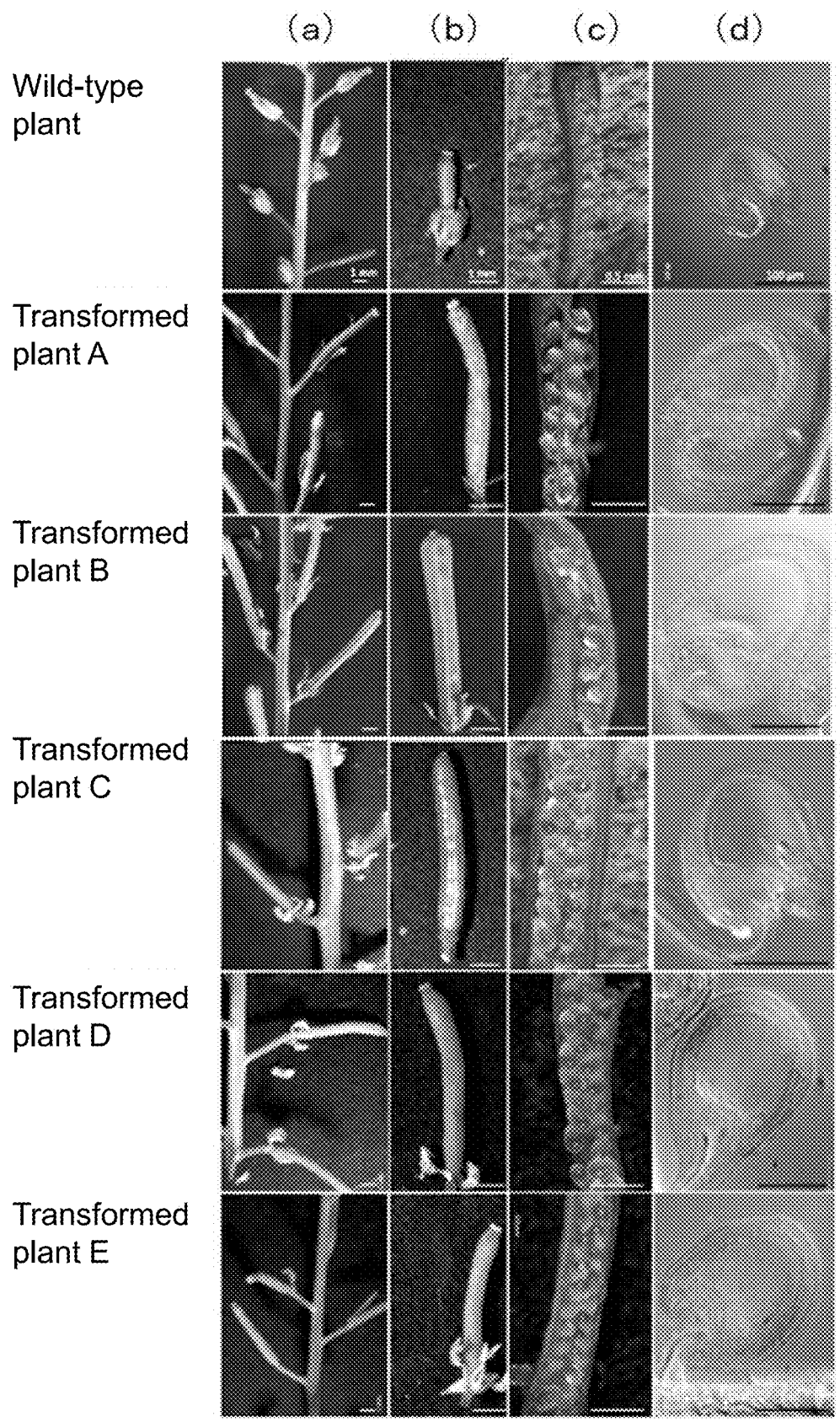
FIG. 3 shows optical micrographs of buds, pods, and ovules in Transformed plants A to E, the optical micrographs illustrating (a) appearances of buds, (b) appearances of pods, (c) the interiors of pods, and (d) ovules.

The present invention will now be described in detail with reference to specific embodiments. However, the present invention is not limited to the following embodiments and can be implemented in any form without departing from the spirit of the present invention.

The patent publications, published unexamined patent applications, and non-patent literatures cited in this specification are incorporated herein by reference in their entirety for all purposes.

[1. Nucleic Acid Molecule and Vector for Inducing Endosperm Development in Seed Plant]

(1-1. Overview)

One aspect of the present invention provides a nucleic acid molecule for inducing endosperm development in a seed plant without fertilization by being introduced into and expressed in a genome of the seed plant (hereinafter, referred to as "the inventive nucleic acid molecule" as appropriate).

The inventive nucleic acid molecule contains a base sequence encoding a polypeptide having an endosperm development-inducing function (hereinafter, referred to as "an endosperm development-inducing polypeptide" as appropriate). The inventive nucleic acid molecule may optionally contain a base sequence encoding a polypeptide having a transcriptional regulatory function (hereinafter, referred to as "a transcriptional regulatory polypeptide" as appropriate). Furthermore, the inventive nucleic acid molecule may optionally contain a promoter region, a terminator region, and any other sequence.

Another aspect of the present invention also provides a vector carrying the inventive nucleic acid molecule (hereinafter, referred to as "the inventive vector" as appropriate).

(1-2. Base sequence encoding endosperm development-inducing polypeptide)

The inventive nucleic acid molecule has a base sequence encoding a polypeptide having an endosperm development-inducing function (or an endosperm development-inducing polypeptide).

In the present invention, the endosperm development-inducing polypeptide preferably has a non-limiting amino acid sequence selected from or similar to the following amino acid sequences:

Amino acid sequence of polypeptide At5g07260 in *Arabidopsis thaliana* (SEQ ID NO: 1)
Amino acid sequence of polypeptide At5g26660 in *Arabidopsis thaliana* (SEQ ID NO: 3)
Amino acid sequence of polypeptide At5g01200 in *Arabidopsis thaliana* (SEQ ID NO: 5)
Amino acid sequence of polypeptide At2g38090 in *Arabidopsis thaliana* (SEQ ID NO: 7)
Amino acid sequence of polypeptide At5g58900 in *Arabidopsis thaliana* (SEQ ID NO: 9)
Amino acid sequence of polypeptide At3g16350 in *Arabidopsis thaliana* (SEQ ID NO: 11)
Amino acid sequence of polypeptide Os05g0543600 in *Oryza sativa* (SEQ ID NO: 13)
Amino acid sequence of polypeptide Os01g0142500 in *Oryza sativa* (SEQ ID NO: 15)
Amino acid sequence of polypeptide Os01g0853700 in *Oryza sativa* (SEQ ID NO: 17)
Amino acid sequence of polypeptide Os04g0569100 in *Oryza sativa* (SEQ ID NO: 19)

As will be understood from Examples described later, the polypeptides At5g07260, At5g26660, At5g01200, At2g38090, At5g58900 and At3g16350 in *Arabidopsis thaliana* and the polypeptides Os05g0543600, Os01g0142500, 0501g0853700 and Os04g0569100 in *Oryza sativa* each have an endosperm development-inducing function when expressed in the plant cells. Accordingly, all the polypeptides can be preferably used as the endosperm development-inducing polypeptides in the present invention.

A polypeptide having an amino acid sequence similar to each of these polypeptides most certainly have very similar effects due to the structural similarity when expressed in the plant cells, and can preferably be used as the endosperm development-inducing polypeptide in the present invention.

Specifically, the amino acid sequence of the endosperm development-inducing polypeptide in the present invention desirably has a sequence homology of at least 80%, preferably at least 85%, at least 90%, at least 95%, at least 96%, at least 97%, or at least 98%, particularly preferably at least 99% with an amino acid sequence selected from the group consisting of SEQ ID NOs: 1, 3, 5, 7, 9, 11, 13, 15, 17 and 19 as described above.

Furthermore, the amino acid sequence of the endosperm development-inducing polypeptide desirably has a sequence identity of at least 80%, preferably at least 85%, at least 90%, at least 95%, at least 96%, at least 97%, or at least 98%, particularly preferably at least 99% with an amino acid sequence selected from the group consisting of SEQ ID NOs: 1, 3, 5, 7, 9, 11, 13, 15, 17 and 19 as described above.

The term "homology" between two amino acid sequences indicates the appearance rate of identical or similar amino acid residues at the respective positions when the two amino acid sequences are aligned, and the term "identity" between the two amino acid sequences indicates the appearance rate of identical amino acid residues at the respective positions when the two amino acid sequences are aligned.

In addition, "homology" and "identity" between two amino acid sequences can be determined by, for example, the Basic Local Alignment Search Tool (BLAST) program (Altschul et al., J. Mol. Biol., (1990), 215(3): 403-10).

The amino acid sequence alignment of the polypeptide At5g26660 in *Arabidopsis thaliana* and the polypeptide Os05g0543600 in *Oryza sativa* (SEQ ID NOs: 3 and 13, respectively) are each shown in FIG. 1A. The amino acid sequence alignments of the polypeptides At5g01200, At2g38090 and At5g58900 in *Arabidopsis thaliana* and the polypeptides Os01g0142500 and Os01g0853700 in *Oryza sativa* (SEQ ID NOs:5, 7, 9, 15 and 17, respectively) are each shown in FIG. 1B. These alignments demonstrate that these polypeptides have high sequence homology with each other.

In particular, it is found that the amino acid sequences of the polypeptide At5g26660 in *Arabidopsis thaliana* and the polypeptide Os05g0543600 in *Oryza sativa* (SEQ ID NOs: 3 and 13, respectively) share a motif having the amino acid sequence represented by Formula (Ia), and the amino acid sequences of the polypeptides At5g01200, At2g38090 and At5g58900 in *Arabidopsis thaliana* and the polypeptides Os01g0142500 and Os01g0853700 in *Oryza sativa* (SEQ ID NOs:5, 7, 9, 15 and 17, respectively) share a motif having the amino acid sequence represented by Formula (Ib):

(Ia)
[F/V][K/Q][A/Q]KLRKGLWSPEED[E/D]KL[L/Y]N[H/Y]

I[I/T]RHG[H/V]GCWSSVPKLAGLQRCGKSCRLRWINYLRPDL

KRG[A/S]FSQ[D/Q]EE[D/S]LI[I/V][A/E]LH[A/E]

[A/I]LGNRWSQIA[S/T][H/R]LPGRTDNEIKNFWNSCLKKKL

R[Q/R][K/R]G[I/L]DP[A/T]THKP[I/L]

(Ib)
ERKKGVPWTE[E/D]EH[R/K/L][Q/L/R/S]FL[M/L]GLKK

YG[K/R]GDWRNI[A/S][R/K][N/S/Y]FV[T/I/Q][T/S]

RTPTQVASHAQKYF[I/L]R[Q/L][V/L/N][N/S/T][G/D]

GKDKRR[S/A]SIHDITTVN[I/L]

In Formulae (Ia) and (Ib), each amino acid residue is represented by a one-letter code. In addition, positions where two or more amino acid residues are displayed separating by slashes (/) in square brackets ([ ]) indicate that one of these amino acid residues is present.

Accordingly, the polypeptides having the motifs represented by Formulae (Ia) and (Ib) most certainly induce endosperm development when expressed in plant cells. Thus, the polypeptides having the motifs represented by Formulae (Ia) and (Ib) can also be preferably used as the endosperm development-inducing polypeptide in the present invention.

The base sequence encoding such an endosperm development-inducing polypeptide preferably has a non-limiting base sequence selected from or similar to the following base sequences:

Base sequence of gene At5g07260 in *Arabidopsis thaliana* (SEQ ID NO: 2)
Base sequence of gene At5g26660 in *Arabidopsis thaliana* (SEQ ID NO: 4)
Base sequence of gene At5g01200 in *Arabidopsis thaliana* (SEQ ID NO: 6)
Base sequence of gene At2g38090 in *Arabidopsis thaliana* (SEQ ID NO: 8)
Base sequence of gene At5g58900 in *Arabidopsis thaliana* (SEQ ID NO: 10)
Base sequence of gene At3g16350 in *Arabidopsis thaliana* (SEQ ID NO: 12)
Base sequence of gene Os05g0543600 in *Oryza sativa* (SEQ ID NO: 14)
Base sequence of gene Os01g0142500 in *Oryza sativa* (SEQ ID NO: 16)
Base sequence of gene Os01g0853700 in *Oryza sativa* (SEQ ID NO: 18)
Base sequence of gene Os04g0569100 in *Oryza sativa* (SEQ ID NO: 20)

Specifically, the base sequence encoding the endosperm development-inducing polypeptide in the present invention has a sequence identity of at least 80%, preferably at least 85%, at least 90%, at least 95%, at least 96%, at least 97%, or at least 98%, particularly preferably at least 99% with a base sequence selected from the group consisting of SEQ ID NOs: 2, 4, 6, 8, 10, 12, 14, 16, 18 and 20 as described above.

The sequence identity between two base sequences can be determined using the Needleman-Wunsch algorithm (Needleman and Wunsch, 1970, J. Mol. Biol. 48: 443-453) by, for example, the Needle program of the EMBOSS package, preferably version 5.00 or higher (EMBOSS: The European Molecular Biology Open Software Suite, Rice et al., 2000, Trends Genet. 16: 276-277).

(1-3. Base Sequence Encoding Transcriptional Regulatory Polypeptide)

The inventive nucleic acid molecule preferably has a base sequence encoding a polypeptide having a transcriptional regulatory function (i.e., a transcriptional regulatory polypeptide) in addition to the base sequence encoding the endosperm development-inducing polypeptide described above. In this case, it is preferred that the base sequence encoding the endosperm development-inducing polypeptide and the base sequence encoding the transcriptional regulatory polypeptide be linked in-frame.

In the present invention, the transcriptional regulatory polypeptide preferably has a non-limiting amino acid sequence selected from or similar to the following amino acid sequences:

Amino acid sequence of SRDX polypeptide produced by modification of the transcriptional regulatory region of gene SUPERMAN in *Arabidopsis thaliana* (SEQ ID NO: 21)
Amino acid sequence of the transcriptional regulatory region BRD polypeptide of gene At2g36080 in *Arabidopsis thaliana* (SEQ ID NO: 23)
Amino acid sequence of the transcriptional regulatory region WUS-box polypeptide of gene WUSCHEL in *Arabidopsis thaliana* (SEQ ID NO: 25)
Amino acid sequence of the transcriptional regulatory region L2R polypeptide of gene AtMYBL2 in *Arabidopsis thaliana* (SEQ ID NO: 27)

The SRDX, BRD, WUS-box, and L2R polypeptides described above are expression products of transcriptional regulatory domains used in the Chimeric repressor silencing technology (CRES-T) developed by the present inventors. Specifically, the SRDX polypeptide, the BRD polypeptide, the WUS-box polypeptide, and the L2R polypeptide are described in detail in, for example, WO2003/055993A, JP2009-213426 A, Ikeda et al., Plant Cell, (2009), 21:3493-3505, and Matsui et al., Plant J., (2008), 55:954-967, respectively.

When the base sequences encoding these SRDX, BRD, WUS-box, and L2R polypeptides are linked in-frame with the endosperm development-inducing polypeptide described above and then introduced to be expressed into plant cells, the induction of endosperm development can be enhanced in the endosperm development-inducing polypeptide. Accordingly, all these polypeptides can be suitably used as the transcriptional regulatory polypeptide in the present invention.

In addition, a polypeptide having an amino acid sequence similar to each of these polypeptides most certainly has identical effects due to the structural similarity when expressed in plant cells, and thus can be suitably used as the transcriptional regulatory polypeptide in the present invention.

Specifically, the amino acid sequence of the transcriptional regulatory polypeptide in the present invention desirably has a sequence homology of at least 80%, preferably at least 85%, at least 90%, at least 95%, at least 96%, at least 97%, or at least 98%, particularly preferably at least 99% with an amino acid sequence selected from the group consisting of SEQ ID NOs: 21, 23, 25 and 27 as described above.

The amino acid sequence of the transcriptional regulatory polypeptide desirably has a sequence identity of at least 80%, preferably at least 85%, at least 90%, at least 95%, at least 96%, at least 97%, or at least 98%, particularly preferably at least 99% with an amino acid sequence selected from the group consisting of SEQ ID NOs: 21, 23, 25 and 27 described above.

It is known that the SRDX, BRD, WUS-box, and L2R polypeptides each have a motif having an amino acid sequence represented by Formula (IIa), (IIb), (IIc), or (IId) and that these motifs each play an important role in the transcriptional regulatory function. Accordingly, a polypeptide containing a motif having an amino acid sequence represented by Formula (IIa), (IIb), (IIc), or (IId) can also be suitably used as a transcriptional regulatory polypeptide:

[L/F]DLN[L/F][X]P          (IIa)

[L/V][R/K]LFGVX[M/V/L]     (IIb)

TLXLFP                      (IIc)

TLXLFR                      (IId)

In Formulae (IIa) to (IId), each amino acid residue is represented by a one-letter code. In addition, positions where two or more amino acid residues are displayed separating by slashes (/) in square brackets ([ ]) indicate that one of these amino acid residues is present. X represents any amino acid residue.

The base sequence encoding such a transcriptional regulatory polypeptide preferably has a non-limiting base sequence selected from or similar to the following base sequences:

Base sequence of SRDX produced by modification of the transcriptional regulatory region of gene SUPERMAN (SEQ ID NO: 22)

Base sequence of the transcriptional regulatory region BRD of gene At2g36080 (SEQ ID NO: 24)

Base sequence of the transcriptional regulatory region WUS-box of gene WUSCHEL (SEQ ID NO: 26)

Base sequence of the transcriptional regulatory region L2R of gene AtMYBL2 (SEQ ID NO: 28)

Specifically, the base sequence encoding the transcriptional regulatory polypeptide in the present invention desirably has a sequence identity of at least 80%, preferably at least 85%, at least 90%, at least 95%, at least 96%, at least 97%, or at least 98%, particularly preferably at least 99% with an amino acid sequence selected from the group consisting of SEQ ID NOs: 22, 24, 26 and 28 as described above.

(1-4. Promoter Region)

The inventive nucleic acid molecule preferably has a promoter region. It is preferred that the promoter region be usually located at the 5' side of the base sequence encoding the endosperm development-inducing polypeptide so as to be functionally linked to the endosperm development-inducing polypeptide.

The promoter region may be a promoter derived from a virus, from a microorganism, from a plant, or from any other organism.

With the functional site, the promoter may be a promoter that functions in the entire plant or only in the peripheral sites including a female gametophyte and its progenitor cells. It may further be a promoter that specifically functions during treatment with specific chemicals or under a specific growth environment.

The promoter region may have any base sequence. For example, the promoter regions have any base sequence among the following promoters:

35S promoter of Cauliflower mosaic virus (CaMV) (SEQ ID NO: 29)

Promoter of gene At5g07260 in *Arabidopsis thaliana* (SEQ ID NO: 30)

Promoter of gene At5g26660 in *Arabidopsis thaliana* (SEQ ID NO: 31)

Promoter of gene At5g01200 in *Arabidopsis thaliana* (SEQ ID NO: 32)

Promoter of gene At2g38090 in *Arabidopsis thaliana* (SEQ ID NO: 33)

Promoter of gene At5g58900 in *Arabidopsis thaliana* (SEQ ID NO: 34)

Promoter of gene At3g16350 in *Arabidopsis thaliana* (SEQ ID NO: 35)

Promoter of actin gene in *Oryza sativa* (SEQ ID NO: 36)

Promoter of ubiquitin 1 gene in *Zea mays* (SEQ ID NO: 37)

Promoter of gene Os05g0543600 in *Oryza sativa* (SEQ ID NO: 38)

Promoter of gene Os01g0142500 in *Oryza sativa* (SEQ ID NO: 39)

Promoter of FST gene in *Oryza sativa* (SEQ ID NO: 40)

Promoter of gene Os01g0853700 in *Oryza sativa* (SEQ ID NO: 41)

Promoter of gene Os04g0569100 in *Oryza sativa* (SEQ ID NO: 42)

A promoter composed of a base sequence having an identity of at least 80%, preferably at least 85%, or at least 90%, at least 95%, at least 96%, at least 97%, at least 98%, particularly preferably at least 99% with each base sequence of SEQ ID NOs: 29 to 42 can also be preferably used as the promoter region in the inventive nucleic acid molecule.

(1-5. Terminator Region)

The inventive nucleic acid molecule preferably has a terminator region. It is preferred that the terminator region be usually located at the 3' side of the base sequence encoding the endosperm development-inducing polypeptide so as to be functionally linked to the endosperm development-inducing polypeptide.

The terminator region may be a terminator derived from a virus, from a plant, or from any other organism.

With the functional site, the terminator may be a terminator that functions in the entire plant, or a terminator that functions only in the peripheral parts including a female gametophyte and its progenitor cell. It may further be a terminator that specifically functions during treatment with specific chemicals or under a specific growth environment.

The terminator region may have any base sequence. For example, the terminator regions have any base sequence of the following terminators:

Terminator of the nopaline synthase gene in *Agrobacterium* (SEQ ID NO: 43)

Terminator of the heat shock protein gene in *Arabidopsis thaliana* (SEQ ID NO: 44)

A terminator composed of a base sequence having an identity of at least 80%, preferably at least 85%, or at least 90%, at least 95%, at least 96%, at least 97%, at least 98%, particularly preferably at least 99% with each base sequence of SEQ ID NO: 43 or 44 can also be preferably used as a terminator region in the inventive nucleic acid molecule.

(1-6. Other Genetic Elements)

The inventive nucleic acid molecule may have one or more other genetic element. Examples of the other genetic elements include antibiotic resistance genes, restriction enzyme sequences, and homologous recombinant sequences.

(1-7. Structure of Nucleic Acid)

The inventive nucleic acid molecule has a base sequence encoding the endosperm development-inducing polypeptide described above, and preferably has an optional base sequence encoding a transcriptional regulatory polypeptide, an optional promoter region, an optional terminator region and/or any other genetic element. In particular, if the inventive nucleic acid molecule has optional elements other than the base sequence encoding the endosperm development-inducing polypeptide, the base sequence encoding the transcriptional regulatory polypeptide is usually linked in-frame with the base sequence encoding the endosperm-inducing polypeptide. At the same time, the promoter region is located at the 5' side of the base sequence encoding the endosperm development-inducing polypeptide while the transcriptional regulatory region and/or the terminator region is located at the 3' side of the base sequence encoding the endosperm development-inducing polypeptide, where these regions are each functionally linked to the base sequence encoding the endosperm development-inducing polypeptide. After the inventive nucleic acid molecule is introduced into plant cells of seed plants, preferably incorporated into genomes, these genetic elements are in functional cooperation with each other and the endosperm development-inducing polypeptide is autonomously expressed. In other words, the inventive nucleic acid molecule preferably functions as a chimeric gene cassette.

(1-8. Vector)

The inventive nucleic acid molecule is usually carried in the vector to be introduced into plant cells and incorporated into genomes.

Such a vector (the inventive vector) may have any form, i.e., a linear or circular form. Particularly preferred is a circular form, such as a plasmid form. Specific examples of the vectors include plant virus vectors and *Agrobacterium* vectors.

A method using the plant virus vector comprises in-vitro transcription of cDNA in a plant virus genome into which a target gene is inserted; inoculation of the resulting RNA as a vector into a plant to be infected therewith; and expression of the target gene in the plant by the proliferative capacity and systemic transfer ability of the virus itself. Examples of plant virus vectors include cauliflower mosaic virus (CaMV) vectors, cucumber mosaic virus (CMV) vectors, tobacco mosaic virus (TMV) vectors, and potato X virus (PVX) vectors.

A method using the *Agrobacterium* vector (T-DNA vector) is based on a technique using a transfer DNA (T-DNA) sequence of a Ti plasmid of *Agrobacterium*. The T-DNA sequence has a right border sequence (RB sequence) and a left border sequence (LB sequence) at two ends and incorporates genes in the region between these sequences into plant genomes. A T-DNA binary system in a combination of two plasmids, that is, a binary plasmid and a helper plasmid, through modification of Ti plasmid has already been established, and extensively used in introduction of foreign genes by genetic transformation of plants.

The inventive nucleic acid molecule is preferably carried on the vector such that the base sequence encoding the inventive endosperm development-inducing polypeptide is incorporated into plant genomes and functionally expressed.

In the case that the inventive nucleic acid molecule has a promoter region and a terminator region in addition to the base sequence encoding the endosperm development-inducing polypeptide and functions as a chimeric gene cassette that can be autonomously expressed in plant cells, the vector does not necessarily have regulatory elements, such as promoters and terminators, and needs to have only the elements necessary for incorporation into plant genomes (e.g., flanking sequences for homologous recombination, or LB sequence and RB sequence of T-DNA).

In contrast, in the case that the inventive nucleic acid molecule has no promoter region and no terminator region and functions as a chimeric gene cassette that can be autonomously expressed in plant cells, the vector preferably has not only the elements necessary for the incorporation into plant genomes but also regulatory elements, such as promoters and terminators, so as to induce the expression of the endosperm development-inducing polypeptide contained in the inventive nucleic acid molecule. Alternatively, when the inventive vector may be incorporated into plant genomes, the base sequence encoding the endosperm development-inducing polypeptide contained in the inventive nucleic acid molecule is functionally linked and cooperated with regulatory elements, such as promoters and terminators, in plant genomes such that the endosperm-inducing polypeptide is expressed.

The inventive vector may be used in combination with any other helper plasmid as needed. Examples of the other helper plasmid include helper plasmids having a vir region for a T-DNA vector.

The inventive vector can be readily produced by appropriate combination of various gene recombination techniques well known to those skilled in the art.

[2. Transgenic Seed Plant Capable of Developing Endosperm without Fertilization and Method of Producing Transgenic Seed Plant]

Another aspect in the present invention provides a method of producing a transgenic seed plant that can develop an endosperm without fertilization (hereinafter, referred to as "the inventive method").

The inventive method comprises introducing to express the inventive nucleic acid molecule or the inventive vector described above into the genome of a seed plant. Two or more inventive nucleic acid molecules or inventive vectors may be used in combination.

The target seed plants are, not limited to, usually angiosperms. Non-limiting examples of the angiosperms include plant species belonging to, for example, Solanaceae, Fabaceae, Brassicaceae, Gramineae, Asteraceae, Nelumbonaceae, Rosaceae, Cucurbitaceae, and Liliaceae. Specific examples include tobacco, *Arabidopsis thaliana*, alfalfa, barley, kidney bean, canola, cowpea, cotton, corn, clover, lotus, lentil, *Lupinus*, millet, oats, pea, peanut, rice, rye, sweet clover, sunflower, sweet pea, soybean, sorghum, triticale, jicama, velvet bean, broad bean, wheat, *wisteria*, nut plants, redtop, leek, snapdragon, celery, groundnut, asparagus, *Scopolia japonica, Avena fatua*, hedge bamboo, oilseed rape, bromegrass, bush violet, *camellia*, hemp, red pepper, chickpea, *chenopodium*, witloof, citrus, coffee tree, job's tears, cucumber, pumpkin, Bermuda grass, duckweed, *datura*, urimibae, *digitalis*, Japanese yam, oil palm, *oleander*, fescue, strawberry, geranium, day-lily, para rubber tree, henbane, sweet potato, lettuce, Lens *esculenta*, lily, linseed, ryegrass, tomato, *origanum*, apple, mango, cassava, *Medicago polymorpha*, African linaria, sainfoin, geranium, Chinese fountain grass, *petunia*, garden pea, green bean, timothy, bluegrass, cherry tree, buttercup, radish, currant, castor oil plant, raspberry, sugar cane, salpiglossis, *Senecio*, *Setaria*, white mustard, eggplant, sorghum, Stenotaphrum *secundatum*, cacao, *Trifolium*, blue melilot, wheat, and grape. Among these plants are preferred *Arabidopsis thaliana*, rice, corn, wheat and barley, and fruits.

The inventive nucleic acid molecule or the inventive vector described above may be introduced into the genomes of seed plants by any method. For example, the inventive vector may be biologically transmitted to seed plants or introduced into tissues of seed plants by, for example, an agroinfiltration process, a PEG-calcium phosphate process, an electroporation process, a liposome process, a particle gun process, and a microinjection process, to be incorporated into the genomes of seed plants. Alternatively, the inventive nucleic acid molecule may be directly incorporated into the genomes of plants by a known process, such as a CRISPR/Cas9 system, without use of the inventive vector. In an alternative process, the inventive nucleic acid molecule or the inventive vector is introduced into a tissue fragment of a seed plant to cultivate the tissue fragment into a plant that is a re-differentiated individual having a genome into which the inventive vector is introduced and constantly expressing the inventive nucleic acid molecule.

The inventive method described above can incorporate the inventive nucleic acid molecule containing the base sequence encoding the endosperm development-inducing polypeptide into the genomes to yield a transgenic plant expressing the endosperm development-inducing polypeptide. Such a transgenic plant can develop an endosperm without fertilization by expression of the endosperm-inducing polypeptide. It is noted that the resultant endosperm is a functional endosperm that can nurture an embryo different from a non-functional endosperm that develops in a conventional unfertilized plant.

The subject plants of the present invention include transgenic seed plants produced by the inventive method described above, transgenic seed plants containing the inventive nucleic acid molecules or the inventive vectors in their genomes, transgenic seed plants capable of developing functional endosperms without fertilization, and progenies or fragments of those plants. The term "progeny of plant" refers to a progeny produced by sexual or asexual reproduction of the plant and includes a clone of the plant. For example, the progeny of the plant can be produced from proliferation materials (e.g., seeds, fruits, ears, tubers, root tubers, stumps, calluses, and protoplasts) of the plant or its progeny. In the present invention, the term "plant or progeny, or part thereof" indicates a seed (including germinated seed or immature seed), an organ or part thereof (including leaf, root, stem, flower, stamen, pistil, and fragment thereof), plant cultured cells, callus, and protoplast in the plant or its progeny plant.

EXAMPLES

The present invention will now be described in more detail with reference to Examples. It should be noted that the present invention is not limited to the following Examples and can be implemented in any form without departing from the spirit of the present invention. In primer base sequences described below where capital and small letters are mixed, the capital letters indicate regions complementary to the base sequence in the target genes for amplification whereas small letters indicate additional sequences.

[Overview]

In Example 1, a gene fragment encoding SRDX, which was a transcriptional regulatory domain, was directly linked to the gene At5g07260, and the product was linked with the promoter cauliflower mosaic virus (CAMV) 35S such that the linked gene fragment operated downstream of the promoter CAMV 35S to produce a transforming plasmid (Construct A) having the chimeric gene ProCaMV 35S: At5g07260SRDX (Chimeric gene A). Construct A was then introduced into an *Arabidopsis thaliana* plant, and the effect of Construct A on the promotion of spontaneous endosperm development in *Arabidopsis thaliana* was determined by the morphological observation of the resultant transformed plant and the analysis of the ability to nurture the fertilized embryo.

In Example 2, a gene fragment encoding SRDX, which was a transcriptional regulatory domain, was directly linked to the gene At5g26660, and the product was linked with the promoter CAMV 35S such that the linked gene fragment operated at the promoter CAMV 35S to produce a transforming plasmid (Construct B) having the chimeric gene ProCaMV 35S:At5g26660SRDX (Chimeric gene B). Construct B was then introduced into an *Arabidopsis thaliana* plant, and the effect of Construct B on the promotion of spontaneous endosperm development in *Arabidopsis thaliana* was determined by the morphological observation of the resultant transformed plant.

In Example 3, a gene fragment encoding SRDX, which was a transcriptional regulatory domain, was directly linked to the gene At5g01200, and the product was linked with the promoter CAMV 35S such that the linked gene fragment operated downstream of the promoter CAMV 35S to produce a transforming plasmid (Construct C) having the chimeric gene ProCaMV 35S:At5g01200SRDX (Chimeric gene C). Construct C was then introduced into an *Arabidopsis thaliana* plant, and the effect of Construct C on the promotion of spontaneous endosperm development in *Arabidopsis thaliana* was determined by the morphological observation of the resultant transformed plant and the analysis of the ability to nurture the fertilized embryo.

In Example 4, a gene fragment encoding SRDX, which was a transcriptional regulatory domain, was directly linked to the gene At2g38090, and the product was linked with the promoter CAMV 35S such that the linked gene fragment operated downstream of the promoter CAMV 35S to produce a transforming plasmid (Construct D) having the chimeric gene ProCaMV 35S:At2g38090SRDX (Chimeric gene D). Construct D was then introduced into an *Arabidopsis thaliana* plant, and the effect of Construct D on the promotion of spontaneous endosperm development in *Arabidopsis thaliana* was determined by the morphological observation of the resultant transformed plant.

In Example 5, a gene fragment encoding SRDX, which was a transcriptional regulatory domain, was directly linked to gene At5g58900, and the product was linked with the CAMV 35S promoter such that the linked gene fragment operated downstream of the promoter CAMV 35S to produce a transforming plasmid (Construct E) having the chimeric gene ProCaMV 35S:At5g58900SRDX (Chimeric gene E). Construct E was then introduced into an *Arabidopsis thaliana* plant, and the effect of Construct E on the promotion of spontaneous endosperm development in *Arabidopsis thaliana* was determined by the morphological observation of the resultant transformed plant.

In Example 6, a gene fragment encoding SRDX, which was a transcriptional regulatory domain, was directly linked to the gene At3g16350, and the product was linked with the promoter CAMV 35S such that the linked gene fragment operated downstream of the promoter CAMV 35S to produce a transforming plasmid (Construct F) having the chimeric gene ProCaMV 35S: At3g16350SRDX (Chimeric gene F). Construct F was then introduced into an *Arabidopsis thaliana* plant, and the effect of Construct F on the promotion of spontaneous endosperm development in *Arabidopsis thaliana* was determined by the morphological observation of the resultant transformed plant and the analysis of the ability to nurture the fertilized embryo.

In Example 7, a gene fragment encoding SRDX, which was a transcriptional regulatory domain, was directly linked to the gene At5g01200, and the product was linked with the promoter At5g01200 such that the linked gene fragment operated downstream of the promoter At5g01200 to produce a transforming plasmid (Construct G) having the chimeric gene ProAt5g01200: At5g01200SRDX (Chimeric gene G). Construct G was then introduced into an *Arabidopsis thaliana* plant, and the effect of Construct F on the promotion of spontaneous endosperm development in *Arabidopsis thaliana* was determined by the morphological observation of the resultant transformed plant and the analysis of the ability to nurture the fertilized embryo.

In Example 8, a gene fragment encoding SRDX, which was a transcriptional regulatory domain, was directly linked to the gene Os05g0543600, and the product was linked with the promoter *Zea mays* UBQ1 such that the linked gene fragment operated downstream of the promoter *Zea mays* UBQ1 to produce a transforming plasmid (Construct H) having the chimeric gene ProZmUBQ1: Os05g0543600SRDX (Chimeric gene H). Construct H was then introduced into an *Oryza sativa* callus, and the effect of Construct H on the promotion of spontaneous endosperm development in *Oryza sativa* was determined by the morphological observation of the resultant transformed plant.

In Example 9, a gene fragment encoding SRDX, which was a transcriptional regulatory domain, was directly linked to the gene Os01g0142500, and the product was linked with the promoter *Zea mays* UBQ1 such that the linked gene fragment operated downstream of the promoter *Zea mays* UBQ1 to produce a transforming plasmid (Construct I) having the chimeric gene ProZmUBQ1: Os01g0142500SRDX (Chimeric gene I). Construct I was then introduced into an *Oryza sativa* callus, and the effect of Construct I on the promotion of spontaneous endosperm development in *Oryza sativa* was determined by the morphological observation of the resultant transformed plant.

In Example 10, a gene fragment encoding SRDX, which was a transcriptional regulatory domain, was directly linked to the gene Os01g0853700, and the product was linked with the promoter *Oryza sativa* FST such that the linked gene fragment operated downstream of the promoter *Oryza sativa* FST to produce a transforming plasmid (Construct J) having the chimeric gene ProOsFST:Os01g0853700SRDX (Chimeric gene J). Construct J was then introduced into an *Oryza sativa* callus, and the effect of Construct J on the promotion of spontaneous endosperm development in *Oryza sativa* was determined by the morphological observation of the resultant transformed plant.

In Example 11, a gene fragment encoding SRDX, which was a transcriptional regulatory domain, was directly linked to the gene Os04g0569100, and the product was linked with the promoter *Oryza sativa* FST such that the linked gene fragment operated downstream of the promoter *Oryza sativa* FST to produce a transforming plasmid (Construct K) having the chimeric gene ProOsFST:Os04g0569100SRDX (Chimeric gene K). Construct K was then introduced into an *Oryza sativa* callus, and the effect of Construct K on the promotion of spontaneous endosperm development in *Oryza sativa* was determined by the morphological observation of the resultant transformed plant.

[Example 1] Production of Construct A (ProCaMV 35S:At5g07260SRDX) for Transformation and *Arabidopsis thaliana* Plant Transformation (1-1) Production of Construct A (a) Construction of Plasmid pBIG2

The transforming vector pBIG-HYG (Becker, Nucleic Acid Research, (1990), 18(1):203) transferred from Michigan State University, USA, was cleaved with restriction enzymes HindIII and SstI, and the cleaved product was subjected to agarose gel electrophoretic separation to recover a pBIG-HYG DNA fragment not including GUS genes.

Similarly, the plasmid p35S-GFP (Clontech Laboratories Inc., USA) was cleaved with restriction enzymes HindIII and BamHI, and the cleaved fragments were subjected to agarose gel electrophoretic separation to recover a DNA fragment containing a CAMV 35S promoter (hereinafter, referred to as "ProCaMV 35S" as appropriate).

DNAs having the base sequences of SEQ ID NOs: 45 and 46 described below were synthesized by a conventional process, were heated at 70° C. for ten minutes, and then were annealed by natural cooling to yield a double-stranded DNA. This DNA fragment has a sequence where the restriction enzyme site BamHI and the restriction enzyme sites SmaI and SalI are linked to the 5' end and the 3' end, respectively, of the omega sequence derived from a tobacco mosaic virus (TMV) that enhances the translation efficiency. The use of this sequence can increase the expression efficiency of the gene present at the 3' side and introduce restriction enzyme sites essential for subsequent construction of plasmid.

```
                                       (SEQ ID NO: 45)
5'-GATCCACAATTACCAACAACAACAAACAA

CAAACAACATTACAATTACAGATCCCGGGGGT

ACCGTCGACGAGCT-3'

(SEQ ID NO: 46)
5'-CGTCGACGGTACCCCCGGGATCTGTAATT

GTAATGTTGTTTGTTGTTTGTTGTTGTTGGTA

ATTGTG-3'
```

The DNA fragment containing the ProCaMV 35S and the double-stranded DNA as synthesized above were inserted into the HindIII and SstI sites, respectively, of pBIG-HYG not including the GUS genes to produce a vector carrying ProCaMV 35S for transformation of plants. This vector is referred to as "plasmid pBIG2".

(b) Construction of Plasmid p35SRDX

Two complementary DNA fragments having the base sequences of SEQ ID NOs: 47 and 48 as described below were produced where GGG and a stop codon were attached to the 5' end and the 3' end, restrictively, of the base sequence of SRDX, which was the transcriptional regulatory domain of the gene SUPERMAN in *Arabidopsis thaliana*.

(SEQ ID NO: 47)
5'-GGGCTCGATCTGGATCTAGAACTCCGTTTGGGTTTCGCTTAAG-3'

(SEQ ID NO: 48)
5'-CTTAAGCGAAACCCAAACGGAGTTCTAGATCCAGATCGAGCCC-3'

These synthesized DNA fragments were annealed and inserted into the plasmid pBIG2, which was produced by cleavage with the restriction enzyme SmaI. The products were sequenced to screen a plasmid containing the SRDX introduced in the forward direction. This plasmid is referred to as "plasmid p35SRDX".

(c) Production of Plasmid 35S:At5g07260SRDX (Construct A)

The cDNA of the gene At5g07260 in *Arabidopsis thaliana* as a template was subjected to the polymerase chain reaction (PCR) with a 5' end upper primer having the base sequence of SEQ ID NO: 49 described below and a 3' end lower primer having the base sequence of SEQ ID NO: 50 described below to amplify a partial sequence where the stop codon was removed from the full-length sequence of the gene At5g07260.

(SEQ ID NO: 49)
5'-gATGTATCATCATCTTCAAACGAGGATTTT-3'

(SEQ ID NO: 50)
5'-ACGGTGGACTGGAAGAGCATTTTGGACATT-3'

The PCR was repeated 30 cycles, each cycle including a denaturing reaction at 94° C. for one minute, an annealing reaction at 50° C. for one minute, and an extending reaction at 72° C. for three minutes.

The resultant amplification product without the stop codon of the gene At5g07260 was cleaved with SmaI, recovered by agarose gel electrophoresis, and inserted into the plasmid p35SRDX described above by a conventional process. The resulting plasmids were sequenced by a conventional method to screen a specific plasmid that coincided with the gene At5g07260 in a reading frame of SRDX from the plasmids containing the gene At5g07260 introduced in the forward direction.

The resultant plasmid for transformation carries the chimeric gene ProCaMV 35S:At5g07260SRDX where the promoter ProCaMV 35S, the gene At5g07260, and the transcriptional regulatory domain SRDX are operably linked. This plasmid is abbreviated as "Construct A" as appropriate, and the chimeric gene ProCaMV 35S:At5g07260SRDX carried on Construct A is abbreviated as "Chimeric gene A" as appropriate. The schematic structure of Chimeric gene A is shown in FIG. 2A.

(1-2) Development of Transformed Plant A

The *Arabidopsis thaliana* plants were transformed with Construct A by the method described in "Transformation of *Arabidopsis thaliana* by vacuum infiltration" (website bch.msu.edu/pamgreen/protocol). In this case, simple soaking without vacuum was used for transmission. Construct A was introduced into a soil bacterium (*Agrobacterium tumefaciens*) strain GV3101 (C58C1Rifr) pMP90 (Gmr) (koncz and Schell, Molecular and General Genetics, (1986), 204 [3]:383-396) by electroporation. The bacteria were cultivated in 250 mL of LB medium for two days.

The bacterial cells were then collected from the culture solution and suspended in an infiltration medium (500 mL). *Arabidopsis thaliana* that had grown for 14 days was immersed in the solution for one minute, and then allowed to be regrown for seeding. The collected seeds were sterilized with 50% bleach and 0.02% Triton X-100 solution for seven minutes and then rinsed three times with sterile water, and the sterilized seeds were plated onto ½MS selective medium containing 30 mg/l hygromycin. Plants successfully transformed with Construct A acquired hygromycin resistance. The transgenic plants that grew in the hygromycin medium described above were screened and replanted to grow in a soil. The plant transformed with Construct A is abbreviated as "Transformed plant A" as appropriate.

[Example 2] Production of Construct B (ProCaMV 35S:At5g26660SRDX) for Transformation and *Arabidopsis thaliana* Plant Transformation (2-1) Production of Construct B The cDNA of the gene At5g26660 in *Arabidopsis thaliana* as a template was subjected to the PCR with a 5' end upper primer having the base sequence of SEQ ID NO: 51 described below and a 3' end lower primer having the base sequence of SEQ ID NO: 52 described below as in [Example 1] (1-1) (b) to amplify a partial sequence where the stop codon was removed from the gene At5g26660.

(SEQ ID NO: 51)
5'-gATGGGAAGACATTCTTGTTGTTTTAAGCA-3'

(SEQ ID NO: 52)
5'-AAGGCTCTGATCAAACACCATGTTATTAAG-3'

The resultant amplification product without the stop codon of the gene At5g26660 was cleaved with SmaI, was recovered by agarose gel electrophoresis, and was inserted into the plasmid p35SRDX having the promoter CaMV 35S and the transcriptional regulatory domain SRDX prepared in [Example 1] (1-1) (a) and (b) by a conventional process. The resulting plasmids were sequenced by a conventional method to screen a specific plasmid that coincided with the gene At5g26660 in a reading frame of SRDX from the plasmids containing the gene At5g26660 introduced in the forward direction.

The resultant plasmid for transformation carries the chimeric gene ProCaMV 35S:At5g26660SRDX where the promoter ProCaMV 35S, the gene At5g26660, and the transcriptional regulatory domain SRDX are operably linked. This plasmid is abbreviated as "Construct B" as appropriate, and the chimeric gene ProCaMV 35S:At5g26660SRDX carried on Construct B is abbreviated as "Chimeric gene B" as appropriate. The schematic structure of Chimeric gene B is shown in FIG. 2A.

(2-2) Development of Transformed Plant B by Transformation with Construct B

The *Arabidopsis thaliana* plants were transformed with Construct B as in [Example 1] (1-2), and plants successfully transformed were screened with a hygromycin medium. The resultant plant transformed with Construct B is abbreviated as "Transformed plant B" as appropriate.

[Example 3] Production of Construct C (ProCaMV 35S:At5g01200SRDX) for Transformation and *Arabidopsis thaliana* Plant Transformation (3-1) Production of Construct C The cDNA of the gene At5g01200 in *Arabidopsis thaliana* as a template was subjected to the PCR with a 5' end upper primer having the base sequence of SEQ ID NO: 53 described below and a 3' end lower primer having the base sequence of SEQ ID NO: 54 described below as in [Example 1] (1-1) (b) to amplify a partial sequence where the stop codon was removed from the gene At5g01200.

(SEQ ID NO: 53)
5'-gATGTCATCGTCGACGATGTACAGAGGAGT-3'

(SEQ ID NO: 54)
5'-ACTCCACTGCGGAAACGCATTATAATAGCT-3'

The resultant amplification product without the stop codon of the gene At5g01200 was cleaved with SmaI, recovered by agarose gel electrophoresis, and inserted into the plasmid p35SRDX having the promoter CaMV 35S and the transcriptional regulatory domain SRDX prepared in [Example 1] (1-1) (a) and (b) by a conventional process. The resulting plasmids were sequenced by a conventional method to screen a specific plasmid that coincided with the gene At5g01200 in a reading frame of SRDX from the plasmids containing the gene At5g01200 introduced in the forward direction.

The resultant plasmid for transformation carries the chimeric gene ProCaMV 35S:At5g01200SRDX where the promoter ProCaMV 35S, the gene At5g01200, and the transcriptional regulatory domain SRDX are operably linked. This plasmid is abbreviated as "Construct C" as appropriate, and the chimeric gene ProCaMV 35S:At5g01200SRDX carried on Construct C is abbreviated as "Chimeric gene C" as appropriate. The schematic structure of Chimeric gene C is shown in FIG. 2A.

(3-2) Development of Transformed Plant C by Transformation with Construct C

The *Arabidopsis thaliana* plants were transformed with Construct C as in [Example 1] (1-2), and plants successfully transformed were screened with a hygromycin medium. The resultant plant transformed with Construct C is abbreviated as "Transformed plant C" as appropriate.

[Example 4] Production of Construct D (ProCaMV 35S:At2g38090SRDX) for Transformation and *Arabidopsis thaliana* Plant Transformation (4-1) Production of Construct D The cDNA of the gene At2g38090 in *Arabidopsis thaliana* as a template was subjected to the PCR with a 5' end upper primer having the base sequence of SEQ ID NO: 55 described below and a 3' end lower primer having the base sequence of SEQ ID NO: 56 described below as in [Example 1] (1-1) (b) to amplify a partial sequence where the stop codon was removed from the gene At2g38090.

(SEQ ID NO: 55)
5'-gATGAACAGAGGAATCGAAGTTATGTCACC-3'

(SEQ ID NO: 56)
5'-CATTTGGAGATACGCATTGTACGATTCGAA-3'

The resultant amplification product without the stop codon of the gene At2g38090 was cleaved with SmaI, was recovered by agarose gel electrophoresis, and was inserted into the plasmid p35SRDX having the promoter CaMV 35S and the transcriptional regulatory domain SRDX prepared in [Example 1] (1-1) (a) and (*b*) by a conventional process. The resulting plasmids were sequenced by a conventional method to screen a specific plasmid that coincided with the gene At2g38090 in a reading frame of SRDX from the plasmids containing the gene At2g38090 introduced in the forward direction.

The resultant plasmid for transformation carries the chimeric gene ProCaMV 35S:At2g38090SRDX where the promoter ProCaMV 35S, the gene At2g38090, and the transcriptional regulatory domain SRDX are operably linked. This plasmid is abbreviated as "Construct D" as appropriate, and the chimeric gene ProCaMV 35S:At2g38090SRDX carried on Construct D is abbreviated as "Chimeric gene D" as appropriate. The schematic structure of Chimeric gene D is shown in FIG. 2A.

(4-2) Development of Transformed Plant D by Transformation with Construct D

The *Arabidopsis thaliana* plants were transformed with Construct D as in [Example 1] (1-2), and plants successfully transformed were screened with a hygromycin medium. The resultant plant transformed with Construct D is abbreviated as "Transformed plant D" as appropriate.

[Example 5] Production of Construct E (ProCaMV 35S:At5g58900SRDX) for Transformation and *Arabidopsis thaliana* Plant Transformation (5-1) Production of Construct E The cDNA of the gene At5g58900 in *Arabidopsis thaliana* as a template was subjected to the PCR with a 5' end upper primer having the base sequence of SEQ ID NO: 57 described below and a 3' end lower primer having the base sequence of SEQ ID NO: 58 described below as in [Example 1] (1-1) (b) to amplify a partial sequence where the stop codon was removed from the gene At5g58900.

(SEQ ID NO: 57)
5'-gATGGAGGTTATGAGACCGTCGACGTCACA-3'

(SEQ ID NO: 58)
5'-TAGTTGAAACATTGTGTTTTGGGCGTCATA-3'

The resultant amplification product without the stop codon of the gene At5g58900 was cleaved with SmaI, was recovered by agarose gel electrophoresis, and was inserted into the plasmid p35SRDX having the promoter CaMV 35S and the transcriptional regulatory domain SRDX prepared in [Example 1] (1-1) (a) and (b) by a conventional process. The resulting plasmids were sequenced by a conventional method to screen a specific plasmid that coincided with the gene At5g58900 in a reading frame of SRDX from the plasmids containing the gene At5g58900 introduced in the forward direction.

The resultant plasmid for transformation carries the chimeric gene ProCaMV 35S:At5g58900SRDX where the promoter ProCaMV 35S, the gene At5g58900, and the transcriptional regulatory domain SRDX are operably linked. This plasmid is abbreviated as "Construct E" as appropriate, and the chimeric gene ProCaMV 35S:At5g58900SRDX carried on Construct E is abbreviated as "Chimeric gene E" as appropriate. The schematic structure of Chimeric gene E is shown in FIG. 2A.

(5-2) Development of Transformed Plant E by Transformation with Construct E

The *Arabidopsis thaliana* plants were transformed with Construct E as in [Example 1] (1-2), and plants successfully transformed were screened with a hygromycin medium. The resultant plant transformed with Construct E is abbreviated as "Transformed plant E" as appropriate.

[Example 6] Production of Construct F (ProCaMV 35S:At3g16350SRDX) for Transformation and *Arabidopsis thaliana* Plant Transformation (6-1) Production of Construct F The cDNA of the gene At3g16350 in *Arabidopsis thaliana* as a template was subjected to the PCR with a 5' end upper primer having the base sequence of SEQ ID NO: 59 described below and a 3' end lower primer having the base sequence of SEQ ID NO: 60 described below as in [Example 1] (1-1) (b) to amplify a partial sequence where the stop codon was removed from the gene At3g16350.

(SEQ ID NO: 59)
5'-gATGACTCGTCGGTGTTCGCATTGTAGCAA-3'

(SEQ ID NO: 60)
5'-GATAGCCTGAATCGCGCTGTTGCCTTTACT-3'

The resultant amplification product without the stop codon of the gene At3g16350 was cleaved with SmaI, was recovered by agarose gel electrophoresis, and was inserted into the plasmid p35SRDX having the promoter CaMV 35S and the transcriptional regulatory domain SRDX prepared in [Example 1] (1-1) (a) and (b) by a conventional process. The resulting plasmids were sequenced by a conventional method to screen a specific plasmid that coincided with the gene At3g16350 in a reading frame of SRDX from the plasmids containing the gene At3g16350 introduced in the forward direction.

The resultant plasmid for transformation carries the chimeric gene ProCaMV 35S:At3g16350SRDX where the promoter ProCaMV 35S, the gene At3g16350, and the transcriptional regulatory domain SRDX are operably linked. This plasmid is abbreviated as "Construct F" as appropriate, and the chimeric gene ProCaMV 35S:At3g16350SRDX carried on Construct F is abbreviated as "Chimeric gene F" as appropriate. The schematic structure of Chimeric gene F is shown in FIG. 2A.

(6-2) Development of Transformed Plant E by Transformation with Construct F

The *Arabidopsis thaliana* plants were transformed with Construct F as in [Example 1] (1-2), and plants successfully transformed were screened with a hygromycin medium. The resultant plant transformed with Construct F is abbreviated as "Transformed plant F" as appropriate.

[Example 7] Production of Construct G (ProAt5g01200:At5g01200SRDX) for transformation and *Arabidopsis thaliana* plant transformation (7-1) Production of Construct G (a) Construction of Plasmid p35SRDX The plasmid p35SRDX into which the promoter ProCaMV 35S and the transcriptional regulatory domain SRDX were introduced was constructed as in [Example 1] (1-1) (a) and (b).

(b) Construction of plasmid ProAt5g01200-SRDX-NOS

In the plasmid p35SRDX, a mutation was introduced into the HindIII site at the 5' side of the attL1 sequence by a conventional process. This plasmid was cleaved with HindIII and SmaI, and a DNA fragment containing a multicloning site was inserted into the plasmid to form pSRDX-NOS.

The genome in *Arabidopsis thaliana* as a template was subjected to the PCR with a 5' end upper primer having the base sequence of SEQ ID NO: 61 described below and a 3' end lower primer having the base sequence of SEQ ID NO: 62 described below to amplify a promoter region having about 2.3 kbp located in the 5' upstream region of the coding region of the gene At5g01200.

(SEQ ID NO: 61)
5'-GGGAAGCTTCGGACTTCTGATTGATCCATAGTTTGTCC-3'

(SEQ ID NO: 62)
5'-GGGGGATCCAGCTCCTCCTCTGTTTTTGGTGAAAACTTTC-3'

The PCR was repeated 30 cycles, each cycle including a denaturing reaction at 94° C. for one minute, an annealing reaction at 50° C. for one minute, and an extending reaction at 72° C. for three minutes.

The resultant amplification product of the promoter region of the gene At5g01200 (hereinafter, referred to as "ProAt5g01200" as appropriate) was cleaved with HindIII and BamHI by a conventional process and recovered by agarose gel electrophoresis. Similarly, the plasmid pSRDX-NOS described above was cleaved with HindIII and BamHI by a conventional process and recovered by agarose gel electrophoresis. The cleaved fragment of the promoter ProAt5g01200 described above was inserted into the cleaved fragment of the plasmid pSRDX-NOS by a conventional process, and the product was sequenced to screen a specific plasmid containing the 5' upstream region of the gene At5g01200 introduced in the forward direction and having no PCR error. The resultant plasmid is referred to as "ProAt5g01200-SRDX-NOS vector".

(c) Production of ProAt5g01200:At5g01200SRDX by Insertion of At5g01200 into Plasmid The cDNA of the gene At5g01200 in *Arabidopsis thaliana* as a template was subjected to the PCR with a 5' end upper primer having the base sequence of SEQ ID NO: 53 and a 3' end lower primer having the base sequence of SEQ ID NO: 54 as in [Example 3] (1-1) to amplify a partial sequence where the stop codon was removed from the gene At5g01200.

The resultant amplification product without the stop codon of the gene At5g01200 was cleaved with SmaI, was recovered by agarose gel electrophoresis, and was inserted into the plasmid ProAt5g01200-SRDX-NOS having the promoter ProAt5g01200 prepared in (b) described above and the transcriptional regulatory domain SRDX by a conventional process. The resulting plasmids were sequenced to screen a specific plasmid that coincided with the gene At5g01200 in a reading frame of SRDX from the plasmids containing the gene At5g01200 introduced in the forward direction.

The resultant plasmid for transformation carries the chimeric gene ProAt5g01200:At5g01200SRDX where the promoter ProAt5g01200, the gene At5g01200, and the transcriptional regulatory domain SRDX are operably linked. This plasmid for transformation is abbreviated as "Construct G" as appropriate, and the chimeric gene ProCaMV 35S:At5g01200SRDX carried on Construct G is abbreviated as "Construct G" as appropriate. The schematic structure of Chimeric gene F is shown in FIG. 2A.

(7-2) Development of Transformed Plant G by Transformation with Construct G

The *Arabidopsis thaliana* plants were transformed with Construct G as in [Example 1] (1-2), and plants successfully transformed were screened with a hygromycin medium. The resultant plant transformed with Construct G is abbreviated as "Transformed plant G" as appropriate.

[Evaluation 1] Confirmation of Traits of Transformed Plants

The stamens were removed (emasculated) from the buds of Transformed plants A to G, and the traits of unfertilized pods and ovules were observed. Similarly, the traits of unfertilized pod and ovule in a wild-type *Arabidopsis thaliana* plant were observed as a control. FIG. 3 shows the optical micrographs of Transformed plants A to E, and FIG. 4 shows the optical micrographs of Transformed plant G. With FIG. 3, the micrographs illustrate (a) appearances of buds, (b) appearances of pods, (c) the interiors of pods, and (d) ovules of the wild-type plant and Transformed plants A to E. With FIG. 4, the micrographs illustrate (a) appearance of pods (shown in comparison to the wild-type plant), (b) the interior of pod, and (c1) and (c2) ovules of Transformed plant G. The micrographs in FIGS. 3 and 4 evidentially demonstrate the elongation of pods and the swelling of ovules under the unfertilized conditions in all Transformed plants A to G as compared with the wild-type plant. These results prove that Constructs A to G having Chimeric genes A to G induce spontaneous swelling of ovules (or swelling of ovules under unfertilization) in *Arabidopsis thaliana*.

Figure 5A:
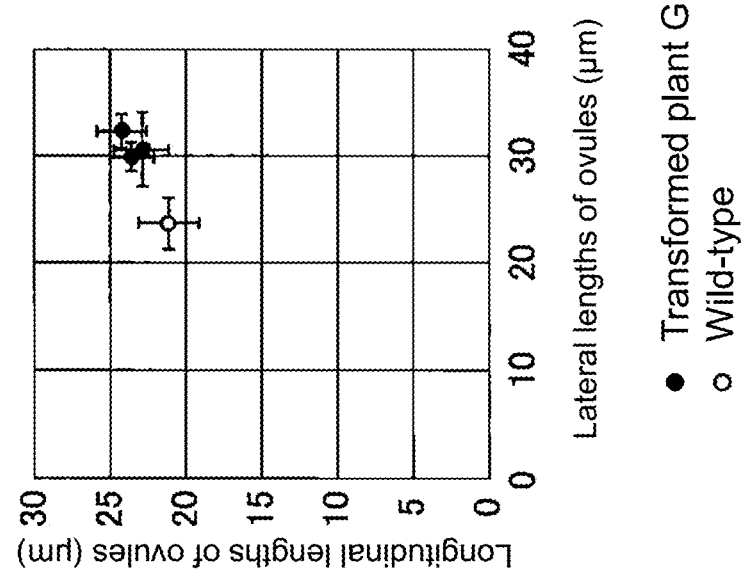
FIGS. 5A to 5C are graphs illustrating the longitudinal and lateral lengths of ovules in Transformed plants A, C, and G, respectively.
Figure 5B:
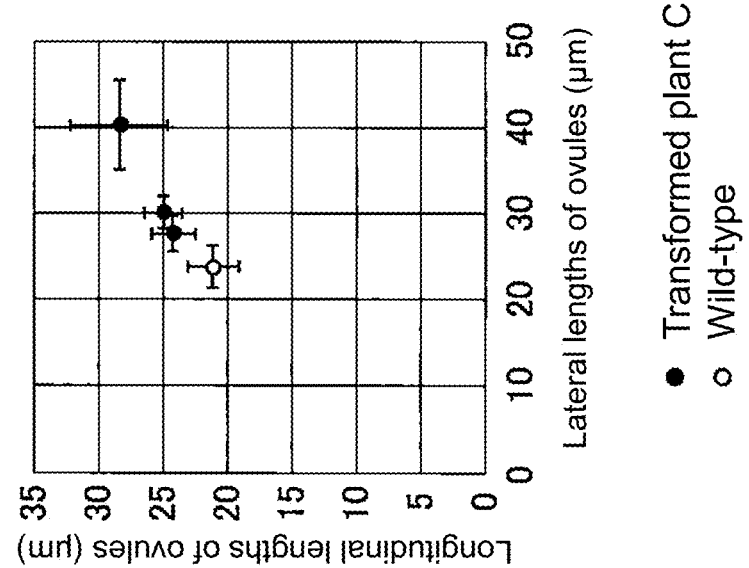
Figure 5C:
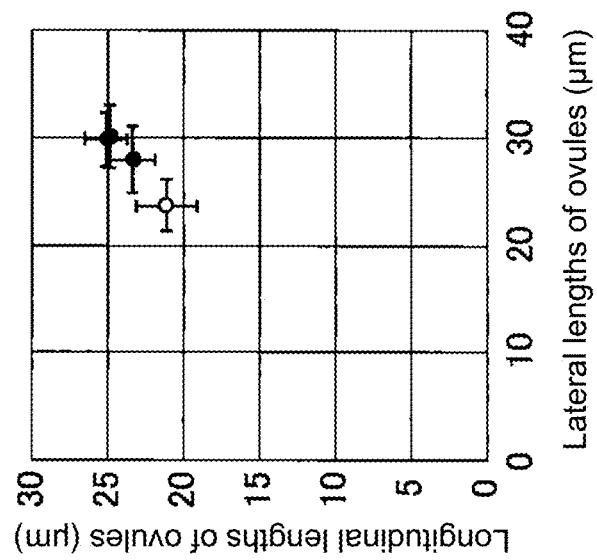
Figure 6:
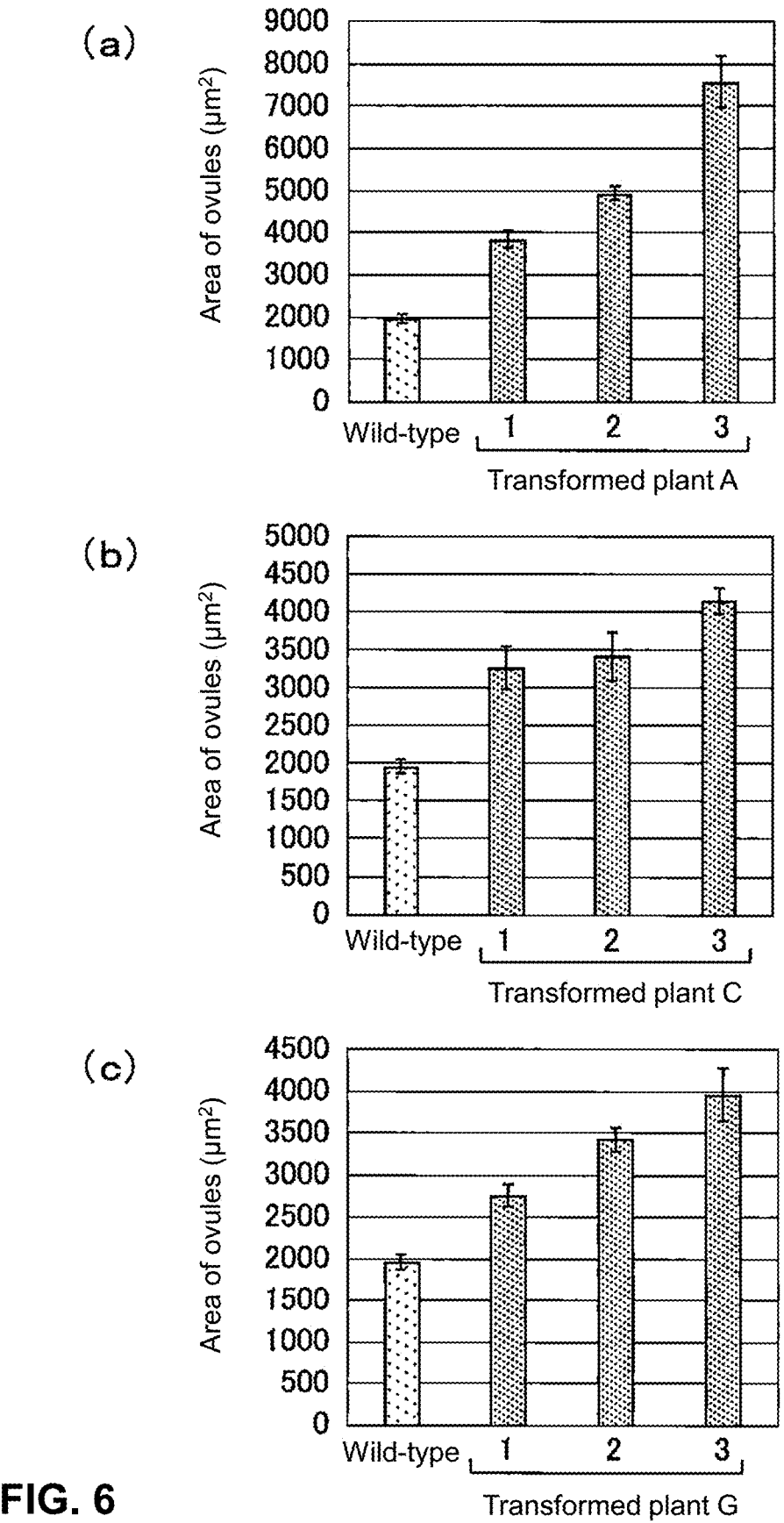
FIG. 6 are graphs illustrating the areas of endosperm portions in Transformed plants A, C and G.

The longitudinal and lateral lengths of the ovules in Transformed plants A, C, and G were then measured to calculate the areas of the endosperm portions. FIGS. 5A to 5C are graphs illustrating the longitudinal and lateral lengths of the ovules in Transformed plants A, C, and G, respectively, and FIG. 6 are graphs illustrating the areas of the endosperm portions in Transformed plants A, C, and G, respectively. The development of endosperm was observed in all Transformed plants A, C, and G. These results prove that Constructs A, C, and G having Chimeric genes A, C, and G induce spontaneous endosperm development (or endosperm development under unfertilization) in *Arabidopsis thaliana*.

Figure 7:
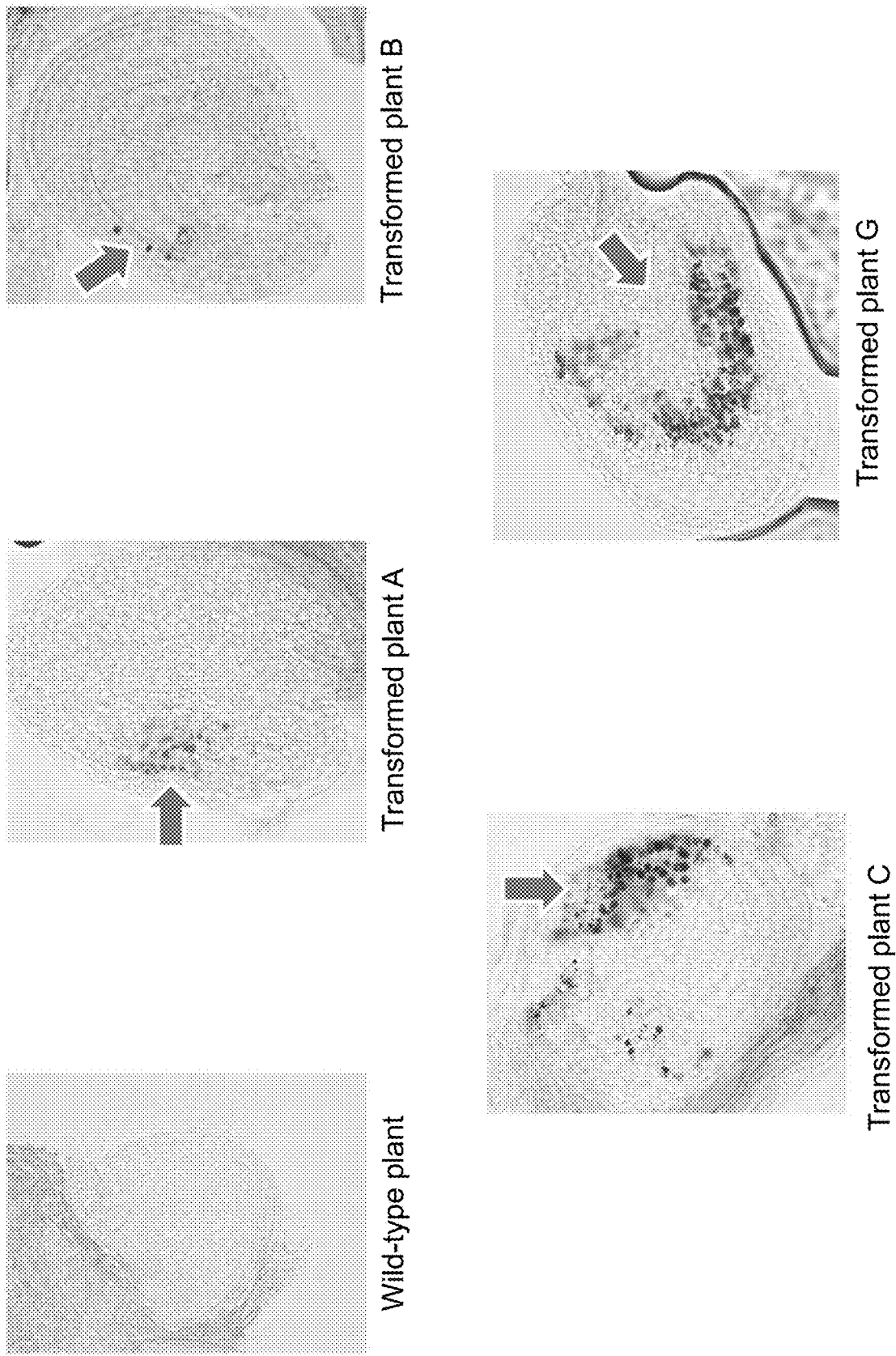
FIG. 7 shows optical micrographs of ovules stained with vanillin in a wild-type plant and Transformed plants A to C and G.

[Evaluation 2] Analysis of Seed Coat Development in Ovules of Transformed Plants The unfertilized pods of Transformed plants A to C and G were dissected, and the extracted ovules were stained with a vanillin staining suspension (0.2 g of vanillin suspended in 10 ml of 6N HCl solution), and the stained pods were observed with an optical microscope. Similarly, the ovule from a wild-type *Arabidopsis thaliana* plant as a control was stained with the vanillin suspension and observed with an optical microscope. FIG. 7 shows the optical micrographs of the ovules of the wild-type plant and Transformed plants A to C and G. All the unfertilized ovules of Transformed plants A to C and G exhibited red coloration with the vanillin staining suspension.

The vanillin staining suspension stains proanthocyanidin in seed coats to exhibit a red color. Accumulation of proanthocyanidin in the seed coats is known to be induced by endosperm development, and the vanillin staining is thus regarded as a marker for endosperm development. In other words, the fact that the vanillin staining was observed in the unfertilized ovules of Transformed plants A to C and F indicates that Transformed plants A to C and G can develop the endosperms without fertilization. These results prove that Constructs A to C and G having Chimeric genes A to C and G, respectively, induce spontaneous endosperm development (or endosperm development under unfertilization) in *Arabidopsis thaliana*.

[Evaluation 3] Experiments of Nurturing Embryos by Endosperms that Spontaneously Develop in Transformed Plants The stamens were removed (emasculated) from the buds in Transformed plants A and G, and the pollen with kokoperi mutants (having a red fluorescent marker) was pollinated to unfertilized pistils.

The principle of the experiment using the kokopelli mutants will now be explained with reference to FIGS. 8A to 8C. As shown in FIG. 8A, it is known that the general pollen contains two sperm cells and these two sperm cells fuse with an egg cell and a central cell, respectively, during pollination to develop a fertilized egg and an endosperm (double fertilization). In contrast, as shown in FIGS. 8B and 8C, the pollen with the kokopelli mutants contains only one sperm cell that can be fertilized, and thereby either one of the egg cell and the central cell is fertilized in the ovule pollinated with the kokopelli mutant pollen (single fertilization).

In the present Examples, the kokopelli pollen was crossed with the pistils of Transformed plants A and G, and the development of embryos in the ovules in which only the egg cells was fertilized was observed to determine whether the endosperm developed without fertilization in Transformed plants A and G can nurture the fertilized embryos.

FIGS. 9A-9C show optical microscope photographs (top) and red fluorescent photographs (bottom) of ovules in the plants prepared by crossing the pistils of the wild-type plant and Transformed plants A and G with the kokopelli pollen. In the case of a pistil pollinated with the kokopelli pollen (FIG. 9A) in the wild-type plant, the development of embryo stopped in a globular form and the ovule was crushed. In the case of a pistil pollinated with the kokopelli pollen in Transformed plant A (FIG. 9B) and a pistil pollinated with the kokopelli pollen in Transformed plant G (FIG. 9C), the ovules still had enough room even if the embryo development progressed until the initial heart-shaped embryo. These results prove that the endosperm developed without fertilization in Transformed plants A and G can nurture the embryos.

[Example 8] Production of Construct H (ProZmUBQ1:Os05g0543600SRDX) for Transformation and *Oryza sativa* Plant Transformation (8-1) Production of Construct H
(a) Production of Plasmid pZmUBQ1_SRDX_HSP The vector pUBQ1SXG described in Yoshida et al., Front Plant Sci. (2013) 4, 383, was cleaved with restriction enzymes EcoRI and SacI, and the DNA fragment containing a Heat Shock Protein terminator produced by cleavage of the plasmid pRI201-AN (Takara Bio Inc., Japan) with the restriction enzymes EcoRI and SacI was inserted into the cleaved vector. This product is referred as "plasmid pZmUBQ1_SRDX_HSP". This plasmid contains a *Zea mays* UBQ1 promoter, a region encoding the transcriptional regulatory domain SRDX, and a terminator region of the gene HSP18.2 in *Arabidopsis thaliana*, and has attL1 and attL2 GATEWAY recombinant sites at two ends thereof.

(b) Production of Construct H

The cDNA of the gene Os05g0543600 in *Oryza sativa* as a template was subjected to the PCR with a 5' end upper primer having the base sequence of SEQ ID NO: 63 and a 3' end lower primer having the base sequence of SEQ ID NO: 64 as in [Example 1] (1-1) (b) to amplify a partial sequence where the stop codon was removed from the gene Os05g0543600.

(SEQ ID NO: 63)
5'-gATGGGACGGCTGTCGTCGTG-3'

(SEQ ID NO: 64)
5'-GAAGTATTCCAAGTTGAAGTCGAATTGAGC-3'

The resultant amplification product without the stop codon of the gene Os05g0543600 was cleaved with SmaI, was recovered by agarose gel electrophoresis, and was inserted into the plasmid pZmUBQ1_SRDX_HSP by a conventional process. The resulting plasmids were sequenced by a conventional method to screen a specific plasmid that coincided with the gene Os05g0543600 in a reading frame of SRDX from the plasmids containing the gene Os05g0543600 introduced in the forward direction.

The resultant plasmid was subjected to the GATEWAY LR reaction with a pBCKH vector described in Mitsuda et al., Plant Biotech. J., (2006) 4, 325-332 to yield a plasmid for transformation based on the vector pBCKH.

The resultant plasmid for transformation carries the chimeric gene ProZmUBQ1:Os05g0543600SRDX where the promoter ProZmUBQ1, the gene Os05g0543600, and the transcriptional regulatory domain SRDX are operably linked. This plasmid is abbreviated as "Construct H" as appropriate, and the chimeric gene ProZmUBQ1:Os05g0543600SRDX carried on Construct H is abbreviated as "Chimeric gene H" as appropriate. The schematic structure of Chimeric gene H is shown in FIG. 2B.

(8-2) Development of Transformed Plant H

The Oryza sativa calluses were transformed with Construct H by the method described in "A protocol for Agrobacterium-mediated transformation in rice" (Nishimura et al. 2006, Nature Protocols, 1:2796). Construct H was introduced into a soil bacterium, i.e., Agrobacterium tumefaciens strain EHA105 (Hood et al., Transgenic Research (1993) 2: 208-218.) by electroporation.

The bacterial cells were then collected and suspended in an infiltration medium (30 mL, AAM containing acetosyringone). The embryogenic calluses induced from Oryza sativa seeds for three to four weeks were immersed in this solution for one and half minutes and co-cultivated for 48 to 60 hours on a co-culture medium (2N6-AS medium). The calluses were washed and then cultivated on a selective medium (N6D-S medium) containing hygromycin for three to four weeks. Calluses successfully transformed with Construct H acquired hygromycin resistance. The transformed calluses that grew in the hygromycin medium were selected, and were cultivated on a re-differentiation medium containing hygromycin (MS-NK medium) for three to four weeks and then on a plant growing medium containing hygromycin (MS-HF medium) for three to four weeks to reproduce transformed plants. The resultant transformed plants were replanted in a soil and grown. The plant transformed with Construct H in such a procedure is abbreviated as "Transformed plant H" as appropriate.

[Example 9] Production of Construct I (ProZmUBQ1:Os01g0142500SRDX) for Transformation and Oryza sativa Plant Transformation (9-1) Production of Construct I The cDNA of the gene Os01g0142500 in Oryza sativa as a template was subjected to the PCR with a 5' end upper primer having the base sequence of SEQ ID NO: 65 and a 3' end lower primer having the base sequence of SEQ ID NO: 66 as in [Example 1] (1-1) (b) to amplify a partial sequence where the stop codon was removed from the gene Os01g0142500.

(SEQ ID NO: 65)
5'-gATGATGATGAGGGATGTGTGCATGGAGGT-3'

(SEQ ID NO: 66)
5'-AAACAATATGCTTCGGCTCGCGGCCAACTG-3'

The resultant amplification product without the stop codon of the gene Os01g0142500 was cleaved with SmaI, was recovered by agarose gel electrophoresis, and was inserted into the plasmid pZmUBQ1_SRDX_HSP by a conventional process. The resulting plasmids were sequenced by a conventional method to screen a specific plasmid that coincided with the gene Os01g0142500 in a reading frame of SRDX from the plasmids containing the gene Os01g0142500 introduced in the forward direction. The resultant plasmid was then subjected to the GATEWAY LR reaction with pBCKH to yield a plasmid for transformation.

The resultant plasmid for transformation carries the chimeric gene ProZmUBQ1:Os01g0142500SRDX where the promoter ProZmUBQ1, the gene Os01g0142500, and the transcriptional regulatory domain SRDX are operably linked. This plasmid is abbreviated as "Construct I" as appropriate, and the chimeric gene ProZmUBQ1:Os01g0142500SRDX carried on Construct I is abbreviated as "Chimeric gene I" as appropriate. The schematic structure of Chimeric gene I is shown in FIG. 2B.

(9-2) Development of Transformed Plant I by Transformation with Construct I

The Oryza sativa plants were transformed with Construct I as in [Example 8] (8-2), and plants successfully transformed were screened with a hygromycin medium. The resultant plant transformed with Construct I is abbreviated as "Transformed plant I" as appropriate.

[Example 10] Production of Construct J (ProOsFST:Os01g0853700SRDX) for Transformation and Oryza sativa Plant Transformation (10-1) Production of Construct J
(a) Production of plasmid pOsFSTp-SRDX-HSP_Entry The vector pSRDX-NOS_entry described in Mitsuda et al., Plant Cell (2007) 19, 270. was cleaved with restriction enzymes EcoRI and SacI, and the DNA fragment containing a Heat Shock Protein terminator produced by cleavage of the plasmid pRI201-AN (Takara Bio Inc., Japan) with the restriction enzymes EcoRI and SacI was inserted into the cleaved vector. This product is referred to as "plasmid pSRDX-HSP_entry". The Oryza sativa genome as a template was subjected to the PCR with a 5' end upper primer having the base sequence of SEQ ID NO: 67 described below and a 3' end lower primer having the base sequence of SEQ ID NO: 68 described below to amplify a promotor region of FST gene in Oryza sativa.

(SEQ ID NO: 67)
5'-GGCCGGCGCGCCTTATATATGGTCATTATATATTTGCTA-3'

(SEQ ID NO: 68)
5'-AAATTTGGATCCGCCTGCTATACCTTCCTGATCGAGTTT-3'

The PCR was repeated 30 cycles, each cycle including a denaturing reaction at 98° C. for ten seconds subsequent to a denaturing reaction at 98° C. for two minutes, an annealing reaction at 55° C. for twenty seconds, and an extending reaction at 72° C. for three minutes.

The resultant amplification product of the promoter region of the FST gene was cleaved with AscI and BamHI, was recovered by agarose gel electrophoresis, and was inserted into the plasmid pSRDX-HSP_entry described above by a conventional process. The resulting plasmids were sequenced by a conventional method to screen a specific plasmid having a base sequence of the FST promoter region coinciding with the genomic information. This plasmid is referred to as "plasmid pFSTp-SRDX-HSP_entry". This plasmid contains the FST promoter in *Oryza sativa*, the region encoding the transcriptional regulatory domain SRDX, and the terminator region of the gene HSP18.2 in *Arabidopsis thaliana*, and has attL1 and attL2 GATEWAY recombinant sites at two ends thereof.

(b) Production of Construct J

The cDNA of the gene Os01g0853700 in *Oryza sativa* as a template was subjected to the PCR with a 5' end upper primer having the base sequence of SEQ ID NO: 69 and a 3' end lower primer having the base sequence of SEQ ID NO: 70 as in [Example 1] (1-1) (a) to amplify a partial sequence where the stop codon was removed from the gene Os01g0853700.

(SEQ ID NO: 69)
5'-GATGATGGCAGAGGCGCTTCGGGAGGTGCT-3'

(SEQ ID NO: 70)
5'-CAAGTGTCCGCATTGCATCTGCAGGAG-3'

The resultant amplification product without the stop codon of the gene Os01g0853700 was cleaved with SmaI, was recovered by agarose gel electrophoresis, and was inserted into the plasmid pFSTp-SRDX-HSP_entry described above by a conventional process. The resulting plasmids were sequenced by a conventional method to screen a specific plasmid that coincided with the gene Os01g0853700 in a reading frame of SRDX from the plasmids containing the gene Os01g0853700 introduced in the forward direction.

The resultant plasmid was subjected to the GATEWAY LR reaction with a pBCKH vector described in Mitsuda et al., Plant Biotech. J., (2006) 4, 325-332 to yield a plasmid for transformation based on the pBCKH vector.

The resultant plasmid for transformation carries the chimeric gene ProOsFST:Os01g0853700SRDX where the promoter ProOsFST, the gene Os01g0853700, and the transcriptional regulatory domain SRDX are operably linked. This plasmid is abbreviated as "Construct J" as appropriate, and the chimeric gene ProOsFST:Os01g0853700SRDX carried on Construct J is abbreviated as "Chimeric gene J" as appropriate. The schematic structure of Chimeric gene J is shown in FIG. 2B.

(10-2) Development of Transformed Plant J by Transformation with Construct J

The *Oryza sativa* plants were transformed with Construct J as in [Example 8] (8-2), and plants successfully transformed were screened with a hygromycin medium. The resultant plant transformed with Construct J is abbreviated as "Transformed plant J" as appropriate.

[Example 11] Production of Construct K (ProOsFST:Os04g0569100SRDX) for Transformation and *Oryza sativa* Plant Transformation (11-1) Production of Construct K The cDNA of the gene Os04g0569100SRDX in *Oryza sativa* as a template was subjected to the PCR with a 5' end upper primer having the base sequence of SEQ ID NO: 71 and a 3' end lower primer having the base sequence of SEQ ID NO: 72 as in [Example 1] (1-1) (b) to amplify a partial sequence where the stop codon was removed from the gene Os01g0142500.

(SEQ ID NO: 71)
5'-GATGCAGTTCCCGTTCTCCGGCGCTGGCCC-3'

(SEQ ID NO: 72)
5'-CACGTCGCAATGCAGCGCCGTCTTGATCTT-3'

The resultant amplification product without the stop codon of the gene Os04g0569100 was cleaved with SmaI, was recovered by agarose gel electrophoresis, and was inserted into the plasmid pFSTp-SRDX-HSP_entry described above by a conventional process. The resulting plasmids were sequenced by a conventional method to screen a specific plasmid that coincided with the gene Os04g0569100 in a reading frame of SRDX from the plasmids containing the gene Os04g0569100 introduced in the forward direction. The resultant plasmid was subjected to the GATEWAY LR reaction with the pBCKH to yield a plasmid for transformation.

The resultant plasmid for transformation carries the chimeric gene ProOsFST:Os04g0569100SRDX where the promoter ProOsFST, the gene Os04g0569100, and the transcriptional regulatory domain SRDX are operably linked. This plasmid is abbreviated as "Construct K" as appropriate, and the chimeric gene ProOsFST:Os04g0569100SRDX carried on Construct K is abbreviated as "Chimeric gene K" as appropriate. The schematic structure of Chimeric gene K is shown in FIG. 2B.

(11-2) Development of Transformed Plant K by Transformation with Construct K

The *Oryza sativa* plants were transformed with Construct K as in [Example 8] (8-2), and plants successfully transformed were screened with a hygromycin medium. The resultant plant transformed with Construct K is abbreviated as "Transformed plant K" as appropriate.

[Evaluation 4] Confirmation of Traits of Transformed Plants

Figure 10A:
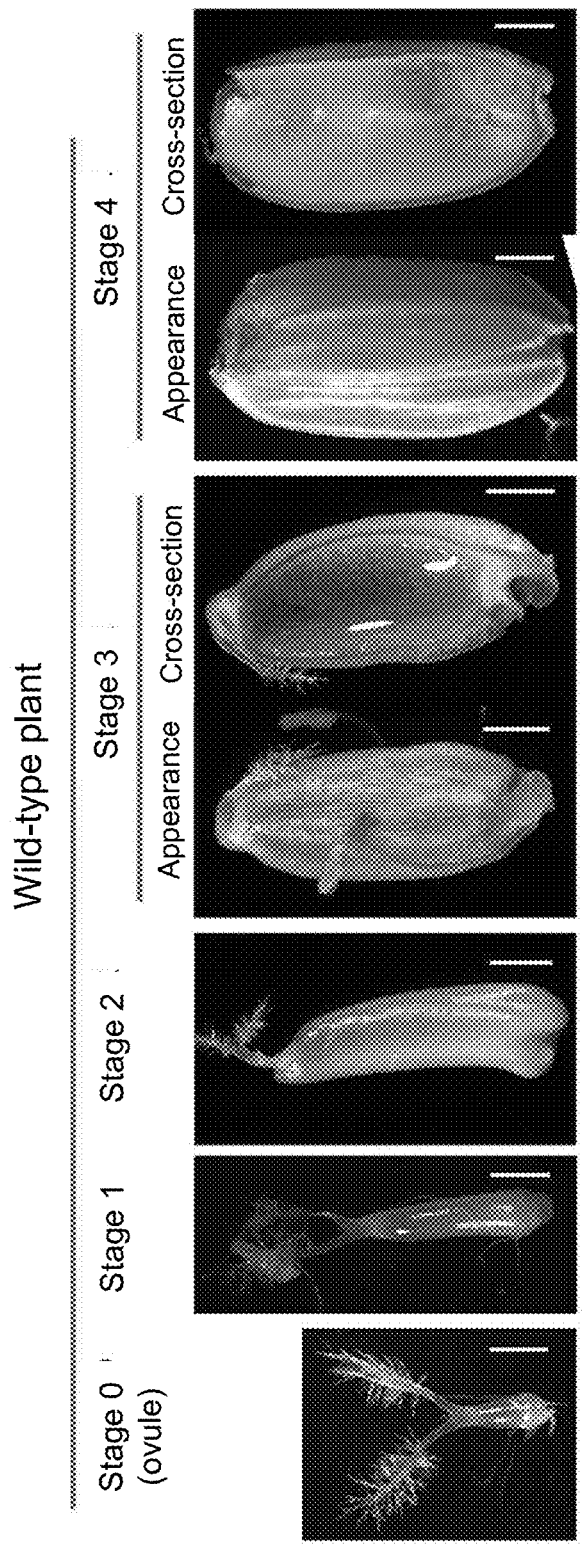
FIG. 10A shows ovule developmental stages 0 to 4 of the wild-type *Oryza sativa* plant.
Figure 10B:
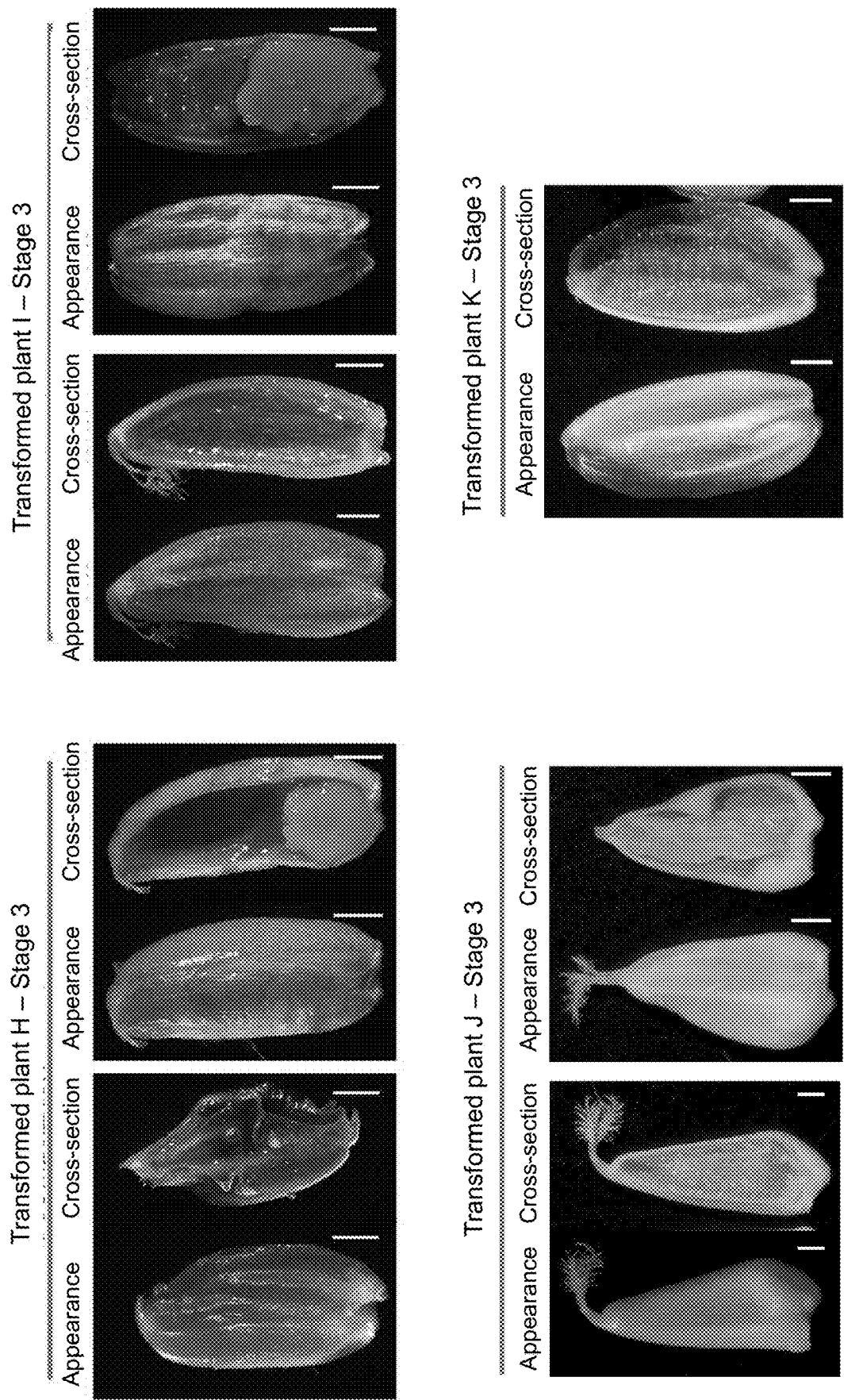
FIG. 10B shows representative photographs of the ovules (at developmental stage 3) that spontaneously swelled even after emasculation in Transformed plants H, I, J, and K.

The inflorescences of Transformed plants H, I, J, and K during blooming were soaked in warm water (42° C.) for seven minutes, and the stamens were then removed (emasculated) from the flowers that bloomed on the same day. The flowers that had already finished blooming and the buds before blooming were cut off, and the development of unfertilized ovules was observed in the emasculated flowers. Similarly, the inflorescence of a wild-type *Oryza sativa* plant was emasculated as a control, and the development of unfertilized ovules was observed in the same manner. The development of ovules was observed also in the inflorescences of Transformed plants H, I, J, and K and the wild-type plant that were not emasculated. The development of ovules was classified into Stages 0 to 4. FIG. 10A and FIG. 10B show representative photographs of the appearances of ovules at respective Stages in the wild-type *Oryza sativa* plant and the appearances of ovules spontaneously swelled even after emasculation at Stage 3 in Transformed plants H, I, J and K, respectively. The ovule has the same size as that before blooming at Stage 0, whereas the swelling of endosperm was observed at Stages 1 to 4. The photographs at Stages 3 and 4 in FIGS. 10A and 10B show the cross-sections of the ovules on the right side. The endosperm at Stage 4 exhibits a complete solid state, whereas the endosperm at Stage 3 exhibits a partial or whole liquid state.

Figure 11A:
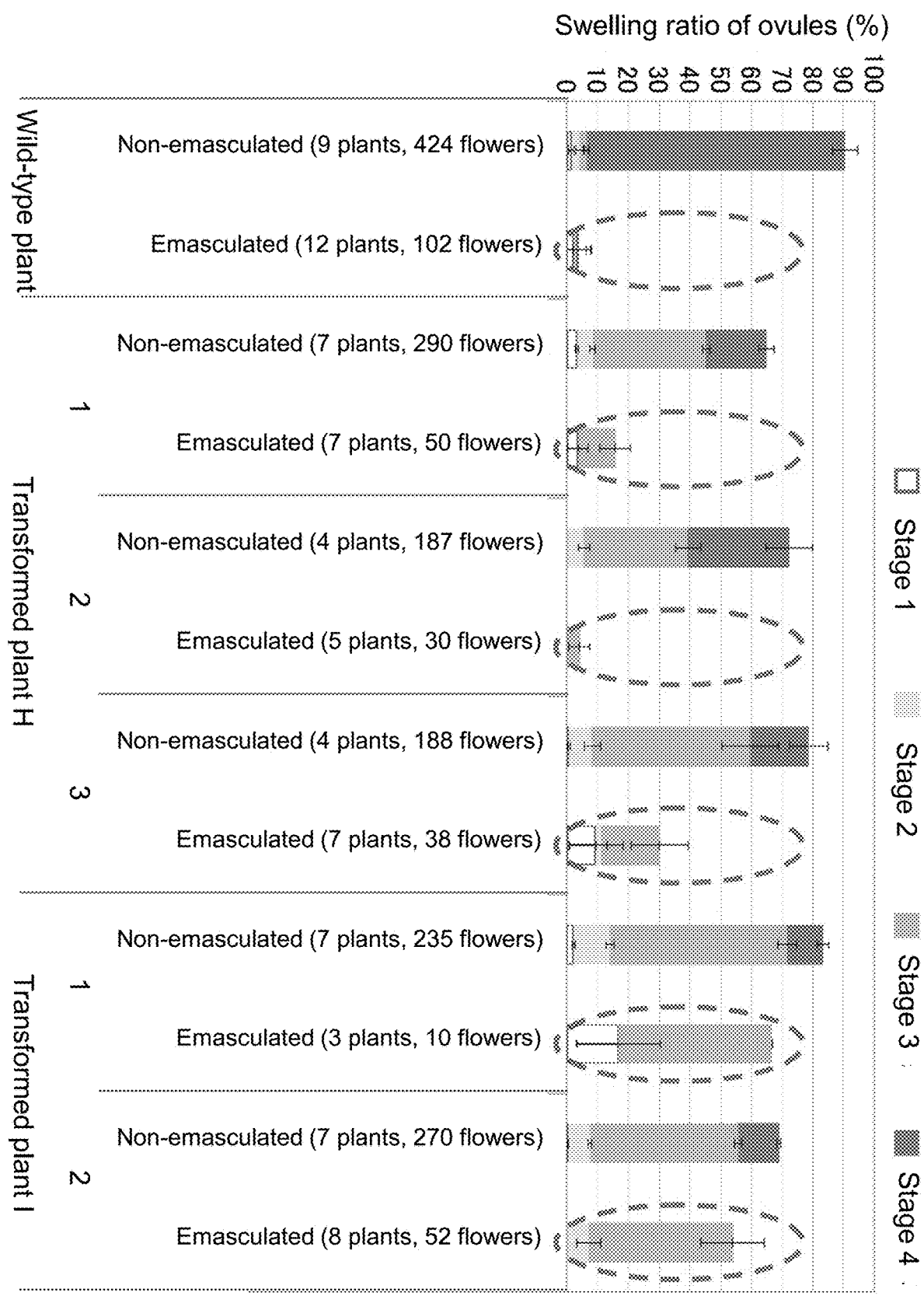
FIG. 11A shows a graph illustrating the swelling rate of emasculated ovules and non-emasculated ovules in progenies prepared by self-pollination of Transformed plants H and I and the wild-type plant.
Figure 11B:
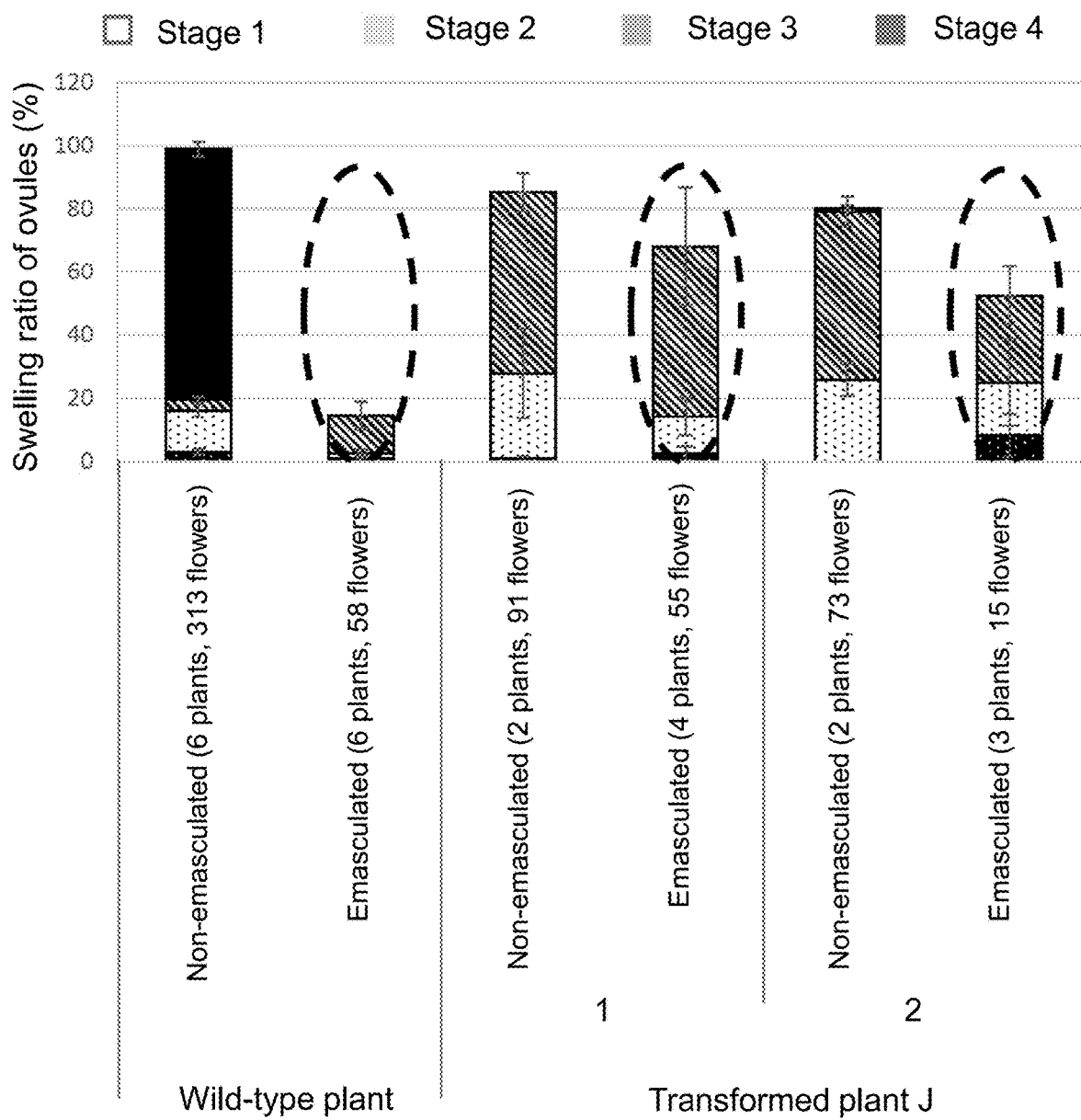
FIG. 11B shows a graph illustrating the swelling rate of emasculated ovules and non-emasculated ovules in progenies prepared by self-pollination of Transformed plant J and the wild-type plant.
Figure 12:
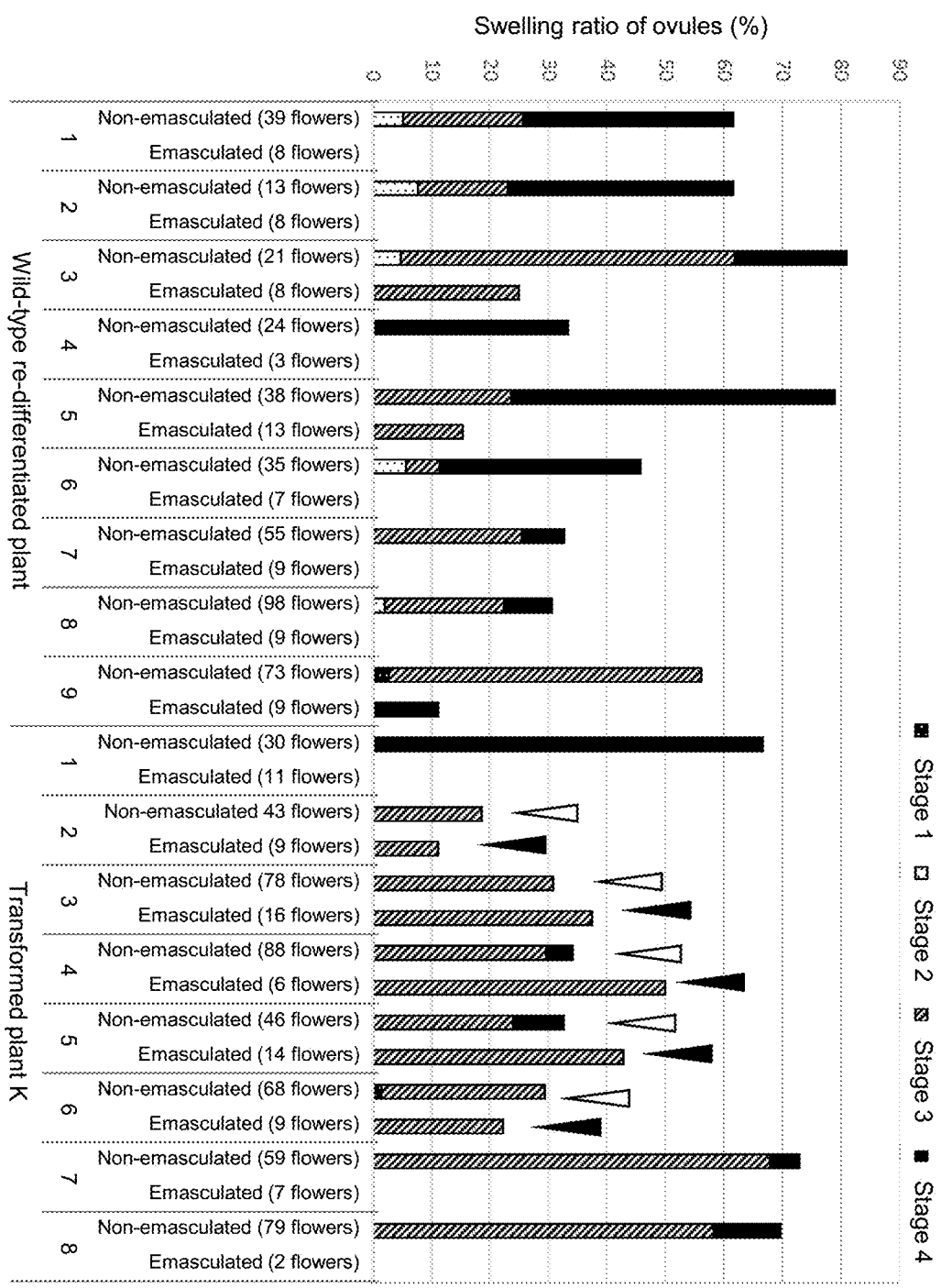
FIG. 12 shows a graph illustrating the swelling rate of emasculated ovules and non-emasculated ovules in Transformed plant K and the wild-type plant.

FIGS. 11A and 11B show graphs illustrating the swelling rate of emasculated ovules and non-emasculated ovules in progenies prepared by self-pollination of Transformed plants H, I, and J and in the wild-type plants. FIG. 12 shows a graph illustrating the swelling rate of emasculated ovules and non-emasculated ovules in Transformed plant K and a wild-type re-differentiated plant. In Transformed plants H, I, J, and K, the swelling of ovules was observed even when emasculated (under unfertilized conditions). These results prove that Constructs H, I, J, and K having Chimeric genes H, I, J, and K, respectively, induce the spontaneous swelling of ovules (the swelling of ovules under unfertilization) in *Oryza sativa*.

Figure 13:
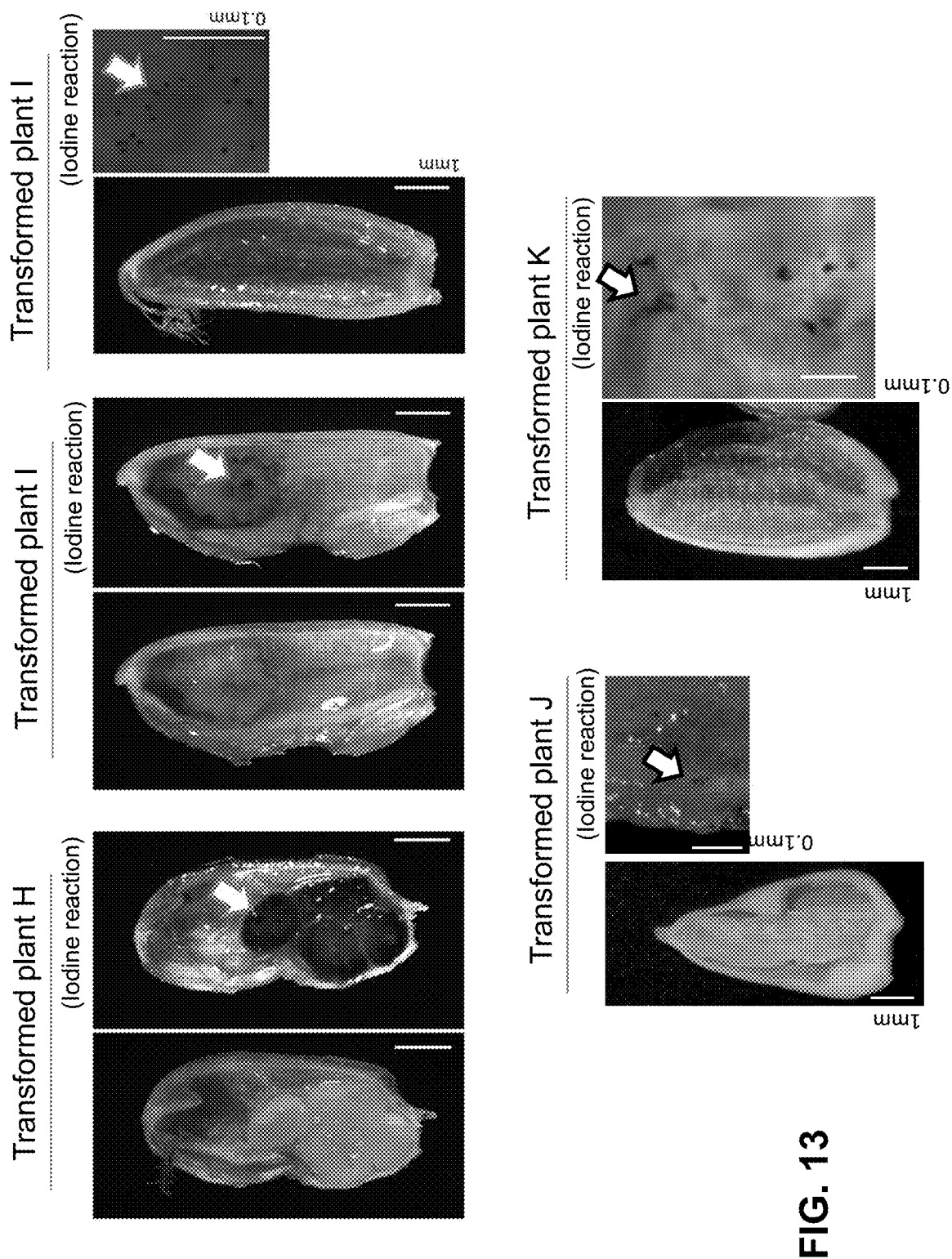
FIG. 13 shows stereoscopic micrographs of the ingredients of ovules that spontaneously swelled even after emasculation of Transformed plants H, I, J and K before and after staining with an iodine solution.

The ingredients of the ovules that spontaneously swelled in Transformed plants H, I, J, and K were also stained with an iodine solution (0.1 g of potassium iodide and 0.5 g of iodine suspended in 10 ml of distilled water) to observe the stained ovules with a stereoscopic microscope. FIG. 13 shows stereoscopic micrographs of Transformed plants H, I, J, and K before and after staining with the iodine suspension. The iodine suspension stains starch and exhibits a blue-violet color. In other words, the fact that the iodine-starch reaction was observed in the unfertilized ovule ingredients of Transformed plants H, I, J, and K indicates that the ovules in Transformed plants H, I, J, and K develop the solid or liquid endosperms containing starch without fertilization. These results prove that Constructs H, I, J, and K having Chimeric genes H, I, J, and K, respectively, induce the spontaneous endosperm development in *Oryza sativa*.

INDUSTRIAL APPLICABILITY

The present invention is based on a technique that can artificially induce a functional endosperm in a seed plant without fertilization, and thereby has a high applicability, especially in the field for an improvement in agricultural productivity.

The invention claimed is:

1. A method of producing a transgenic seed plant capable of developing endosperm without fertilization, comprising introducing a nucleic acid molecule comprising a nucleotide sequence encoding a polypeptide having an endosperm development-inducing function into a seed-plant cell, wherein said nucleotide sequence is operably linked to a heterologous seed-specific promoter, wherein the polypeptide comprises an amino acid sequence having at least 95% amino acid sequence identity to the amino acid sequence as set forth in SEQ ID NO:1; expressing the polypeptide in the transgenic seed plant cell; and selecting a transgenic plant comprising said transgenic seed plant cell that develops endosperm without fertilization.

2. The method of claim 1, wherein the nucleotide sequence encoding the polypeptide having the endosperm development-inducing function comprises a nucleotide sequence having at least 90% nucleotide sequence identity to the nucleotide sequence as set forth in SEQ ID NO: 2.

3. The method of claim 1, wherein the nucleic acid molecule further comprises a nucleotide sequence of a terminator region, and the nucleotide sequence encoding the polypeptide having the endosperm development-inducing function is operably linked to the nucleotide sequence of the terminator region.

4. The method of claim 1, wherein said introducing comprises a vector which comprises the nucleic acid molecule.

5. The method of claim 4, wherein the vector is an *Agrobacterium* vector.

6. The method of claim 4, wherein the vector is a plant virus vector.

7. The method of claim 1, wherein the selection step comprises evaluating the transgenic plant in an unfertilized state for the presence of endosperm.

* * * * *